(12) United States Patent
Fima et al.

(10) Patent No.: US 8,476,234 B2
(45) Date of Patent: Jul. 2, 2013

(54) LONG-ACTING COAGULATION FACTORS AND METHODS OF PRODUCING SAME

(75) Inventors: Udi Eyal Fima, Beer-Sheva (IL); Gili Hart, Shoham (IL)

(73) Assignee: Prolor Biotech Inc., Nes Ziona (IL)

( * ) Notice: Subject to any disclaimer, the term of this patent is extended or adjusted under 35 U.S.C. 154(b) by 0 days.

(21) Appl. No.: 12/826,754

(22) Filed: Jun. 30, 2010

(65) Prior Publication Data

US 2010/0317585 A1 Dec. 16, 2010

Related U.S. Application Data

(60) Provisional application No. 61/224,366, filed on Jul. 9, 2009.

(51) Int. Cl.
*A61K 38/36* (2006.01)
*A61K 38/24* (2006.01)
*C07K 14/745* (2006.01)
*C07K 14/59* (2006.01)

(52) U.S. Cl.
USPC .......... 514/14.3; 514/13.7; 514/9.7; 530/384; 530/381; 530/398

(58) Field of Classification Search
None
See application file for complete search history.

(56) References Cited

U.S. PATENT DOCUMENTS

| | | | |
|---|---|---|---|
| 4,400,316 A | 8/1983 | Katsuragi et al. | |
| 4,853,332 A | 8/1989 | Mark et al. | |
| 5,177,193 A | 1/1993 | Boime | |
| 5,338,835 A | 8/1994 | Boime | |
| 5,405,945 A | 4/1995 | Boime et al. | |
| 5,585,345 A | 12/1996 | Boime | |
| 5,597,797 A | 1/1997 | Clark | |
| 5,705,478 A | 1/1998 | Boime et al. | |
| 5,712,122 A | 1/1998 | Boime et al. | |
| 5,759,818 A | 6/1998 | Boime et al. | |
| 5,792,460 A * | 8/1998 | Boime | 424/192.1 |
| 5,935,924 A | 8/1999 | Bunting et al. | |
| 5,958,737 A | 9/1999 | Boime et al. | |
| 6,028,177 A | 2/2000 | Boime | |
| 6,083,725 A | 7/2000 | Selden et al. | |
| 6,225,449 B1 | 5/2001 | Boime | |
| 6,238,890 B1 | 5/2001 | Boime et al. | |
| 6,242,580 B1 | 6/2001 | Boime et al. | |
| 6,306,654 B1 | 10/2001 | Boime et al. | |
| 6,310,183 B1 | 10/2001 | Johannessen et al. | |
| 6,340,742 B1 | 1/2002 | Burg et al. | |
| 6,514,729 B1 | 2/2003 | Bentzien | |
| 7,081,446 B2 | 7/2006 | Lustbader | |
| 7,094,566 B2 | 8/2006 | Medlock et al. | |
| 7,141,547 B2 | 11/2006 | Rosen et al. | |
| 7,202,215 B2 | 4/2007 | Lustbader | |
| 7,217,689 B1 | 5/2007 | Elliot et al. | |
| 7,371,373 B2 | 5/2008 | Shirley et al. | |
| 7,425,539 B2 | 9/2008 | Donovan et al. | |
| 7,459,429 B2 | 12/2008 | Klima et al. | |
| 7,459,435 B2 | 12/2008 | Lehmann et al. | |
| 7,459,436 B2 | 12/2008 | Lehmann et al. | |
| 7,649,084 B2 | 12/2008 | Lehmann et al. | |
| 7,553,940 B2 | 6/2009 | Fares et al. | |
| 7,553,941 B2 | 6/2009 | Fares et al. | |
| 7,666,835 B2 | 2/2010 | Bloom et al. | |
| 8,008,454 B2 | 8/2011 | Lee et al. | |
| 8,048,846 B2 | 11/2011 | Chahal et al. | |
| 8,048,848 B2 | 11/2011 | Fares et al. | |
| 8,048,849 B2 | 11/2011 | Fares et al. | |
| 8,097,435 B2 | 1/2012 | Fares et al. | |
| 8,110,376 B2 | 2/2012 | Fares et al. | |
| 8,114,836 B2 | 2/2012 | Fares et al. | |
| 2001/0007757 A1 | 7/2001 | Boime et al. | |
| 2002/0127652 A1 * | 9/2002 | Schambye et al. | 435/69.4 |
| 2003/0216313 A1 | 11/2003 | Lustbader et al. | |
| 2004/0018240 A1 | 1/2004 | Ohmachi et al. | |
| 2004/0053370 A1 | 3/2004 | Glaesner et al. | |
| 2004/0057996 A1 | 3/2004 | Takada et al. | |
| 2005/0234221 A1 | 10/2005 | Medlock et al. | |
| 2006/0088595 A1 | 4/2006 | Asakawa et al. | |
| 2007/0184530 A1 | 8/2007 | Fares et al. | |
| 2007/0190610 A1 | 8/2007 | Fares et al. | |
| 2007/0190611 A1 | 8/2007 | Fares et al. | |
| 2009/0053185 A1 | 2/2009 | Schulte et al. | |
| 2009/0087411 A1 | 4/2009 | Fares et al. | |
| 2009/0130060 A1 | 5/2009 | Weimer et al. | |
| 2009/0270489 A1 | 10/2009 | Fares et al. | |

(Continued)

FOREIGN PATENT DOCUMENTS

| | | |
|---|---|---|
| JP | 2002226365 A | 8/2002 |
| JP | 2002255857 A | 9/2002 |

(Continued)

OTHER PUBLICATIONS

Wells, J.A. Additivity of Mutational Effects in Proteins. Biochemistry 29:8509-8517 (1990).*
Ngo et al. Computational Complexity, Protein Structure Prediction and the Levinthal Paradox. The Protein Folding Problem and Tertiary Structure Prediction, pp. 433-440 and 492-495 (1994).*
Boissel et al. Erythropoietin structure-function relationships. The Journal of Biological Chemistry, vol. 268, No. 21:15983-15993 (1993).*
Uenalp et al. Factor VII deficiency associated with valproate treatment. Pediatrics International vol. 50, No. 3:403-405. Abstract. (Jun. 2008).*
Amirizahdeh et al. Expression of biologically active recombinant B-domain-deleted human VIII in mammalian cells. Journal of Sciences, Islamic Republic of Iran. Abstract. 16(2):103-112 (2005).*

(Continued)

*Primary Examiner* — Elizabeth C Kemmerer
*Assistant Examiner* — Regina M Deberry
(74) *Attorney, Agent, or Firm* — Pearl Cohen Zedek Latzer, LLP; Mark S. Cohen

(57) ABSTRACT

Polypeptides and polynucleotides encoding same comprising at least one carboxy-terminal peptide (CTP) of chorionic gonadotrophin attached to a carboxy terminus of a coagulation factor and not to an amino terminus are disclosed. Pharmaceutical compositions comprising the polypeptides and polynucleotides of the invention and methods of using same are also disclosed.

28 Claims, 7 Drawing Sheets

U.S. PATENT DOCUMENTS

| | | | |
|---|---|---|---|
| 2009/0275084 A1 | 11/2009 | Fares et al. | |
| 2009/0286733 A1 | 11/2009 | Fares et al. | |
| 2009/0312254 A1 | 12/2009 | Fares et al. | |
| 2010/0081614 A1 | 4/2010 | Fares et al. | |
| 2010/0317585 A1 | 12/2010 | Fima et al. | |

FOREIGN PATENT DOCUMENTS

| | | |
|---|---|---|
| JP | 2004269516 A | 9/2004 |
| WO | WO9424148 A1 | 10/1994 |
| WO | WO 00/23472 A2 | 4/2000 |
| WO | WO 02/48194 A1 | 6/2002 |
| WO | WO 2005/080544 | 9/2005 |
| WO | WO 2007/094985 | 8/2007 |

OTHER PUBLICATIONS

Milton et al. The Delineation of a Decapeptide Gonadotropin-releasing Sequence in the Carboxyl-terminal Extension of the Human Gonadotropin releasing Hormone Precursor; The Journal of Biological Chemistry, vol. 261/36:16990-16997 (Dec. 1986).*

Uenalp et al. Factor VII deficiency associated with valproate treatment. Pediatrics International vol. 50, No. 3:403-405 (Jun. 2008).*

Furuhashi, M. et al; 'Fusing the Carboxy-terminal Peptide of the Chorionic Gonadotropin (CG) β-Subunit to the Common a-Subunit: Retention of O-linked Glycosylation and Enhanced in vivo Bioactivity of Chimeric Human CG', Molecular Endocrinology, 1995, vol. 9, No. 1, pp. 54-63.

Furuhashi, M. et al, 'Processing of O-linked Glycosylation in the Chimera Consisting of a-Subunit and Carboxyl-terminal Peptide of the Human Chorionic Gonadotropin β-Subunit is affected by Dimer Formation with Follicle-stimulating Hormone β-Subunit', Endocrine Journal 2004, vol. 51, No. 1, pp. 53-59.

Schein, Catherine H. The shape of the messenger: using protein structure information to design novel cytokine-based therapeutics. Abstract; Current Pharmaceutical Design, vol. 8/No. 24, pp. 2113-2129 (2002).

Weiss et al. "Noncompliance in neurologic patents" Curr Treat Options Neurol. Sep. 2005;7(5):419:23.

Fares et al. "Growth Hormone (GH) Retardation of Muscle Damage due to Immobilization in Old Rats Possible Intervention with a New Long-Acting Recombinant GH" Ann NY Acad Sci. 786:430-43. Jun. 15, 1996.

Houdebine et al. "The methods to generate transgenic animals and to control transgene expression" Journal of Biotechnology vol. 98, Issues 2-3, pp. 145-160, Sep. 25, 2002.

Phillips et al. "The challenge of gene therapy and DNA delivery" Journal of Pharmacy and Pharmacology vol. 53, Issue 9, pp. 1169-1174, Sep. 2001.

Davis CG et al. "Deletion of clustered O-linked carbohydrates does not impair function of low density lipoprotein receptor in transfected fibroblasts" J Biol Chem. 261(6):2828-38, Feb. 25, 1986.

Fares et al. "Design of a long-acting follitropin agonist by fusing the C-terminal sequence of the chorionic gonadotropin beta subunit to the follitropin beta subunit" Proc Nati Acad Sci U S A., 89(10): 4304-4308, May 15, 1992.

Huston et al. "Protein engineering of antibody binding sites: Recovery of specific activity in an anti-digoxin single-chain Fv analogue produced in Escherichia coli" Proc. Natl. Acad. Sci. USA vol. 85, pp. 5879-5883, Biochemistry, Aug. 1988.

MJ Kessler et al. "Structure and location of the O-glycosidic carbohydrate units of human chorionic gonadotropin" J Biol Chem. 25;254(16):7909-14, Aug. 1979.

European Search Report Application No. PCT/IL2009000700 Dated Dec. 5, 2011.

International preliminary report on patentability Application No. PCT/IL2010/000532 Dated Jan. 19, 2012.

Ameredes et al. "Growth hormone improves body mass recovery with refeeding after chronic undernutrition-induced muscle atrophy in aging male rats." The Journal of Nutrition. 129:2264-2270 1999.

Barker et al. "An immunomagnetic-base method for the purification of ovarian cancer cells from patient-derived ascites" Gynecologic Oncology 82: 57-63, 2001.

Freshney "Culture of animal cells: A manual of basic technique" (Culture of Animal Cells, A Manual of Basic Technique, Alan R. Liss, Inc., 1983, New York, p. 4).

Su et al. "Curcumin Inhibits Human Lung Cell Carcinoma Cancer Tumour Growth in a Murine Xenograft Model" Phytother. Res. 24:189-191, 2010.

Fayad et al. "Update of the M. D. Anderson Cancer Center experience with hyper-CVAD and rituximab for the treatment of mantle cell and Burkitt-type lymphomas.". Clin Lymphoma Myeloma. Dec. 2007;8 Suppl 2:S57-62.

Kelly et al. "Outcomes of patients with Burkitt lymphoma older than age 40 treated with intensive chemotherapeutic regimens." Clin Lymphoma Myeloma. Aug. 2009;9(4):307-10.

Kessler et al., "Structures of N-Glycosidic Carbohydrate Unites of Human chorionic Gonadotropin", J. Biol. Chem. 254:7901-7908 (1979).

Li et al. Bioassay of hGH .I. Weight gain of hypophysectomized rats. Abstract, Yaowu Fenxi Zazhi 15(2), 3-7 (1995).

Smeland et al. "Treatment of Burkitt's/Burkitt-like lymphoma in adolescents and adults: a 20-year experience from the Norwegian Radium Hospital with the use of three successive regimens."Ann Oncol. Jul. 2004;15(7):1072-8.

Yin et al. "Recombinant human growth hormone replacement therapy in HIV-associated wasting and visceral adiposity". Exper. Rev. Anti-Infect. Ther. 3(5):727-736 (2005).

EP Search Report for Application No. 12150722.2 Dated Jun. 4, 2012.

Bengtsson et al. "Treatment of adults with growth hormone (GH) deficiency with recombinant human GH" J Clin Endocrinol Metab. Feb. 1993;76(2):309-17.

Drake et al. "Optimizing Gh therapy in adults and children" Endocr Rev. Aug. 2001;22(4):425-50.

Isgaard et al. "Effects of local administration of GH and IGF-1 on longitudinal bone growth in rats" Am J Physiol. Apr. 1986;250(4 Pt 1):E367-72.

Oosterhof et al. Regulation of whole body energy homeostasis with growth hormone replacement therapy and endurance exercise Physiol Genomics. Jun. 28, 2011;43(12):739-48.

Rudman et al. "Effects of human growth hormone in men over 60 years old" N Engl J Med. Jul. 5, 1990;323(1):1-6.

Russell et al. "Local injections of human or rat growth hormone or of purified human somatomedin-C stimulate unilateral tibial epiphyseal growth in hypophysectomized rats" Endocrinology. Jun. 1985;116(6):2563-7.

Yefenof & McConnell "Interferon amplifies complement activation by Burkitt's lymphoma cells" Nature. Feb. 21-27, 1985;313(6004):68.

Kotler et al. "Effects of growth hormone on abnormal visceral adipose tissue accumulation and dyslipidemia in HIV-infected patients." J Acquir Immune Defic Syndr. Mar. 1, 2004;35(3):239-52. Erratum in: J Acquir Immune Defic Syndr. Nov. 1, 2006;43(3):381.

Lo et al. "The effects of recombinant human growth hormone on body composition andglucose metabolism in HIV-infected patients with fat accumulation" J Clin Endocrinol Metab. Aug. 2001;86(8):3480-7. PubMed PMID: 11502767.

Milton et al. The delineation of a decapeptide gonadotropin-releasing sequence in the carboxyl-terminal extension of the human gonadotropin-releasing hormone precursor J Biol Chem. Dec. 25, 1986;261(36):16990-7.

"Epogen signal peptide"; XP002685292, retrieved from EBI accession No. GSP:ADS64918, Database accession No. ADW64918, Jan. 6, 2005.

Fares et al.; "Development of a Long-Acting Erythropoietin by Fusing the Carboxyl-Terminal Peptide of Human Chorionic Gonadotropin β-Subunit to the coding Sequence of Human Erythropoietin", Endocrinology 148(10):5081-5087, 2007.

European Search Report for European Patent Application No. 12179805, Sep. 11, 2012.

European Search Report for European Patent Application No. 12179821, Dec. 11, 2012.

International Search Report for PCT Application No. PCT/IL 12/50288 mailed Jan. 28, 2013.

European Search Report Application No. EP 10796803 dated Feb. 28, 2013.

Fares et al. "Designing a Long Acting Erythropoietin by Fusing Three Carboxyl-Terminal Peptides of Human Chorionic Gonadotropin β Subunit to the N-Terminal and C-Terminal Coding Sequence." Int J Cell Biol. 2011;2011:275063.

Fares et al. "Designing a long-acting human growth hormone (hGH) by fusing the carboxyl-terminal peptide of human chorionic gonadotropin beta-subunit to the coding sequence of hGH" Endocrinology. Sep. 2010;151(9):4410-7.

Joshi et al. "Recombinant thyrotropin containing a beta-subunit chimera with the human chorionic gonadotropin-beta carboxy-terminus is biologically active, with a prolonged plasma half-life: role of carbohydrate in bioactivity and metabolic clearance" Endocrinology. Sep. 1995;136(9):3839-48.

Anson et al. "The gene structure of human anti-haemophilic factor IX", The EMBO Journal (1984) 3(5):1053-1060.

Berntorp et al. "The pharmacokinetics of clotting factor therapy"; Haemophilia (2003) 9:353-359.

Database Geneseq [Online] Apr. 7, 2005, "Human interferon beta (without signal peptide)." XP002664024 retrieved from EBI accession No. GSP: ADW02285, Database accession No. ADW02285.

Persson et al. "Recombinant coagulation factor VIIa—from molecular to clinical aspects of a versatile haemostatic agent", Thrombosis Research (2010) 125:483-489.

Schulte "Half-life extension through albumin fusion technologies", Thrombosis Research (2009) 124 Suppl. 2;S6-S8.

Sheffield et al. "Effects of genetic fusion of factor IX to albumin on in vivo clearance in mice and rabbits", Blackwell Publishing Ltd, British Journal of Haematology (2004) 126:565-573.

White et al. "Mammalian Recombinant Coagulation Proteins: Structure and Function", Transfus. Sci. (1998) 19(2):177-189.

* cited by examiner

| Protein | rhFIX | Hum. Plasma | MOD-3012 |
|---|---|---|---|
| Specific Activity (U/mg) | 178 | 228 | 166 |

SEQUENCE LISTING

```
<160> NUMBER OF SEQ ID NOS: 23

<210> SEQ ID NO 1
<211> LENGTH: 32
<212> TYPE: PRT
<213> ORGANISM: Homo sapiens

<400> SEQUENCE: 1

Asp Pro Arg Phe Gln Asp Ser Ser Ser Lys Ala Pro Pro Pro Ser
1               5                   10                  15

Leu Pro Ser Pro Ser Arg Leu Pro Gly Pro Ser Asp Thr Pro Ile Leu
            20                  25                  30

<210> SEQ ID NO 2
<211> LENGTH: 28
<212> TYPE: PRT
<213> ORGANISM: Homo sapiens

<400> SEQUENCE: 2

Ser Ser Ser Ser Lys Ala Pro Pro Pro Ser Leu Pro Ser Pro Ser Arg
1               5                   10                  15

Leu Pro Gly Pro Ser Asp Thr Pro Ile Leu Pro Gln
            20                  25

<210> SEQ ID NO 3
<211> LENGTH: 12
<212> TYPE: PRT
<213> ORGANISM: Homo sapiens

<400> SEQUENCE: 3

Ser Ser Ser Ser Lys Ala Pro Pro Pro Ser Leu Pro
1               5                   10

<210> SEQ ID NO 4
<211> LENGTH: 28
<212> TYPE: PRT
<213> ORGANISM: Homo sapiens
```

-continued

```
<400> SEQUENCE: 4

Ser Ser Ser Ser Lys Ala Pro Pro Ser Leu Pro Pro Ser Arg
1               5                   10                  15

Leu Pro Gly Pro Ser Asp Thr Pro Ile Leu Pro Gln
            20                  25

<210> SEQ ID NO 5
<211> LENGTH: 25
<212> TYPE: DNA
<213> ORGANISM: Artificial Sequence
<220> FEATURE:
<223> OTHER INFORMATION: PCR primer for Factor VII

<400> SEQUENCE: 5
ctcgaggaca tggtctccca ggccc                                           25

<210> SEQ ID NO 6
<211> LENGTH: 25
<212> TYPE: DNA
<213> ORGANISM: Artificial Sequence
<220> FEATURE:
<223> OTHER INFORMATION: PCR primer for Factor VII

<400> SEQUENCE: 6
tctagaatag gtattttcc acatg                                            25

<210> SEQ ID NO 7
<211> LENGTH: 22
<212> TYPE: DNA
<213> ORGANISM: Artificial Sequence
<220> FEATURE:
<223> OTHER INFORMATION: PCR primer for Factor VII

<400> SEQUENCE: 7
tctagaaaaa agaaatgcca gc                                              22

<210> SEQ ID NO 8
<211> LENGTH: 32
<212> TYPE: DNA
<213> ORGANISM: Artificial Sequence
<220> FEATURE:
<223> OTHER INFORMATION: PCR primer for Factor VII

<400> SEQUENCE: 8
gcggccgcat cctcagggaa atggggctcg ca                                   32

<210> SEQ ID NO 9
<211> LENGTH: 444
<212> TYPE: PRT
<213> ORGANISM: Homo sapiens

<400> SEQUENCE: 9

Met Val Ser Gln Ala Leu Arg Leu Leu Cys Leu Leu Leu Gly Leu Gln
1               5                   10                  15

Gly Cys Leu Ala Ala Val Phe Val Thr Gln Glu Glu Ala His Gly Val
            20                  25                  30

Leu His Arg Arg Arg Arg Ala Asn Ala Phe Leu Glu Glu Leu Arg Pro
        35                  40                  45

Gly Ser Leu Glu Arg Glu Cys Lys Glu Glu Gln Cys Ser Phe Glu Glu
    50                  55                  60

Ala Arg Glu Ile Phe Lys Asp Ala Glu Arg Thr Lys Leu Phe Trp Ile
65                  70                  75                  80

Ser Tyr Ser Asp Gly Asp Gln Cys Ala Ser Ser Pro Cys Gln Asn Gly
```

```
                85                  90                  95
Gly Ser Cys Lys Asp Gln Leu Gln Ser Tyr Ile Cys Phe Cys Leu Pro
            100                 105                 110

Ala Phe Glu Gly Arg Asn Cys Glu Thr His Lys Asp Asp Gln Leu Ile
            115                 120                 125

Cys Val Asn Glu Asn Gly Gly Cys Glu Gln Tyr Cys Ser Asp His Thr
            130                 135                 140

Gly Thr Lys Arg Ser Cys Arg Cys His Glu Gly Tyr Ser Leu Leu Ala
145                 150                 155                 160

Asp Gly Val Ser Cys Thr Pro Thr Val Glu Tyr Pro Cys Gly Lys Ile
                165                 170                 175

Pro Ile Leu Glu Lys Arg Asn Ala Ser Lys Pro Gln Gly Arg Ile Val
                180                 185                 190

Gly Gly Lys Val Cys Pro Lys Gly Glu Cys Pro Trp Gln Val Leu Leu
                195                 200                 205

Leu Val Asn Gly Ala Gln Leu Cys Gly Gly Thr Leu Ile Asn Thr Ile
            210                 215                 220

Trp Val Val Ser Ala Ala His Cys Phe Asp Lys Ile Lys Asn Trp Arg
225                 230                 235                 240

Asn Leu Ile Ala Val Leu Gly Glu His Asp Leu Ser Glu His Asp Gly
                245                 250                 255

Asp Glu Gln Ser Arg Arg Val Ala Gln Val Ile Ile Pro Ser Thr Tyr
                260                 265                 270

Val Pro Gly Thr Thr Asn His Asp Ile Ala Leu Leu Arg Leu His Gln
                275                 280                 285

Pro Val Val Leu Thr Asp His Val Val Pro Leu Cys Leu Pro Glu Arg
            290                 295                 300

Thr Phe Ser Glu Arg Thr Leu Ala Phe Val Arg Phe Ser Leu Val Ser
305                 310                 315                 320

Gly Trp Gly Gln Leu Leu Asp Arg Gly Ala Thr Ala Leu Glu Leu Met
                325                 330                 335

Val Leu Asn Val Pro Arg Leu Met Thr Gln Asp Cys Leu Gln Gln Ser
            340                 345                 350

Arg Lys Val Gly Asp Ser Pro Asn Ile Thr Glu Tyr Met Phe Cys Ala
            355                 360                 365

Gly Tyr Ser Asp Gly Ser Lys Asp Ser Cys Lys Gly Asp Ser Gly Gly
            370                 375                 380

Pro His Ala Thr His Tyr Arg Gly Thr Trp Tyr Leu Thr Gly Ile Val
385                 390                 395                 400

Ser Trp Gly Gln Gly Cys Ala Thr Val Gly His Phe Gly Val Tyr Thr
                405                 410                 415

Arg Val Ser Gln Tyr Ile Glu Trp Leu Gln Lys Leu Met Arg Ser Glu
            420                 425                 430

Pro Arg Pro Gly Val Leu Leu Arg Ala Pro Phe Pro
            435                 440

<210> SEQ ID NO 10
<211> LENGTH: 448
<212> TYPE: PRT
<213> ORGANISM: Homo sapiens

<400> SEQUENCE: 10

Met Val Ser Gln Ala Leu Arg Leu Leu Cys Leu Leu Leu Gly Leu Gln
1               5                   10                  15

Gly Cys Leu Ala Ala Val Phe Val Thr Gln Glu Glu Ala His Gly Val
```

```
                    20                  25                  30
Leu His Arg Arg Arg Ala Asn Ala Phe Leu Glu Glu Leu Arg Pro
            35                  40                  45
Gly Ser Leu Glu Arg Glu Cys Lys Glu Glu Gln Cys Ser Phe Glu
        50                  55                  60
Ala Arg Glu Ile Phe Lys Asp Ala Glu Arg Thr Lys Leu Phe Trp Ile
65                  70                  75                  80
Ser Tyr Ser Asp Gly Asp Gln Cys Ala Ser Ser Pro Cys Gln Asn Gly
                85                  90                  95
Gly Ser Cys Lys Asp Gln Leu Gln Ser Tyr Ile Cys Phe Cys Leu Pro
                100                 105                 110
Ala Phe Glu Gly Arg Asn Cys Glu Thr His Lys Asp Asp Gln Leu Ile
            115                 120                 125
Cys Val Asn Glu Asn Gly Gly Cys Glu Gln Tyr Cys Ser Asp His Thr
        130                 135                 140
Gly Thr Lys Arg Ser Cys Arg Cys His Glu Gly Tyr Ser Leu Leu Ala
145                 150                 155                 160
Asp Gly Val Ser Cys Thr Pro Thr Val Glu Tyr Pro Cys Gly Lys Ile
                165                 170                 175
Pro Ile Leu Glu Lys Arg Asn Ala Ser Lys Pro Gln Gly Arg Ile Val
                180                 185                 190
Gly Gly Lys Val Cys Pro Lys Gly Glu Cys Pro Trp Gln Val Leu Leu
                195                 200                 205
Leu Val Asn Gly Ala Gln Leu Cys Gly Gly Thr Leu Ile Asn Thr Ile
            210                 215                 220
Trp Val Val Ser Ala Ala His Cys Phe Asp Lys Ile Lys Asn Trp Arg
225                 230                 235                 240
Asn Leu Ile Ala Val Leu Gly Glu His Asp Leu Ser Glu His Asp Gly
                245                 250                 255
Asp Glu Gln Ser Arg Arg Val Ala Gln Val Ile Ile Pro Ser Thr Tyr
            260                 265                 270
Val Pro Gly Thr Thr Asn His Asp Ile Ala Leu Leu Arg Leu His Gln
        275                 280                 285
Pro Val Val Leu Thr Asp His Val Val Pro Leu Cys Leu Pro Glu Arg
        290                 295                 300
Thr Phe Ser Glu Arg Thr Leu Ala Phe Val Arg Phe Ser Leu Val Ser
305                 310                 315                 320
Gly Trp Gly Gln Leu Leu Asp Arg Gly Ala Thr Ala Leu Glu Leu Met
            325                 330                 335
Val Leu Asn Val Pro Arg Leu Met Thr Gln Asp Cys Leu Gln Gln Ser
        340                 345                 350
Arg Lys Val Gly Asp Ser Pro Asn Ile Thr Glu Tyr Met Phe Cys Ala
        355                 360                 365
Gly Tyr Ser Asp Gly Ser Lys Asp Ser Cys Lys Gly Asp Ser Gly Gly
            370                 375                 380
Pro His Ala Thr His Tyr Arg Gly Thr Trp Tyr Leu Thr Gly Ile Val
385                 390                 395                 400
Ser Trp Gly Gln Gly Cys Ala Thr Val Gly His Phe Gly Val Tyr Thr
                405                 410                 415
Arg Val Ser Gln Tyr Ile Glu Trp Leu Gln Lys Leu Met Arg Ser Glu
                420                 425                 430
Pro Arg Pro Gly Val Leu Leu Arg Ala Pro Phe Pro Gly Cys Gly Arg
            435                 440                 445
```

<210> SEQ ID NO 11
<211> LENGTH: 1356
<212> TYPE: DNA
<213> ORGANISM: Homo sapiens

<400> SEQUENCE: 11

| | | | | | |
|---|---|---|---|---|---|
| ctcgaggaca | tggtctccca | ggccctcagg | ctcctctgcc | ttctgcttgg | gcttcagggc | 60 |
| tgcctggctg | cagtcttcgt | aacccaggag | gaagcccacg | gcgtcctgca | ccggcgccgg | 120 |
| cgcgccaacg | cgttcctgga | ggagctgcgg | ccgggctccc | tggagaggga | gtgcaaggag | 180 |
| gagcagtgct | ccttcgagga | ggcccgggag | atcttcaagg | acgcggagag | gacgaagctg | 240 |
| ttctggattt | cttacagtga | tggggaccag | tgtgcctcaa | gtccatgcca | gaatggggc | 300 |
| tcctgcaagg | accagctcca | gtcctatatc | tgcttctgcc | tccctgcctt | cgagggccgg | 360 |
| aactgtgaga | cgcacaagga | tgaccagctg | atctgtgtga | acgagaacgg | cggctgtgag | 420 |
| cagtactgca | gtgaccacac | gggcaccaag | cgctcctgtc | ggtgccacga | ggggtactct | 480 |
| ctgctggcag | acggggtgtc | ctgcacaccc | acagttgaat | atccatgtgg | aaaaatacct | 540 |
| attctagaaa | aagaaatgc | cagcaaaccc | caaggccgaa | ttgtgggggg | caaggtgtgc | 600 |
| cccaaggggg | agtgtccatg | gcaggtcctg | ttgttggtga | atggagctca | gttgtgtggg | 660 |
| gggaccctga | tcaacaccat | ctgggtggtc | tccgcggccc | actgtttcga | caaaatcaag | 720 |
| aactggagga | acctgatcgc | ggtgctgggc | gagcacgacc | tcagcgagca | cgacggggat | 780 |
| gagcagagcc | ggcgggtggc | gcaggtcatc | atccccagca | cgtacgtccc | gggcaccacc | 840 |
| aaccacgaca | tcgcgctgct | ccgcctgcac | cagcccgtgg | tcctcactga | ccatgtggtg | 900 |
| cccctctgcc | tgcccgaacg | gacgttctct | gagaggacgc | tggccttcgt | gcgcttctca | 960 |
| ttggtcagcg | gctggggcca | gctgctggac | cgtggcgcca | cggccctgga | gctcatggtc | 1020 |
| ctcaacgtgc | cccggctgat | gacccaggac | tgcctgcagc | agtcacgaa | ggtgggagac | 1080 |
| tccccaaata | tcacggagta | catgttctgt | gccggctact | cggatggcag | caaggactcc | 1140 |
| tgcaaggggg | acagtggagg | cccacatgcc | acccactacc | ggggcacgtg | gtacctgacg | 1200 |
| ggcatcgtca | gctggggcca | gggctgcgca | accgtgggcc | actttgggt | gtacaccagg | 1260 |
| gtctcccagt | acatcgagtg | gctgcaaaag | ctcatgcgct | cagagccacg | cccaggagtc | 1320 |
| ctcctgcgag | ccccatttcc | ctgaggatgc | ggccgc | | | 1356 |

<210> SEQ ID NO 12
<211> LENGTH: 1442
<212> TYPE: DNA
<213> ORGANISM: Homo sapiens

<400> SEQUENCE: 12

| | | | | | |
|---|---|---|---|---|---|
| ctcgaggaca | tggtctccca | ggccctcagg | ctcctctgcc | ttctgcttgg | gcttcagggc | 60 |
| tgcctggctg | cagtcttcgt | aacccaggag | gaagcccacg | gcgtcctgca | ccggcgccgg | 120 |
| cgcgccaacg | cgttcctgga | ggagctgcgg | ccgggctccc | tggagaggga | gtgcaaggag | 180 |
| gagcagtgct | ccttcgagga | ggcccgggag | atcttcaagg | acgcggagag | gacgaagctg | 240 |
| ttctggattt | cttacagtga | tggggaccag | tgtgcctcaa | gtccatgcca | gaatggggc | 300 |
| tcctgcaagg | accagctcca | gtcctatatc | tgcttctgcc | tccctgcctt | cgagggccgg | 360 |
| aactgtgaga | cgcacaagga | tgaccagctg | atctgtgtga | acgagaacgg | cggctgtgag | 420 |
| cagtactgca | gtgaccacac | gggcaccaag | cgctcctgtc | ggtgccacga | ggggtactct | 480 |
| ctgctggcag | acggggtgtc | ctgcacaccc | acagttgaat | atccatgtgg | aaaaatacct | 540 |

```
attctagaaa aaagaaatgc cagcaaaccc caaggccgaa ttgtgggggg caaggtgtgc      600
cccaaagggg agtgtccatg gcaggtcctg ttgttggtga atggagctca gttgtgtggg      660
gggaccctga tcaacaccat ctgggtggtc tccgcggccc actgtttcga caaaatcaag      720
aactggagga acctgatcgc ggtgctgggc gagcacgacc tcagcgagca cgacggggat      780
gagcagagcc ggcgggtggc gcaggtcatc atccccagca cgtacgtccc gggcaccacc      840
aaccacgaca tcgcgctgct ccgcctgcac cagcccgtgg tcctcactga ccatgtggtg      900
cccctctgcc tgcccgaacg gacgttctct gagaggacgc tggccttcgt gcgcttctca      960
ttggtcagcg gctggggcca gctgctggac cgtggcgcca cggccctgga gctcatggtc     1020
ctcaacgtgc cccggctgat gacccaggac tgcctgcagc agtcacggaa ggtgggagac     1080
tccccaaata tcacggagta catgttctgt gccggctact cggatggcag caaggactcc     1140
tgcaaggggg acagtggagg cccacatgcc acccactacc ggggcacgtg gtacctgacc     1200
ggcatcgtga gctggggcca gggctgcgcc accgtgggcc acttcggcgt gtacaccagg     1260
gtgtcccagt acatcgagtg gctgcagaaa ctgatgagaa gcgagcccag acccggcgtg     1320
ctgctgagag cccccttccc cagcagcagc tccaaggccc ctcccctag cctgcccagc     1380
cctagcagac tgcctgggcc cagcgacacc cccatcctgc cccagtgagg atccgcggcc     1440
gc                                                                    1442

<210> SEQ ID NO 13
<211> LENGTH: 472
<212> TYPE: PRT
<213> ORGANISM: Homo sapiens

<400> SEQUENCE: 13

Met Val Ser Gln Ala Leu Arg Leu Leu Cys Leu Leu Leu Gly Leu Gln
1               5                   10                  15

Gly Cys Leu Ala Ala Val Phe Val Thr Gln Glu Glu Ala His Gly Val
            20                  25                  30

Leu His Arg Arg Arg Arg Ala Asn Ala Phe Leu Glu Glu Leu Arg Pro
        35                  40                  45

Gly Ser Leu Glu Arg Glu Cys Lys Glu Glu Gln Cys Ser Phe Glu Glu
    50                  55                  60

Ala Arg Glu Ile Phe Lys Asp Ala Glu Arg Thr Lys Leu Phe Trp Ile
65                  70                  75                  80

Ser Tyr Ser Asp Gly Asp Gln Cys Ala Ser Ser Pro Cys Gln Asn Gly
                85                  90                  95

Gly Ser Cys Lys Asp Gln Leu Gln Ser Tyr Ile Cys Phe Cys Leu Pro
            100                 105                 110

Ala Phe Glu Gly Arg Asn Cys Glu Thr His Lys Asp Asp Gln Leu Ile
        115                 120                 125

Cys Val Asn Glu Asn Gly Gly Cys Glu Gln Tyr Cys Ser Asp His Thr
    130                 135                 140

Gly Thr Lys Arg Ser Cys Arg Cys His Glu Gly Tyr Ser Leu Leu Ala
145                 150                 155                 160

Asp Gly Val Ser Cys Thr Pro Thr Val Glu Tyr Pro Cys Gly Lys Ile
                165                 170                 175

Pro Ile Leu Glu Lys Arg Asn Ala Ser Lys Pro Gln Gly Arg Ile Val
            180                 185                 190

Gly Gly Lys Val Cys Pro Lys Gly Glu Cys Pro Trp Gln Val Leu Leu
        195                 200                 205

Leu Val Asn Gly Ala Gln Leu Cys Gly Gly Thr Leu Ile Asn Thr Ile
```

```
                    210                 215                 220
Trp Val Ser Ala Ala His Cys Phe Asp Lys Ile Lys Asn Trp Arg
225                 230                 235                 240

Asn Leu Ile Ala Val Leu Gly Glu His Asp Leu Ser Glu His Asp Gly
                245                 250                 255

Asp Glu Gln Ser Arg Arg Val Ala Gln Val Ile Ile Pro Ser Thr Tyr
                260                 265                 270

Val Pro Gly Thr Thr Asn His Asp Ile Ala Leu Leu Arg Leu His Gln
                275                 280                 285

Pro Val Val Leu Thr Asp His Val Val Pro Leu Cys Leu Pro Glu Arg
290                 295                 300

Thr Phe Ser Glu Arg Thr Leu Ala Phe Val Arg Phe Ser Leu Val Ser
305                 310                 315                 320

Gly Trp Gly Gln Leu Leu Asp Arg Gly Ala Thr Ala Leu Glu Leu Met
                325                 330                 335

Val Leu Asn Val Pro Arg Leu Met Thr Gln Asp Cys Leu Gln Gln Ser
                340                 345                 350

Arg Lys Val Gly Asp Ser Pro Asn Ile Thr Glu Tyr Met Phe Cys Ala
                355                 360                 365

Gly Tyr Ser Asp Gly Ser Lys Asp Ser Cys Lys Gly Asp Ser Gly Gly
                370                 375                 380

Pro His Ala Thr His Tyr Arg Gly Thr Trp Tyr Leu Thr Gly Ile Val
385                 390                 395                 400

Ser Trp Gly Gln Gly Cys Ala Thr Val Gly His Phe Gly Val Tyr Thr
                405                 410                 415

Arg Val Ser Gln Tyr Ile Glu Trp Leu Gln Lys Leu Met Arg Ser Glu
                420                 425                 430

Pro Arg Pro Gly Val Leu Leu Arg Ala Pro Phe Pro Ser Ser Ser Ser
                435                 440                 445

Lys Ala Pro Pro Pro Ser Leu Pro Ser Pro Ser Arg Leu Pro Gly Pro
                450                 455                 460

Ser Asp Thr Pro Ile Leu Pro Gln
465                 470

<210> SEQ ID NO 14
<211> LENGTH: 1535
<212> TYPE: DNA
<213> ORGANISM: Homo sapiens

<400> SEQUENCE: 14
ctcgaggaca tggtctccca ggccctcagg ctcctctgcc ttctgcttgg gcttcagggc      60
tgcctggctg cagtcttcgt aacccaggag gaagcccacg gcgtcctgca ccggcgccgg     120
cgcgccaacg cgttcctgga ggagctgcgg ccgggctccc tggagaggga gtgcaaggag     180
gagcagtgct ccttcgagga ggcccgggag atcttcaagg acgcggagag gacgaagctg     240
ttctggattt cttacagtga tggggaccag tgtgcctcaa gtccatgcca gaatggggc      300 tcctgcaagg accagctcca gtcctatatc tgcttctgcc tccctgcctt cgagggccgg     360
aactgtgaga cgcacaagga tgaccagctg atctgtgtga cgagaacgg cggctgtgag     420 cagtactgca gtgaccacac gggcaccaag cgctcctgtc ggtgccacga ggggtactct     480
ctgctggcag acgggtgtc ctgcacaccc acagttgaat atccatgtgg aaaaatacct     540
attctagaaa aagaaatgc cagcaaaccc caaggccgaa ttgtgggggg caaggtgtgc     600
cccaaagggg agtgtccatg caggtcctg ttgttggtga atggagctca gttgtgtggg     660
```

-continued

```
gggaccctga tcaacaccat ctgggtggtc tccgcggccc actgtttcga caaaatcaag      720
aactggagga acctgatcgc ggtgctgggc gagcacgacc tcagcgagca cgacggggat      780
gagcagagcc ggcgggtggc gcaggtcatc atccccagca cgtacgtccc gggcaccacc      840
aaccacgaca tcgcgctgct ccgcctgcac cagcccgtgg tcctcactga ccatgtggtg      900
cccctctgcc tgcccgaacg gacgttctct gagaggacgc tggccttcgt gcgcttctca      960
ttggtcagcg ctggggcca gctgctggac cgtggcgcca cggccctgga gctcatggtc     1020
ctcaacgtgc cccggctgat gacccaggac tgcctgcagc agtcacggaa ggtgggagac     1080
tccccaaata tcacggagta catgttctgt gccggctact cggatggcag caaggactcc     1140 tgcaagggg acagtggagg cccacatgcc acccactacc ggggcacgtg gtacctgacc     1200
ggcatcgtga gctggggcca gggctgcgcc accgtgggcc acttcggcgt gtacaccagg     1260
gtgtcccagt acatcgagtg gctgcagaaa ctgatgagaa gcgagcccag accggcgtg     1320 ctgctgagag ccccttccc cagcagcagc tccaaggccc ctcccctag cctgcccagc      1380 cctagcagac tgcctgggcc ctccgacaca ccaatcctgc cacagagcag ctcctctaag     1440
gcccctcctc catccctgcc atccccctcc cggctgccag gcccctctga caccccatc     1500 ctgcctcagt gatgaaggtc tggatccgcg gccgc                              1535
```

<210> SEQ ID NO 15
<211> LENGTH: 500
<212> TYPE: PRT
<213> ORGANISM: Homo sapiens

<400> SEQUENCE: 15

```
Met Val Ser Gln Ala Leu Arg Leu Leu Cys Leu Leu Leu Gly Leu Gln
1               5                   10                  15

Gly Cys Leu Ala Ala Val Phe Val Thr Gln Glu Glu Ala His Gly Val
            20                  25                  30

Leu His Arg Arg Arg Ala Asn Ala Phe Leu Glu Glu Leu Arg Pro
        35                  40                  45

Gly Ser Leu Glu Arg Glu Cys Lys Glu Glu Gln Cys Ser Phe Glu Glu
    50                  55                  60

Ala Arg Glu Ile Phe Lys Asp Ala Glu Arg Thr Lys Leu Phe Trp Ile
65                  70                  75                  80

Ser Tyr Ser Asp Gly Asp Gln Cys Ala Ser Pro Cys Gln Asn Gly
                85                  90                  95

Gly Ser Cys Lys Asp Gln Leu Gln Ser Tyr Ile Cys Phe Cys Leu Pro
            100                 105                 110

Ala Phe Glu Gly Arg Asn Cys Glu Thr His Lys Asp Asp Gln Leu Ile
        115                 120                 125

Cys Val Asn Glu Asn Gly Gly Cys Glu Gln Tyr Cys Ser Asp His Thr
    130                 135                 140

Gly Thr Lys Arg Ser Cys Arg Cys His Glu Gly Tyr Ser Leu Leu Ala
145                 150                 155                 160

Asp Gly Val Ser Cys Thr Pro Thr Val Glu Tyr Pro Cys Gly Lys Ile
                165                 170                 175

Pro Ile Leu Glu Lys Arg Asn Ala Ser Lys Pro Gln Gly Arg Ile Val
            180                 185                 190

Gly Gly Lys Val Cys Pro Lys Gly Glu Cys Pro Trp Gln Val Leu Leu
        195                 200                 205

Leu Val Asn Gly Ala Gln Leu Cys Gly Gly Thr Leu Ile Asn Thr Ile
    210                 215                 220
```

```
Trp Val Val Ser Ala Ala His Cys Phe Asp Lys Ile Lys Asn Trp Arg
225                 230                 235                 240

Asn Leu Ile Ala Val Leu Gly Glu His Asp Leu Ser Glu His Asp Gly
            245                 250                 255

Asp Glu Gln Ser Arg Arg Val Ala Gln Val Ile Ile Pro Ser Thr Tyr
        260                 265                 270

Val Pro Gly Thr Thr Asn His Asp Ile Ala Leu Leu Arg Leu His Gln
    275                 280                 285

Pro Val Val Leu Thr Asp His Val Pro Leu Cys Leu Pro Glu Arg
290                 295                 300

Thr Phe Ser Glu Arg Thr Leu Ala Phe Val Arg Phe Ser Leu Val Ser
305                 310                 315                 320

Gly Trp Gly Gln Leu Leu Asp Arg Gly Ala Thr Ala Leu Glu Leu Met
            325                 330                 335

Val Leu Asn Val Pro Arg Leu Met Thr Gln Asp Cys Leu Gln Gln Ser
        340                 345                 350

Arg Lys Val Gly Asp Ser Pro Asn Ile Thr Glu Tyr Met Phe Cys Ala
    355                 360                 365

Gly Tyr Ser Asp Gly Ser Lys Asp Ser Cys Lys Gly Asp Ser Gly Gly
370                 375                 380

Pro His Ala Thr His Tyr Arg Gly Thr Trp Tyr Leu Thr Gly Ile Val
385                 390                 395                 400

Ser Trp Gly Gln Gly Cys Ala Thr Val Gly His Phe Gly Val Tyr Thr
            405                 410                 415

Arg Val Ser Gln Tyr Ile Glu Trp Leu Gln Lys Leu Met Arg Ser Glu
        420                 425                 430

Pro Arg Pro Gly Val Leu Leu Arg Ala Pro Phe Pro Ser Ser Ser
    435                 440                 445

Lys Ala Pro Pro Ser Leu Pro Ser Pro Ser Arg Leu Pro Gly Pro
450                 455                 460

Ser Asp Thr Pro Ile Leu Pro Gln Ser Ser Ser Lys Ala Pro Pro
465                 470                 475                 480

Pro Ser Leu Pro Ser Pro Ser Arg Leu Pro Gly Pro Ser Asp Thr Pro
            485                 490                 495

Ile Leu Pro Gln
            500

<210> SEQ ID NO 16
<211> LENGTH: 1404
<212> TYPE: DNA
<213> ORGANISM: Homo sapiens

<400> SEQUENCE: 16
gcgatcgcca tgcagcgcgt gaacatgatc atggcagaat caccaggcct catcaccatt     60
gccttttagg atatctactc agtgctgaat gtacagtttt tcttgatcat gaaaacgcca    120
acaaaattct gaatcggcca agaggtata attcaggtaa attggaagag tttgttcaag    180
ggaaccttga gagaatgt atggaagaaa agtgtagttt tgaagaagca cgagaagttt    240
ttgaaaacac tgaagaaca actgaatttt ggaagcagta tgttgatgga gatcagtgtg    300
agtccaatcc atgtttaaat ggcggcagtt gcaaggatga cattaattcc tatgaatgtt    360
ggtgtccctt tggatttgaa ggaaagaact gtgaattaga tgtaacatgt aacattaaga    420
atggcagatg cgagcagttt tgtaaaaata tgtctgataa caggtggtt tgctcctgta    480 ctgagggata tcgacttgca gaaaaccaga agtcctgtga accagcagtg ccatttccat    540
```

```
gtggaagagt ttctgtttca caaacttcta agctcacccg tgctgagact gttttcctg      600
atgtggacta tgtaaattct actgaagctg aaaccatttt ggataacatc actcaaagca     660
cccaatcatt taatgacttc actcgagttg ttggtggaga agatgccaaa ccaggtcaat     720
tcccttggca ggttgttttg aatggtaaag ttgatgcatt ctgtggaggc tctatcgtta     780
atgaaaaatg gattgtaact gctgcccact gtgttgaaac tggtgttaaa attacagttg     840
tcgcaggtga acataatatt gaggagacag aacatacaga gcaaaagcga atgtgattc      900
gaattattcc tcaccacaac tacaatgcag ctattaataa gtacaaccat gacattgccc     960
ttctggaact ggacgaaccc ttagtgctaa acagctacgt tacacctatt tgcattgctg    1020
acaaggaata cacgaacatc ttcctcaaat ttggatctgg ctatgtaagt ggctggggaa    1080
gagtcttcca aaagggaga tcagctttag ttctccagta ccttagagtt ccacttgttg     1140
accgagccac atgtcttcga tctacaaagt tcaccatcta taacaacatg ttctgtgctg    1200
gcttccatga aggaggtaga gattcatgtc aaggagatag tggggaccc catgttactg     1260
aagtggaagg gaccagtttc ttaactggaa ttattagctg gggtgaagag tgtgcaatga    1320
aaggcaaata tggaatatat accaaggtat cccggtatgt caactggatt aaggaaaaaa    1380
caaagctcac ttgaacgcgg ccgc                                           1404
```

<210> SEQ ID NO 17
<211> LENGTH: 461
<212> TYPE: PRT
<213> ORGANISM: Homo sapiens

<400> SEQUENCE: 17

```
Met Gln Arg Val Asn Met Ile Met Ala Glu Ser Pro Gly Leu Ile Thr
1               5                   10                  15

Ile Cys Leu Leu Gly Tyr Leu Leu Ser Ala Glu Cys Thr Val Phe Leu
                20                  25                  30

Asp His Glu Asn Ala Asn Lys Ile Leu Asn Arg Pro Lys Arg Tyr Asn
            35                  40                  45

Ser Gly Lys Leu Glu Glu Phe Val Gln Gly Asn Leu Glu Arg Glu Cys
        50                  55                  60

Met Glu Glu Lys Cys Ser Phe Glu Glu Ala Arg Glu Val Phe Glu Asn
65                  70                  75                  80

Thr Glu Arg Thr Thr Glu Phe Trp Lys Gln Tyr Val Asp Gly Asp Gln
                85                  90                  95

Cys Glu Ser Asn Pro Cys Leu Asn Gly Gly Ser Cys Lys Asp Asp Ile
            100                 105                 110

Asn Ser Tyr Glu Cys Trp Cys Pro Phe Gly Phe Glu Gly Lys Asn Cys
        115                 120                 125

Glu Leu Asp Val Thr Cys Asn Ile Lys Asn Gly Arg Cys Glu Gln Phe
    130                 135                 140

Cys Lys Asn Ser Ala Asp Asn Lys Val Val Cys Ser Cys Thr Glu Gly
145                 150                 155                 160

Tyr Arg Leu Ala Glu Asn Gln Lys Ser Cys Glu Pro Ala Val Pro Phe
                165                 170                 175

Pro Cys Gly Arg Val Ser Val Ser Gln Thr Ser Lys Leu Thr Arg Ala
            180                 185                 190

Glu Thr Val Phe Pro Asp Val Asp Tyr Val Asn Ser Thr Glu Ala Glu
        195                 200                 205

Thr Ile Leu Asp Asn Ile Thr Gln Ser Thr Gln Ser Phe Asn Asp Phe
    210                 215                 220
```

```
Thr Arg Val Val Gly Gly Glu Asp Ala Lys Pro Gly Gln Phe Pro Trp
225                 230                 235                 240

Gln Val Val Leu Asn Gly Lys Val Asp Ala Phe Cys Gly Gly Ser Ile
            245                 250                 255

Val Asn Glu Lys Trp Ile Val Thr Ala Ala His Cys Val Glu Thr Gly
        260                 265                 270

Val Lys Ile Thr Val Val Ala Gly Glu His Asn Ile Glu Glu Thr Glu
    275                 280                 285

His Thr Glu Gln Lys Arg Asn Val Arg Ile Ile Pro His His Asn
290                 295                 300

Tyr Asn Ala Ala Ile Asn Lys Tyr Asn His Asp Ile Ala Leu Leu Glu
305                 310                 315                 320

Leu Asp Glu Pro Leu Val Leu Asn Ser Tyr Val Thr Pro Ile Cys Ile
            325                 330                 335

Ala Asp Lys Glu Tyr Thr Asn Ile Phe Leu Lys Phe Gly Ser Gly Tyr
        340                 345                 350

Val Ser Gly Trp Gly Arg Val Phe His Lys Gly Arg Ser Ala Leu Val
    355                 360                 365

Leu Gln Tyr Leu Arg Val Pro Leu Val Asp Arg Ala Thr Cys Leu Arg
370                 375                 380

Ser Thr Lys Phe Thr Ile Tyr Asn Asn Met Phe Cys Ala Gly Phe His
385                 390                 395                 400

Glu Gly Gly Arg Asp Ser Cys Gln Gly Asp Ser Gly Gly Pro His Val
            405                 410                 415

Thr Glu Val Glu Gly Thr Ser Phe Leu Thr Gly Ile Ile Ser Trp Gly
        420                 425                 430

Glu Glu Cys Ala Met Lys Gly Lys Tyr Gly Ile Tyr Thr Lys Val Ser
    435                 440                 445

Arg Tyr Val Asn Trp Ile Lys Glu Lys Thr Lys Leu Thr
450                 455                 460

<210> SEQ ID NO 18
<211> LENGTH: 1502
<212> TYPE: DNA
<213> ORGANISM: Homo sapiens

<400> SEQUENCE: 18
gcgatcgcca tgcagcgcgt gaacatgatc atggcagaat caccaggcct catcaccatc        60
tgccttttag atatctact cagtgctgaa tgtacagttt ttcttgatca tgaaaacgcc        120
aacaaaattc tgaatcggcc aaagaggtat aattcaggta aattggaaga gtttgttcaa       180
gggaaccttg agagagaatg tatggaagaa aagtgtagtt ttgaagaagc acgagaagtt       240
tttgaaaaca ctgaaagaac aactgaattt tggaagcagt atgttgatgg agatcagtgt       300
gagtccaatc catgttttaa tggcggcagt tgcaaggatg acattaattc ctatgaatgt       360
tggtgtccct ttggatttga aggaaagaac tgtgaattag atgtaacatg taacattaag       420
aatggcagat gcgagcagtt ttgtaaaaat agtgctgata caaggtggt ttgctcctgt       480 actgagggat atcgacttgc agaaaaccag aagtcctgtg aaccagcagt gccatttcca       540
tgtggaagag tttctgtttc acaaacttct aagctcaccc gtgctgagac tgttttttcct       600 gatgtggact atgtaaattc tactgaagct gaaaccattt ggataacat cactcaaagc        660 acccaatcat ttaatgactt cactcgagtt gttggtggag aagatgccaa accaggtcaa       720
ttcccttggc aggttgtttt gaatggtaaa gttgatgcat tctgtggagg ctctatcgtt       780
aatgaaaaat ggattgtaac tgctgcccac tgtgttgaaa ctggtgttaa aattacagtt       840
```

```
gtcgcaggtg aacataatat tgaggagaca gaacatacag agcaaaagcg aaatgtgatt    900
cgaattattc ctcaccacaa ctacaatgca gctattaata agtacaacca tgacattgcc    960
cttctggaac tggacgaacc cttagtgcta acagctacg ttacacctat ttgcattgct   1020
gacaaggaat acacgaacat cttcctcaaa tttggatctg gctatgtaag tggctgggga   1080
agagtcttcc acaaagggag atcagcttta gttcttcagt accttagagt tccacttgtt   1140
gaccgagcca catgtcttcg atctacaaag ttcaccatct ataacaacat gttctgtgct   1200
ggcttccatg aaggaggtag agattcatgt caaggagata gtgggggacc ccatgttact   1260
gaagtggaag ggaccagttt cttaactgga attattagct ggggtgaaga gtgtgcaatg   1320
aaaggcaaat atggaatata taccaaggta tcccggtatg tcaactggat taaggaaaaa   1380
acaaagctca ctagctccag cagcaaggcc cctcccccga gcctgccctc cccaagcagg   1440
ctgcctgggc cctccgacac accaatcctg ccacagtgat gaaggtctgg atccgcggcc   1500
gc                                                                  1502

<210> SEQ ID NO 19
<211> LENGTH: 489
<212> TYPE: PRT
<213> ORGANISM: Homo sapiens

<400> SEQUENCE: 19

Met Gln Arg Val Asn Met Ile Met Ala Glu Ser Pro Gly Leu Ile Thr
1               5                   10                  15

Ile Cys Leu Leu Gly Tyr Leu Leu Ser Ala Glu Cys Thr Val Phe Leu
            20                  25                  30

Asp His Glu Asn Ala Asn Lys Ile Leu Asn Arg Pro Lys Arg Tyr Asn
        35                  40                  45

Ser Gly Lys Leu Glu Glu Phe Val Gln Gly Asn Leu Glu Arg Glu Cys
    50                  55                  60

Met Glu Glu Lys Cys Ser Phe Glu Glu Ala Arg Glu Val Phe Glu Asn
65                  70                  75                  80

Thr Glu Arg Thr Thr Glu Phe Trp Lys Gln Tyr Val Asp Gly Asp Gln
                85                  90                  95

Cys Glu Ser Asn Pro Cys Leu Asn Gly Gly Ser Cys Lys Asp Asp Ile
            100                 105                 110

Asn Ser Tyr Glu Cys Trp Cys Pro Phe Gly Phe Glu Gly Lys Asn Cys
        115                 120                 125

Glu Leu Asp Val Thr Cys Asn Ile Lys Asn Gly Arg Cys Glu Gln Phe
    130                 135                 140

Cys Lys Asn Ser Ala Asp Asn Lys Val Val Cys Ser Cys Thr Glu Gly
145                 150                 155                 160

Tyr Arg Leu Ala Glu Asn Gln Lys Ser Cys Glu Pro Ala Val Pro Phe
                165                 170                 175

Pro Cys Gly Arg Val Ser Val Ser Gln Thr Ser Lys Leu Thr Arg Ala
            180                 185                 190

Glu Thr Val Phe Pro Asp Val Asp Tyr Val Asn Ser Thr Glu Ala Glu
        195                 200                 205

Thr Ile Leu Asp Asn Ile Thr Gln Ser Thr Gln Ser Phe Asn Asp Phe
    210                 215                 220

Thr Arg Val Val Gly Gly Glu Asp Ala Lys Pro Gly Gln Phe Pro Trp
225                 230                 235                 240

Gln Val Val Leu Asn Gly Lys Val Asp Ala Phe Cys Gly Gly Ser Ile
                245                 250                 255
```

Val Asn Glu Lys Trp Ile Val Thr Ala Ala His Cys Val Glu Thr Gly
            260                 265                 270

Val Lys Ile Thr Val Val Ala Gly Glu His Asn Ile Glu Glu Thr Glu
        275                 280                 285

His Thr Glu Gln Lys Arg Asn Val Ile Arg Ile Pro His His Asn
    290                 295                 300

Tyr Asn Ala Ala Ile Asn Lys Tyr Asn His Asp Ile Ala Leu Leu Glu
305                 310                 315                 320

Leu Asp Glu Pro Leu Val Leu Asn Ser Tyr Val Thr Pro Ile Cys Ile
                325                 330                 335

Ala Asp Lys Glu Tyr Thr Asn Ile Phe Leu Lys Phe Gly Ser Gly Tyr
            340                 345                 350

Val Ser Gly Trp Gly Arg Val Phe His Lys Gly Arg Ser Ala Leu Val
        355                 360                 365

Leu Gln Tyr Leu Arg Val Pro Leu Val Asp Arg Ala Thr Cys Leu Arg
370                 375                 380

Ser Thr Lys Phe Thr Ile Tyr Asn Asn Met Phe Cys Ala Gly Phe His
385                 390                 395                 400

Glu Gly Gly Arg Asp Ser Cys Gln Gly Asp Ser Gly Gly Pro His Val
            405                 410                 415

Thr Glu Val Glu Gly Thr Ser Phe Leu Thr Gly Ile Ile Ser Trp Gly
        420                 425                 430

Glu Glu Cys Ala Met Lys Gly Lys Tyr Gly Ile Tyr Thr Lys Val Ser
435                 440                 445

Arg Tyr Val Asn Trp Ile Lys Glu Lys Thr Lys Leu Thr Ser Ser Ser
    450                 455                 460

Ser Lys Ala Pro Pro Pro Ser Leu Pro Ser Pro Ser Arg Leu Pro Gly
465                 470                 475                 480

Pro Ser Asp Thr Pro Ile Leu Pro Gln
            485

<210> SEQ ID NO 20
<211> LENGTH: 1585
<212> TYPE: DNA
<213> ORGANISM: Homo sapiens

<400> SEQUENCE: 20
gcgatcgcca tgcagcgcgt gaacatgatc atggcagaat caccaggcct catcaccatc    60
tgccttttag gatatctact cagtgctgaa tgtacagttt ttcttgatca tgaaaacgcc   120
aacaaaattc tgaatcggcc aaagaggtat aattcaggta aattggaaga gtttgttcaa   180
gggaaccttg agagagaatg tatggaagaa agtgtagttt tgaagaagc acgagaagtt   240 tttgaaaaca ctgaaagaac aactgaattt tggaagcagt atgttgatgg agatcagtgt   300
gagtccaatc catgttttaaa tggcggcagt tgcaaggatg acattaattc ctatgaatgt   360
tggtgtccct ttggatttga aggaaagaac tgtgaattag atgtaacatg taacattaag   420
aatggcagat gcgagcagtt ttgtaaaaat agtgctgata caaggtggt ttgctcctgt   480 actgagggat atcgacttgc agaaaaccag aagtcctgtg aaccagcagt gccatttcca   540
tgtggaagag tttctgtttc acaaacttct aagctcaccc gtgctgagac tgttttcct   600 gatgtggact atgtaaattc tactgaagct gaaaccattt tggataacat cactcaaagc   660
acccaatcat ttaatgactt cactcgagtt gttggtggag aagatgccaa accaggtcaa   720
ttcccttggc aggttgtttt gaatggtaaa gttgatgcat ctgtggaggc tctatcgtt   780

-continued

```
aatgaaaaat ggattgtaac tgctgcccac tgtgttgaaa ctggtgttaa aattacagtt    840
gtcgcaggtg aacataatat tgaggagaca gaacatacag agcaaaagcg aaatgtgatt    900
cgaattattc ctcaccacaa ctacaatgca gctattaata agtacaacca tgacattgcc    960
cttctggaac tggacgaacc cttagtgcta aacagctacg ttacacctat ttgcattgct   1020
acaaggaata cacgaacatc ttcctcaaat ttggatctgg ctatgtaagt ggctggggaa   1080
gagtcttcca caagggaga tcagctttag ttcttcagta ccttagagtt ccacttgttg   1140
accgagccac atgtcttcga tctacaaagt tcaccatcta taacaacatg ttctgtgctg   1200
gcttccatga aggaggtaga gattcatgtc aaggagatag tggggaccc catgttactg   1260 aagtggaagg gaccagtttc ttaactggaa ttattagctg gggtgaagag tgtgcaatga   1320
aaggcaaata tggaatatat accaaggtat cccggtatgt caactggatt aaggaaaaaa   1380
caaagctcac tagctccagc agcaaggccc ctccccgag cctgccctcc ccaagcaggc   1440
tgcctgggcc ctccgacaca ccaatcctgc cacagagcag ctcctctaag gcccctcctc   1500
catccctgcc atcccctcc cggctgcctg gcccctctga caccctatc ctgcctcagt   1560 gatgaaggtc tggatccgcg gccgc                                          1585
```

<210> SEQ ID NO 21
<211> LENGTH: 517
<212> TYPE: PRT
<213> ORGANISM: Homo sapiens

<400> SEQUENCE: 21

```
Met Gln Arg Val Asn Met Ile Met Ala Glu Ser Pro Gly Leu Ile Thr
1               5                   10                  15

Ile Cys Leu Leu Gly Tyr Leu Leu Ser Ala Glu Cys Thr Val Phe Leu
            20                  25                  30

Asp His Glu Asn Ala Asn Lys Ile Leu Asn Arg Pro Lys Arg Tyr Asn
        35                  40                  45

Ser Gly Lys Leu Glu Glu Phe Val Gln Gly Asn Leu Glu Arg Glu Cys
    50                  55                  60

Met Glu Glu Lys Cys Ser Phe Glu Glu Ala Arg Glu Val Phe Glu Asn
65                  70                  75                  80

Thr Glu Arg Thr Thr Glu Phe Trp Lys Gln Tyr Val Asp Gly Asp Gln
                85                  90                  95

Cys Glu Ser Asn Pro Cys Leu Asn Gly Gly Ser Cys Lys Asp Asp Ile
            100                 105                 110

Asn Ser Tyr Glu Cys Trp Cys Pro Phe Gly Phe Glu Gly Lys Asn Cys
        115                 120                 125

Glu Leu Asp Val Thr Cys Asn Ile Lys Asn Gly Arg Cys Glu Gln Phe
    130                 135                 140

Cys Lys Asn Ser Ala Asp Asn Lys Val Val Cys Ser Cys Thr Glu Gly
145                 150                 155                 160

Tyr Arg Leu Ala Glu Asn Gln Lys Ser Cys Glu Pro Ala Val Pro Phe
                165                 170                 175

Pro Cys Gly Arg Val Ser Val Ser Gln Thr Ser Lys Leu Thr Arg Ala
            180                 185                 190

Glu Thr Val Phe Pro Asp Val Asp Tyr Val Asn Ser Thr Glu Ala Glu
        195                 200                 205

Thr Ile Leu Asp Asn Ile Thr Gln Ser Thr Gln Ser Phe Asn Asp Phe
    210                 215                 220

Thr Arg Val Val Gly Gly Glu Asp Ala Lys Pro Gly Gln Phe Pro Trp
225                 230                 235                 240
```

```
Gln Val Val Leu Asn Gly Lys Val Asp Ala Phe Cys Gly Ser Ile
                245                 250                 255

Val Asn Glu Lys Trp Ile Val Thr Ala Ala His Cys Val Glu Thr Gly
            260                 265                 270

Val Lys Ile Thr Val Val Ala Gly Glu His Asn Ile Glu Thr Glu
            275                 280                 285

His Thr Glu Gln Lys Arg Asn Val Ile Arg Ile Pro His His Asn
290                 295                 300

Tyr Asn Ala Ala Ile Asn Lys Tyr Asn His Asp Ile Ala Leu Leu Glu
305                 310                 315                 320

Leu Asp Glu Pro Leu Val Leu Asn Ser Tyr Val Thr Pro Ile Cys Ile
                325                 330                 335

Ala Asp Lys Glu Tyr Thr Asn Ile Phe Leu Lys Phe Gly Ser Gly Tyr
            340                 345                 350

Val Ser Gly Trp Gly Arg Val Phe His Lys Gly Arg Ser Ala Leu Val
        355                 360                 365

Leu Gln Tyr Leu Arg Val Pro Leu Val Asp Arg Ala Thr Cys Leu Arg
    370                 375                 380

Ser Thr Lys Phe Thr Ile Tyr Asn Asn Met Phe Cys Ala Gly Phe His
385                 390                 395                 400

Glu Gly Gly Arg Asp Ser Cys Gln Gly Asp Ser Gly Gly Pro His Val
                405                 410                 415

Thr Glu Val Glu Gly Thr Ser Phe Leu Thr Gly Ile Ile Ser Trp Gly
            420                 425                 430

Glu Glu Cys Ala Met Lys Gly Lys Tyr Gly Ile Tyr Thr Lys Val Ser
        435                 440                 445

Arg Tyr Val Asn Trp Ile Lys Glu Lys Thr Lys Leu Thr Ser Ser Ser
    450                 455                 460

Ser Lys Ala Pro Pro Pro Ser Leu Pro Ser Pro Ser Arg Leu Pro Gly
465                 470                 475                 480

Pro Ser Asp Thr Pro Ile Leu Pro Gln Ser Ser Ser Lys Ala Pro
                485                 490                 495

Pro Pro Ser Leu Pro Ser Pro Ser Arg Leu Pro Gly Pro Ser Asp Thr
            500                 505                 510

Pro Ile Leu Pro Gln
        515

<210> SEQ ID NO 22
<211> LENGTH: 2413
<212> TYPE: DNA
<213> ORGANISM: Homo sapiens

<400> SEQUENCE: 22
tctagagtcg accccgccat ggagctgagg ccctggttgc tatgggtggt agcagcaaca      60
ggaaccttgg tcctgctagc agctgatgct cagggccaga aggtcttcac caacacgtgg     120
gctgtgcgca tccctggagg cccagcggtg gccaacagtg tggcacggaa gcatgggttc     180
ctcaacctgg gccagatctt cggggactat taccacttct ggcatcgagg agtgacgaag     240
cggtccctgt cgcctcaccg cccgcggcac agccggctgc agagggagcc tcaagtacag     300
tggctggaac agcaggtggc aaagcgacgg actaaacggg acgtgtacca ggagcccaca     360
gaccccaagt ttcctcagca gtggtacctg tctggtgtca ctcagcggga cctgaatgtg     420
aaggcggcct gggcgcaggg ctacacaggg cacggcattg tggtctccat tctggacgat     480
ggcatcgaga agaaccaccc ggacttggca ggcaattatg atcctgggc cagtttgat       540
```

```
gtcaatgacc aggaccctga cccccagcct cggtacacac agatgaatga caacaggcac    600
ggcacacggt gtgcggggga gtggctgcg gtggccaaca acggtgtctg tggtgtaggt    660
gtggcctaca acgcccgcat tggaggggtg cgcatgctgg atggcgaggt gacagatgca    720
gtggaggcac gctcgctggg cctgaacccc aaccacatcc acatctacag tgccagctgg    780
ggccccgagg atgacggcaa gacagtggat gggccagccc gcctcgccga ggaggccttc    840
ttccgtgggg ttagccaggg ccgagggggg ctgggctcca tctttgtctg ggcctcgggg    900
aacgggggcc gggaacatga cagctgcaac tgcgacggct acaccaacag tatctacacg    960
ctgtccatca gcagcgccac gcagtttggc aacgtgccgt ggtacagcga ggcctgctcg    1020
tccacactgg ccacgaccta cagcagtggc aaccagaatg agaagcagat cgtgacgact    1080
gacttgcggc agaagtgcac ggagtctcac acgggcacct cagcctctgc cccttagca    1140
gccggcatca ttgctctcac cctggaggcc aataagaacc tcacatggcg gacatgcaa    1200
cacctggtgg tacagacctc gaagccagcc cacctcaatg ccaacgactg gccaccaat    1260
ggtgtgggcc ggaaagtgag ccactcatat ggctacgggc ttttggacgc aggcgccatg    1320
gtggccctgg cccagaattg gaccacagtg cccccagc ggaagtgcat catcgacatc    1380
ctcaccgagc ccaaagacat cgggaaacgg ctcgaggtgc ggaagaccgt gaccgcgtgc    1440
ctgggcgagc caaccacat cactcggctg agcacgctc aggcgcggct caccctgtcc    1500
tataatcgcc gtggcgacct ggccatccac ctggtcagcc ccatgggcac ccgctccacc    1560
ctgctggcag ccaggccaca tgactactcc gcagatgggt ttaatgactg gcccttcatg    1620
acaactcatt cctgggatga ggatccctct ggcgagtggg tcctagagat tgaaaacacc    1680
agcgaagcca acaactatgg gacgctgacc aagttcaccc tcgtactcta tggcaccgcc    1740
cctgagggc tgcccgtacc tccagaaagc agtggctgca agaccctcac gtccagtcag    1800
gcctgtgtgg tgtgcgagga aggcttctcc ctgcaccaga gagctgtgt ccagcactgc    1860
cctccaggct tcgcccccca agtcctcgat acgcactata gcaccgagaa tgacgtggag    1920
accatccggg ccagcgtctg cgcccccgc cacgcctcat gtgccacatg ccaggggccg    1980
gccctgacag actgcctcag ctgccccagc cacgcctcct ggaccctgt ggagcagact    2040
tgctcccggc aaagccagag cagccgagag tccccgccac agcagcagcc acctcggctg    2100
cccccggagg tggaggcggg gcaacggctg cgggcagggc tgctgccctc acacctgcct    2160
gaggtggtgg ccggcctcag ctgcgccttc atcgtgctgg tcttcgtcac tgtcttcctg    2220
gtcctgcagc tgcgctctgg ctttagtttt cgggggtga aggtgtacac catggaccgt    2280
ggcctcatct cctacaaggg gctgccccct gaagcctggc aggaggagtg cccgtctgac    2340
tcagaagagg acgagggccg gggcgagagg accgccttta tcaaagacca gagcgccctc    2400
tgaacgcggc cgc                                                      2413
```

<210> SEQ ID NO 23
<211> LENGTH: 794
<212> TYPE: PRT
<213> ORGANISM: Homo sapiens

<400> SEQUENCE: 23

Met Glu Leu Arg Pro Trp Leu Leu Trp Val Val Ala Ala Thr Gly Thr
1               5                   10                  15

Leu Val Leu Leu Ala Ala Asp Ala Gln Gly Gln Lys Val Phe Thr Asn
            20                  25                  30

Thr Trp Ala Val Arg Ile Pro Gly Gly Pro Ala Val Ala Asn Ser Val

```
                    35                  40                  45
Ala Arg Lys His Gly Phe Leu Asn Leu Gly Gln Ile Phe Gly Asp Tyr
 50                  55                  60

Tyr His Phe Trp His Arg Gly Val Thr Lys Arg Ser Leu Ser Pro His
 65                  70                  75                  80

Arg Pro Arg His Ser Arg Leu Gln Arg Glu Pro Gln Val Gln Trp Leu
                 85                  90                  95

Glu Gln Gln Val Ala Lys Arg Arg Thr Lys Arg Asp Val Tyr Gln Glu
                100                 105                 110

Pro Thr Asp Pro Lys Phe Pro Gln Gln Trp Tyr Leu Ser Gly Val Thr
                115                 120                 125

Gln Arg Asp Leu Asn Val Lys Ala Ala Trp Ala Gln Gly Tyr Thr Gly
                130                 135                 140

His Gly Ile Val Val Ser Ile Leu Asp Asp Gly Ile Glu Lys Asn His
145                 150                 155                 160

Pro Asp Leu Ala Gly Asn Tyr Asp Pro Gly Ala Ser Phe Asp Val Asn
                165                 170                 175

Asp Gln Asp Pro Asp Pro Gln Pro Arg Tyr Thr Gln Met Asn Asp Asn
                180                 185                 190

Arg His Gly Thr Arg Cys Ala Gly Glu Val Ala Ala Val Ala Asn Asn
                195                 200                 205

Gly Val Cys Gly Val Gly Val Ala Tyr Asn Ala Arg Ile Gly Gly Val
210                 215                 220

Arg Met Leu Asp Gly Glu Val Thr Asp Ala Val Glu Ala Arg Ser Leu
225                 230                 235                 240

Gly Leu Asn Pro Asn His Ile His Ile Tyr Ser Ala Ser Trp Gly Pro
                245                 250                 255

Glu Asp Asp Gly Lys Thr Val Asp Gly Pro Ala Arg Leu Ala Glu Glu
                260                 265                 270

Ala Phe Phe Arg Gly Val Ser Gln Gly Arg Gly Gly Leu Gly Ser Ile
                275                 280                 285

Phe Val Trp Ala Ser Gly Asn Gly Gly Arg Glu His Asp Ser Cys Asn
290                 295                 300

Cys Asp Gly Tyr Thr Asn Ser Ile Tyr Thr Leu Ser Ile Ser Ser Ala
305                 310                 315                 320

Thr Gln Phe Gly Asn Val Pro Trp Tyr Ser Glu Ala Cys Ser Ser Thr
                325                 330                 335

Leu Ala Thr Thr Tyr Ser Ser Gly Asn Gln Asn Glu Lys Gln Ile Val
                340                 345                 350

Thr Thr Asp Leu Arg Gln Lys Cys Thr Glu Ser His Thr Gly Thr Ser
                355                 360                 365

Ala Ser Ala Pro Leu Ala Ala Gly Ile Ile Ala Leu Thr Leu Glu Ala
                370                 375                 380

Asn Lys Asn Leu Thr Trp Arg Asp Met Gln His Leu Val Val Gln Thr
385                 390                 395                 400

Ser Lys Pro Ala His Leu Asn Ala Asn Asp Trp Ala Thr Asn Gly Val
                405                 410                 415

Gly Arg Lys Val Ser His Ser Tyr Gly Tyr Gly Leu Leu Asp Ala Gly
                420                 425                 430

Ala Met Val Ala Leu Ala Gln Asn Trp Thr Thr Val Ala Pro Gln Arg
                435                 440                 445

Lys Cys Ile Ile Asp Ile Leu Thr Glu Pro Lys Asp Ile Gly Lys Arg
450                 455                 460
```

-continued

```
Leu Glu Val Arg Lys Thr Val Thr Ala Cys Leu Gly Glu Pro Asn His
465                 470                 475                 480

Ile Thr Arg Leu Glu His Ala Gln Ala Arg Leu Thr Leu Ser Tyr Asn
                485                 490                 495

Arg Arg Gly Asp Leu Ala Ile His Leu Val Ser Pro Met Gly Thr Arg
            500                 505                 510

Ser Thr Leu Leu Ala Ala Arg Pro His Asp Tyr Ser Ala Asp Gly Phe
        515                 520                 525

Asn Asp Trp Ala Phe Met Thr Thr His Ser Trp Asp Glu Asp Pro Ser
    530                 535                 540

Gly Glu Trp Val Leu Glu Ile Glu Asn Thr Ser Glu Ala Asn Asn Tyr
545                 550                 555                 560

Gly Thr Leu Thr Lys Phe Thr Leu Val Leu Tyr Gly Thr Ala Pro Glu
                565                 570                 575

Gly Leu Pro Val Pro Pro Glu Ser Ser Gly Cys Lys Thr Leu Thr Ser
            580                 585                 590

Ser Gln Ala Cys Val Val Cys Glu Glu Gly Phe Ser Leu His Gln Lys
        595                 600                 605

Ser Cys Val Gln His Cys Pro Pro Gly Phe Ala Pro Gln Val Leu Asp
    610                 615                 620

Thr His Tyr Ser Thr Glu Asn Asp Val Glu Thr Ile Arg Ala Ser Val
625                 630                 635                 640

Cys Ala Pro Cys His Ala Ser Cys Ala Thr Cys Gln Gly Pro Ala Leu
                645                 650                 655

Thr Asp Cys Leu Ser Cys Pro Ser His Ala Ser Leu Asp Pro Val Glu
            660                 665                 670

Gln Thr Cys Ser Arg Gln Ser Gln Ser Ser Arg Glu Ser Pro Pro Gln
        675                 680                 685

Gln Gln Pro Pro Arg Leu Pro Pro Glu Val Glu Ala Gly Gln Arg Leu
    690                 695                 700

Arg Ala Gly Leu Leu Pro Ser His Leu Pro Glu Val Val Ala Gly Leu
705                 710                 715                 720

Ser Cys Ala Phe Ile Val Leu Val Phe Val Thr Val Phe Leu Val Leu
                725                 730                 735

Gln Leu Arg Ser Gly Phe Ser Phe Arg Gly Val Lys Val Tyr Thr Met
            740                 745                 750

Asp Arg Gly Leu Ile Ser Tyr Lys Gly Leu Pro Pro Glu Ala Trp Gln
        755                 760                 765

Glu Glu Cys Pro Ser Asp Ser Glu Glu Asp Glu Gly Arg Gly Glu Arg
    770                 775                 780

Thr Ala Phe Ile Lys Asp Gln Ser Ala Leu
785                 790
```

US 8,476,234 B2

LONG-ACTING COAGULATION FACTORS AND METHODS OF PRODUCING SAME

CROSS REFERENCE TO RELATED APPLICATIONS

This Application claims priority from U.S. Provisional Application Ser. No. 61/224,366 filed Jul. 9, 2009, which are hereby incorporated in their entirety by reference herein.

FIELD OF INVENTION

Polypeptides and polynucleotides encoding same comprising at least one carboxy-terminal peptide (CTP) of chorionic gonadotrophin attached to a C-terminus (carboxy terminus) of a coagulation factor are disclosed. Pharmaceutical compositions comprising the polypeptide and polynucleotides of the invention and methods of using same are also disclosed.

BACKGROUND OF THE INVENTION

Polypeptides are susceptible to denaturation or enzymatic degradation in the blood, liver or kidney. Accordingly, polypeptides typically have short circulatory half-lives of several hours. Because of their low stability, peptide drugs are usually delivered in a sustained frequency so as to maintain an effective plasma concentration of the active peptide. Moreover, since peptide drugs are usually administrated by infusion, frequent injection of peptide drugs cause considerable discomfort to a subject. Thus, there is a need for technologies that will prolong the half-lives of therapeutic polypeptides while maintaining a high pharmacological efficacy thereof. Such desirous peptide drugs should also meet the requirements of enhanced serum stability, high activity and a low probability of inducing an undesired immune response when injected into a subject.

Unfavorable pharmacokinetics, such as a short serum half-life, can prevent the pharmaceutical development of many otherwise promising drug candidates. Serum half-life is an empirical characteristic of a molecule, and must be determined experimentally for each new potential drug. For example, with lower molecular weight polypeptide drugs, physiological clearance mechanisms such as renal filtration can make the maintenance of therapeutic levels of a drug unfeasible because of cost or frequency of the required dosing regimen. Conversely, a long serum half-life is undesirable where a drug or its metabolites have toxic side effects.

SUMMARY OF THE INVENTION

In one embodiment, the present invention provides a polypeptide consisting a coagulation factor and one to five gonadotrophin carboxy terminal (CTP) peptides attached to a carboxy terminus of the coagulation factor.

In another embodiment, the present invention further provides a polynucleotide molecule comprising a coding portion encoding a polypeptide consisting a coagulation factor and one to five gonadotrophin carboxy terminal peptides attached to a carboxy terminus of the coagulation factor.

In another embodiment, the present invention further provides a A method of extending a biological half life of a coagulation factor, comprising the step of attaching one to five chorionic gonadotrophin carboxy terminal peptides to a carboxy terminus of the coagulation factor, thereby improving a biological half life of a coagulation factor.

In another embodiment, the present invention further provides a method of improving the area under the curve (AUC) of a coagulation factor, comprising the step of attaching one to five chorionic gonadotrophin carboxy terminal peptides to a carboxy terminus of the coagulation factor, thereby improving the area under the curve (AUC) of a coagulation factor.

In another embodiment, the present invention further provides a method of reducing a dosing frequency of a coagulation factor, comprising the step of attaching one to five chorionic gonadotrophin carboxy terminal peptides to a carboxy terminus of the coagulation factor, thereby reducing a dosing frequency of a coagulation factor.

In another embodiment, the present invention further provides a method of increasing compliance in the use of coagulation factor therapy, comprising providing to a subject in need thereof, a polypeptide comprising a coagulation factor, one to five chorionic gonadotrophin carboxy terminal peptides attached to a carboxy terminus of the coagulation factor, thereby increasing compliance in the use of coagulation factor therapy.

DETAILED DESCRIPTION OF THE INVENTION

Figure 1:
FIG. 1 is a diagram illustrating rFVII-CTP construct (A), rFVII-CTP-CTP construct (B), rFIX-CTP construct (C), and rFIX-CTP-CTP construct (D).

In one embodiment, the present invention provides long-acting coagulation factors and methods of producing and using same. In another embodiment, long-acting coagulation factors comprise carboxy terminal peptide (CTP, also referred to as CTP unit). In another embodiment, long-acting polypeptides which comprise a coagulation factor further comprise carboxy terminal peptide (CTP) of human Chorionic Gonadotropin (hCG). In another embodiment, CTP acts as a protectant against degradation of coagulation factors. In another embodiment, CTP extends the C$_{max}$ of coagulation factors. In another embodiment, CTP extends the T$_{max}$ of coagulation factors. In another embodiment, CTP extends circulatory half-lives of coagulation factors. In some embodiments, CTP enhances the potency of coagulation factors.

In another embodiment, provided herein a method of extending a biological half life of a coagulation factor, comprising the step of attaching one to ten CTPs to a carboxy terminus of a coagulation factor, thereby improving a biological half life of a coagulation factor. In another embodiment, provided herein a method of extending a biological half life of a coagulation factor, comprising the step of attaching one to five CTPs to a carboxy terminus of a coagulation factor, thereby improving a biological half life of a coagulation factor.

In another embodiment, provided herein a method of improving the area under the curve (AUC) of a coagulation factor, comprising the step of attaching one to ten CTPs to a carboxy terminus of a coagulation factor, thereby improving the area under the curve (AUC) of a coagulation factor. In another embodiment, provided herein a method of improving the area under the curve (AUC) of a coagulation factor, comprising the step of attaching one to five CTPs to a carboxy terminus of a coagulation factor, thereby improving the area under the curve (AUC) of a coagulation factor.

In another embodiment, a coagulation factor of the invention is a protein. In another embodiment, a coagulation factor of the invention is a peptide. In another embodiment, a coagulation factor of the invention is a polypeptide. In another embodiment, the coagulation factor is an enzyme. In another embodiment, the coagulation factor is a serine protease. In another embodiment, the coagulation factor is a glycoprotein. In another embodiment, the coagulation factor is a transglutaminase. In another embodiment, the coagulation factor is an inactive zymogen. In another embodiment, the coagulation factor is any coagulation factor known to one of skill in the art. In another embodiment, the coagulation factor is FVIII. In another embodiment, the coagulation factor is FV. In another embodiment, the coagulation factor is Factor XIII. In another embodiment, the coagulation factor is factor X. In another embodiment, the coagulation factor is thrombin. In another embodiment, the coagulation factor is fibrin. In another embodiment, the coagulation factor is FVIIa. In another embodiment, the coagulation factor is FVII. In another embodiment, the coagulation factor is FIX. In another embodiment, the coagulation factor is FX. In another embodiment, the coagulation factor is FXIa. In another embodiment, the coagulation factor is FXII. In another embodiment, the coagulation factor is FXa. In another embodiment, the coagulation factor is FVa. In another embodiment, the coagulation factor is prothrombin. In another embodiment, the coagulation factor is thrombin. In another embodiment, the coagulation factor is FV. In another embodiment, the coagulation factor is FXI. In another embodiment, the coagulation factor is vWF. In another embodiment, the coagulation factor is FVIIIa. In another embodiment, the coagulation factor is B-deleted Domain FVIII (FVIIIBDD). In another embodiment, the coagulation factor is FIXa. In another embodiment, the coagulation factor is prekallikrein. In another embodiment, the coagulation factor is kallikrein. In another embodiment, the coagulation factor is FXIIa. In another embodiment, the coagulation factor is fibrinogen. In another embodiment, the coagulation factor is thrombomodulin. In another embodiment, the coagulation factor is FII.

In another embodiment, the coagulation factor is a glycoprotein. In another embodiment, the coagulation factor is a vitamin K dependent glycoprotein. In another embodiment, the coagulation factor is a vitamin K independent glycoprotein. In another embodiment, the coagulation factor is a recombinant protein. In another embodiment, the coagulation factor is a recombinant glycoprotein. In another embodiment, the coagulation factor is a recombinant glycoprotein FV. In another embodiment, the coagulation factor is a recombinant FVI. In another embodiment, the coagulation factor is a recombinant FVII. In another embodiment, the coagulation factor is a recombinant FVIII. In another embodiment, the coagulation factor is a recombinant FIX. In another embodiment, the coagulation factor is a recombinant FX. In another embodiment, the coagulation factor is a recombinant FXI. In another embodiment, the coagulation factor is a recombinant FXII. In another embodiment, the coagulation factor is a recombinant FvW. In another embodiment, the coagulation factor is a recombinant FII. In another embodiment, the coagulation factor is a recombinant FIXa. In another embodiment, the coagulation factor is a recombinant FXIa. In another embodiment, the coagulation factor is a recombinant fibrin. In another embodiment, the coagulation factor is a recombinant FVIIa. In another embodiment, the coagulation factor is a recombinant FXa. In another embodiment, the coagulation factor is a recombinant FVa. In another embodiment, the coagulation factor is a recombinant prothrombin. In another embodiment, the coagulation factor is a recombinant thrombin. In another embodiment, the coagulation factor is a recombinant FVIIIa. In another embodiment, the coagulation factor is a recombinant prekallikrein. In another embodiment, the coagulation factor is a recombinant kallikrein. In another embodiment, the coagulation factor is a recombinant FXIIa. In another embodiment, the coagulation factor is any known recombinant coagulation factor. In another embodiment, the coagulation factor comprising a signal peptide is any known recombinant coagulation factor. In another embodiment, a coagulation factor comprises 1-10 CTP repeats attached to the C-terminus and no CTPs attached to the N-terminus. In another embodiment, the coagulation factor comprising a signal peptide is any known recombinant coagulation factor. In another embodiment, a coagulation factor comprises at least one CTP attached to the C-terminus and no CTPs attached to the N-terminus. In another embodiment, a coagulation factor comprising 1-10 CTP repeats attached to the C-terminus and no CTPs attached to the N-terminus is an engineered coagulation factor. In another embodiment, a coagulation factor comprising at least one CTP attached to the C-terminus and no CTPs attached to the N-terminus is an engineered coagulation factor. In another embodiment, a coagulation factor comprising 1-10 CTP repeats attached to the C-terminus and no CTPs attached to the N-terminus is a conjugated coagulation factor. In another embodiment, a coagulation factor comprising at least one CTP attached to the C-terminus and no CTPs attached to the N-terminus is a conjugated coagulation factor.

In another embodiment, the coagulation factor comprising a domain organization similar or identical to the domain organization of FIX, FVII, factor X, protein C and prothrombin. In another embodiment, the coagulation factor is synthesized as precursors with N-terminal propeptide. In another embodiment, the coagulation factor as used herein is in an inactive pro-enzyme form. In another embodiment, the coagulation factor is produces in hepatocytes. In another embodiment, the coagulation factor comprises a docking site for gammacarboxylase which converts glutamic acids (Glu) into gamma carboxy glutamic acids (Gla). In another embodiment, the coagulation factor as used herein is a commercially available coagulation factor.

In another embodiment, the amino acid sequence of factor VII comprises the following amino acid sequence:

```
                                              (SEQ ID NO: 9)
MVSQALRLLCLLLGLQGCLAAVFVTQEEAHGVLHRRRRANAFLEELRP

GSLERECKEEQCSFEEAREIFKDAERTKLFWISYSDGDQCASSPCQNG

GSCKDQLQSYICFCLPAFEGRNCETHKDDQLICVNENGGCEQYCSDHT

GTKRSCRCHEGYSLLADGVSCTPTVEYPCGKIPILEKRNASKPQGRIVGG

KVCPKGECPWQVLLLVNGAQLCGGTLINTIWVVSAAHCFDKIKNWRNLIA

VLGEHDLSEHDGDEQSRRVAQVIIPSTYVPGTTNHDIALLRLHQPVVLT

DHVVPLCLPERTFSERTLAFVRFSLVSGWGQLLDRGATALELMVLNV

PRLMTQDCLQQSRKVGDSPNITEYMFCAGYSDGSKDSCKGDSGGPH

ATHYRGTWYLTGIVSWGQGCATVGHFGVYTRVSQYIEWLQKLMRSEPR

PGVLLRAPFP.
```

In another embodiment, the amino acid sequence of factor VII comprises the following amino acid sequence:

```
                                             (SEQ ID NO: 10)
MVSQALRLLCLLLGLQGCLAAVFVTQEEAHGVLHRRRRANAFLEELRP

GSLERECKEEQCSFEEAREIFKDAERTKLFWISYSDGDQCASSPCQN

GGSCKDQLQSYICFCLPAFEGRNCETHKDDQLICVNENGGCEQYCSDH

TGTKRSCRCHEGYSLLADGVSCTPTVEYPCGKIPILEKRNASKPQGRIV

GGKVCPKGECPWQVLLLVNGAQLCGGTLINTIWVVSAAHCFDKIKNWR

NLIAVLGEHDLSEHDGDEQSRRVAQVIIPSTYVPGTTNHDIALLRLHQP

VVLTDHVVPLCLPERTFSERTLAFVRFSLVSGWGQLLDRGATALELMV

LNVPRLMTQDCLQQSRKVGDSPNITEYMFCAGYSDGSKDSCKGDSGG

PHATHYRGTWYLTGIVSWGQGCATVGHFGVYTRVSQYIEWLQKLMRSE

PRPGVLLRAPFP*GCGR.
```

In another embodiment, the nucleic acid sequence encoding factor VII comprises the nucleic acid sequence:

```
                                             (SEQ ID NO: 11)
CTCGAGGACATGGTCTCCCAGGCCCTCAGGCTCCTCTGCCTTCTGCTTGGGCTTCA

GGGCTGCCTGGCTGCAGTCTTCGTAACCCAGGAGGAAGCCCACGGCGTCCTGCA

CCGGCGCCGGCGCGCCAACGCGTTCCTGGAGGAGCTGCGGCGGGCTCCCTGGA

GAGGGAGTGCAAGGAGGAGCAGTGCTCCTTCGAGGAGGCCCGGGAGATCTTCAA

GGACGCGGAGAGGACGAAGCTGTTCTGGATTTCTTACAGTGATGGGGACCAGTG

TGCCTCAAGTCCATGCCAGAATGGGGCTCCTGCAAGGACCAGCTCCAGTCCTAT

ATCTGCTTCTGCCTCCCTGCCTTCGAGGGCCGGAACTGTGAGACGCACAAGGATG

ACCAGCTGATCTGTGTGAACGAGAACGGCGGCTGTGAGCAGTACTGCAGTGACC

ACACGGGCACCAAGCGCTCCTGTCGGTGCCACGAGGGGTACTCTCTGCTGGCAG

ACGGGGTGTCCTGCACACCCACAGTTGAATATCCATGTGGAAAAATACCTATTCT

AGAAAAAAGAAATGCCAGCAAACCCCAAGGCCGAATTGTGGGGGGCAAGGTGT

GCCCCAAAGGGGAGTGTCCATGGCAGGTCCTGTTGTTGGTGAATGGAGCTCAGTT

GTGTGGGGGACCCTGATCAACACCATCTGGGTGGTCTCCGCGGCCCACTGTTTC

GACAAAATCAAGAACTGGAGGAACCTGATCGCGGTGCTGGGCGAGCACGACCTC
```

```
-continued
AGCGAGCACGACGGGGATGAGCAGAGCCGGCGGGTGGCGCAGGTCATCATCCCC

AGCACGTACGTCCCGGGCACCACCAACCACGACATCGCGCTGCTCCGCCTGCACC

AGCCCGTGGTCCTCACTGACCATGTGGTGCCCCTCTGCCTGCCCGAACGGACGTT

CTCTGAGAGGACGCTGGCCTTCGTGCGCTTCTCATTGGTCAGCGGCTGGGGCCAG

CTGCTGGACCGTGGCGCCACGGCCCTGGAGCTCATGGTCCTCAACGTGCCCCGGC

TGATGACCCAGGACTGCCTGCAGCAGTCACGGAAGGTGGGAGACTCCCCAAATA

TCACGGAGTACATGTTCTGTGCCGGCTACTCGGATGGCAGCAAGGACTCCTGCAA

GGGGGACAGTGGAGGCCCACATGCCACCCACTACCGGGGCACGTGGTACCTGAC

GGGCATCGTCAGCTGGGGCCAGGGCTGCGCAACCGTGGGCCACTTTGGGGTGTA

CACCAGGGTCTCCCAGTACATCGAGTGGCTGCAAAAGCTCATGCGCTCAGAGCC

ACGCCCAGGAGTCCTCCTGCGAGCCCCATTTCCCTGAGGATGCGGCCGC.
```

In another embodiment, the nucleic acid sequence encoding factor VII-CTP (attached to the carboxy terminus) comprises the following nucleic acid sequence:

```
                                          (SEQ ID NO: 12)
CTCGAGGACATGGTCTCCCAGGCCCTCAGGCTCCTCTGCCTTCTGCTTGGGCTTCA

GGGCTGCCTGGCTGCAGTCTTCGTAACCCAGGAGGAAGCCCACGGCGTCCTGCA

CCGGCGCCGGCGCGCCAACGCGTTCCTGGAGGAGCTGCGGCCGGGCTCCCTGGA

GAGGGAGTGCAAGGAGGAGCAGTGCTCCTTCGAGGAGGCCCGGGAGATCTTCAA

GGACGCGGAGAGGACGAAGCTGTTCTGGATTTCTTACAGTGATGGGGACCAGTG

TGCCTCAAGTCCATGCCAGAATGGGGCTCCTGCAAGGACCAGCTCCAGTCCTAT

ATCTGCTTCTGCCTCCCTGCCTTCGAGGGCCGGAACTGTGAGACGCACAAGGATG

ACCAGCTGATCTGTGTGAACGAGAACGGCGGCTGTGAGCAGTACTGCAGTGACC

ACACGGGCACCAAGCGCTCCTGTCGGTGCCACGAGGGGTACTCTCTGCTGGCAG

ACGGGGTGTCCTGCACACCCACAGTTGAATATCCATGTGGAAAAATACCTATTCT

AGAAAAAAGAAATGCCAGCAAACCCCAAGGCCGAATTGTGGGGGGCAAGGTGT

GCCCCAAAGGGGAGTGTCCATGGCAGGTCCTGTTGTTGGTGAATGGAGCTCAGTT

GTGTGGGGGACCCTGATCAACACCATCTGGGTGGTCTCCGCGGCCCACTGTTTC

GACAAAATCAAGAACTGGAGGAACCTGATCGCGGTGCTGGGCGAGCACGACCTC

AGCGAGCACGACGGGGATGAGCAGAGCCGGCGGGTGGCGCAGGTCATCATCCCC

AGCACGTACGTCCCGGGCACCACCAACCACGACATCGCGCTGCTCCGCCTGCACC

AGCCCGTGGTCCTCACTGACCATGTGGTGCCCCTCTGCCTGCCCGAACGGACGTT

CTCTGAGAGGACGCTGGCCTTCGTGCGCTTCTCATTGGTCAGCGGCTGGGGCCAG

CTGCTGGACCGTGGCGCCACGGCCCTGGAGCTCATGGTCCTCAACGTGCCCCGGC

TGATGACCCAGGACTGCCTGCAGCAGTCACGGAAGGTGGGAGACTCCCCAAATA

TCACGGAGTACATGTTCTGTGCCGGCTACTCGGATGGCAGCAAGGACTCCTGCAA

GGGGGACAGTGGAGGCCCACATGCCACCCACTACCGGGGCACGTGGTACC

TGACCGGCATCGTGAGCTGGGGCCAGGGCTGCGCCACCGTGGGCCACTTCGGCG

TGTACACCAGGGTGTCCCAGTACATCGAGTGGCTGCAGAAACTGATGAGAAGCG

AGCCCAGACCCGGCGTGCTGCTGAGAGCCCCCTTCCCCAGCAGCAGCTCCAAGG

CCCCTCCCCCTAGCCTGCCCAGCCCTAGCAGACTGCCTGGGCCCAGCGACACCCC
```

CATCCTGCCCCAGTGAGGATCCGCGGCCGC.

In another embodiment, the amino acid sequence of factor VII-CTP (attached to the carboxy terminus) comprises the following amino acid sequence:

(SEQ ID NO: 13)
MVSQALRLLCLLLGLQGCLAAVFVTQEEAHGVLHRRRRANAFLEELRP

GSLERECKEEQCSFEEAREIFKDAERTKLFWISYSDGDQCASSPCQN

GGSCKDQLQSYICFCLPAFEGRNCETHKDDQLICVNENGGCEQYCSDH

TGTKRSCRCHEGYSLLADGVSCTPTVEYPCGKIPILEKRNASKPQGRIV

-continued
GGKVCPKGECPWQVLLLVNGAQLCGGTLINTIWVVSAAHCFDKIKNWR

NLIAVLGEHDLSEHDGDEQSRRVAQVIIPSTYVPGTTNHDIALLRLHQP

VVLTDHVVPLCLPERTFSERTLAFVRFSLVSGWGQLLDRGATALELM

VLNVPRLMTQDCLQQSRKVGDSPNITEYMFCAGYSDGSKDSCKGDS

GGPHATHYRGTWYLTGIVSWGQGCATVGHFGVYTRVSQYIEWLQKLM

RSEPRPGVLLRAPFPSSSSKAPPPSLPSPSRLPGPSDTPILPQ*.

In another embodiment, the nucleic acid sequence encoding factor VII-CTP-CTP (attached to the carboxy terminus) comprises the following nucleic acid sequence:

(SEQ ID NO: 14)
CTCGAGGACATGGTCTCCCAGGCCCTCAGGCTCCTCTGCCTTCTGCTTGGGCTTCA

GGGCTGCCTGGCTGCAGTCTTCGTAACCCAGGAGGAAGCCCACGGCGTCCTGCA

CCGGCGCCGGCGCGCCAACGCGTTCCTGGAGGAGCTGCGGCCGGGCTCCCTGGA

GAGGGAGTGCAAGGAGGAGCAGTGCTCCTTCGAGGAGGCCCGGGAGATCTTCAA

GGACGCGGAGAGGACGAAGCTGTTCTGGATTTCTTACAGTGATGGGGACCAGTG

TGCCTCAAGTCCATGCCAGAATGGGGCTCCTGCAAGGACCAGCTCCAGTCCTAT

ATCTGCTTCTGCCTCCCTGCCTTCGAGGGCCGGAACTGTGAGACGCACAAGGATG

ACCAGCTGATCTGTGTGAACGAGAACGGCGGCTGTGAGCAGTACTGCAGTGACC

ACACGGGCACCAAGCGCTCCTGTCGGTGCCACGAGGGGTACTCTCTGCTGGCAG

ACGGGGTGTCCTGCACACCCACAGTTGAATATCCATGTGGAAAAATACCTATTCT

AGAAAAAAGAAATGCCAGCAAACCCCAAGGCCGAATTGTGGGGGGCAAGGTGT

GCCCCAAAGGGGAGTGTCCATGGCAGGTCCTGTTGTTGGTGAATGGAGCTCAGTT

GTGTGGGGGGACCCTGATCAACACCATCTGGGTGGTCTCCGCGGCCCACTGTTTC

GACAAAATCAAGAACTGGAGGAACCTGATCGCGGTGCTGGGCGAGCACGACCTC

AGCGAGCACGACGGGGATGAGCAGAGCCGGCGGGTGGCGCAGGTCATCATCCCC

AGCACGTACGTCCCGGGCACCACCAACCACGACATCGCGCTGCTCCGCCTGCACC

AGCCCGTGGTCCTCACTGACCATGTGGTGCCCCTCTGCCTGCCCGAACGGACGTT

CTCTGAGAGGACGCTGGCCTTCGTGCGCTTCTCATTGGTCAGCGGCTGGGGCCAG

CTGCTGGACCGTGGCGCCACGGCCCTGGAGCTCATGGTCCTCAACGTGCCCCGGC

TGATGACCCAGGACTGCCTGCAGCAGTCACGGAAGGTGGGAGACTCCCCAAATA

TCACGGAGTACATGTTCTGTGCCGGCTACTCGGATGGCAGCAAGGACTCCTGCAA

GGGGGACAGTGGAGGCCCACATGCCACCCACTACCGGGGCACGTGGTACCTGAC

CGGCATCGTGAGCTGGGGCCAGGGCTGCGCCACCGTGGGCCACTTCGGCGTGTA

CACCAGGGTGTCCCAGTACATCGAGTGGCTGCAGAAACTGATGAGAAGCGAGCC

CAGACCCGGCGTGCTGCTGAGAGCCCCCTTCCCCAGCAGCAGCTCCAAGGCCCCT

CCCCCTAGCCTGCCCAGCCCTAGCAGACTGCCTGGGCCCTCCGACACACCAATCC

TGCCACAGAGCAGCTCCTCTAAGGCCCCTCCTCCATCCCTGCCATCCCCCTCCCG

GCTGCCAGGCCCCTCTGACACCCCTATCCTGCCTCAGTGATGAAGGTCTGGATCC

GCGGCCGC.

In another embodiment, the amino acid sequence of factor VII-CTP-CTP (attached to the carboxy terminus) comprises the following amino acid sequence:

(SEQ ID NO: 15)
MVSQALRLLCLLLGLQGCLAAVFVTQEEAHGVLHRRRRANAFLEELRP

GSLERECKEEQCSFEEAREIFKDAERTKLFWISYSDGDQCASSPCQN

GGSCKDQLQSYICFCLPAFEGRNCETHKDDQLICVNENGGCEQYCSD

HTGTKRSCRCHEGYSLLADGVSCTPTVEYPCGKIPILEKRNASKPQGRI

VGGKVCPKGECPWQVLLLVNGAQLCGGTLINTIWVVSAAHCFDKIKNW

RNLIAVLGEHDLSEHDGDEQSRRVAQVIIPSTYVPGTTNHDIALLRLHQP

VVLTDHVVPLCLPERTFSERTLAFVRFSLVSGWGQLLDRGATALELMVL

NVPRLMTQDCLQQSRKVGDSPNITEYMFCAGYSDGSKDSCKGDSGGP

HATHYRGTWYLTGIVSWGQGCATVGHFGVYTRVSQYIEWLQKLMRSEPR

PGVLLRAPFPSSSSKAPPPSLPSPSRLPGPSDTPILPQSSSSKAPPPSL

PSPSRLPGPSDTPILPQ**.

In another embodiment, the nucleic acid sequence encoding factor IX comprises the following nucleic acid sequence:

(SEQ ID NO: 16)
GCGATCGCCATGCAGCGCGTGAACATGATCATGGCAGAATCACCAGGCCTCATC

ACCATTGCCTTTTAGGATATCTACTCAGTGCTGAATGTACAGTTTTTCTTGATCAT

GAAAACGCCAACAAAATTCTGAATCGGCCAAAGAGGTATAATTCAGGTAAATTG

GAAGAGTTTGTTCAAGGGAACCTTGAGAGAGAATGTATGGAAGAAAAGTGTAGT

TTTGAAGAAGCACGAGAAGTTTTTGAAAACACTGAAAGAACAACTGAATTTTGG

AAGCAGTATGTTGATGGAGATCAGTGTGAGTCCAATCCATGTTTAAATGGCGGCA

GTTGCAAGGATGACATTAATTCCTATGAATGTTGGTGTCCCTTTGGATTTGAAGG

AAAGAACTGTGAATTAGATGTAACATGTAACATTAAGAATGGCAGATGCGAGCA

GTTTTGTAAAAATAGTGCTGATAACAAGGTGGTTTGCTCCTGTACTGAGGGATAT

CGACTTGCAGAAAACCAGAAGTCCTGTGAACCAGCAGTGCCATTTCCATGTGGA

AGAGTTTCTGTTTCACAAACTTCTAAGCTCACCCGTGCTGAGACTGTTTTTCCTGA

TGTGGACTATGTAAATTCTACTGAAGCTGAAACCATTTTGGATAACATCACTCAA

AGCACCCAATCATTTAATGACTTCACTCGAGTTGTTGGTGGAGAAGATGCCAAAC

CAGGTCAATTCCCTTGGCAGGTTGTTTTGAATGGTAAAGTTGATGCATTCTGTGG

AGGCTCTATCGTTAATGAAAAATGGATTGTAACTGCTGCCCACTGTGTTGAAACT

GGTGTTAAAATTACAGTTGTCGCAGGTGAACATAATATTGAGGAGACAGAACAT

ACAGAGCAAAAGCGAAATGTGATTCGAATTATTCCTCACCACAACTACAATGCA

GCTATTAATAAGTACAACCATGACATTGCCCTTCTGGAACTGGACGAACCCTTAG

TGCTAAACAGCTACGTTACACCTATTTGCATTGCTGACAAGGAATACACGAACAT

CTTCCTCAAATTTGGATCTGGCTATGTAAGTGGCTGGGGAAGAGTCTTCCACAAA

GGGAGATCAGCTTTAGTTCTCCAGTACCTTAGAGTTCCACTTGTTGACCGAGCCA

CATGTCTTCGATCTACAAAGTTCACCATCTATAACAACATGTTCTGTGCTGGCTTC

CATGAAGGAGGTAGAGATTCATGTCAAGGAGATAGTGGGGGACCCCATGTTACT

GAAGTGGAAGGGACCAGTTTCTTAACTGGAATTATTAGCTGGGGTGAAGAGTGT

GCAATGAAAGGCAAATATGGAATATATACCAAGGTATCCCGGTATGTCAACTGG

ATTAAGGAAAAAACAAAGCTCACTTGAACGCGGCCGC.

In another embodiment, the amino acid sequence of factor IX comprises the following amino acid sequence:

(SEQ ID NO: 17)
MQRVNMIMAESPGLITICLLGYLLSAECTVFLDHENANKILNRPKRYNS

GKLEEFVQGNLERECMEEKCSFEEAREVFENTERTTEFWKQYVDGD

QCESNPCLNGGSCKDDINSYECWCPFGFEGKNCELDVTCNIKNGRC

EQFCKNSADNKVVCSCTEGYRLAENQKSCEPAVPFPCGRVSVSQTS

KLTRAETVFPDVDYVNSTEAETILDNITQSTQSFNDFTRVVGGEDAKPG

QFPWQVVLNGKVDAFCGGSIVNEKWIVTAAHCVETGVKITVVAGEHNI

EETEHTEQKRNVIRIIPHHNYNAAINKYNHDIALLELDEPLVLNSYVTPI

CIADKEYTNIFLKFGSGYVSGWGRVFHKGRSALVLQYLRVPLVDRATC

LRSTKFTIYNNMFCAGFHEGGRDSCQGDSGGPHVTEVEGTSFLTGIIS

WGEECAMKGKYGIYTKVSRYVNWIKEKTKLT*.

In another embodiment, the nucleic acid sequence encoding factor IX-CTP (attached to the carboxy terminus) comprises the following nucleic acid sequence:

(SEQ ID NO: 18)
GCGATCGCCATGCAGCGCGTGAACATGATCATGGCAGAATCACCAGGCCTCATC

ACCATCTGCCTTTTAGGATATCTACTCAGTGCTGAATGTACAGTTTTTCTTGATCA

TGAAAACGCCAACAAAATTCTGAATCGGCCAAAGAGGTATAATTCAGGTAAATT

GGAAGAGTTTGTTCAAGGGAACCTTGAGAGAGAATGTATGGAAGAAAAGTGTAG

TTTTGAAGAAGCACGAGAAGTTTTTGAAAACACTGAAAGAACAACTGAATTTTG

GAAGCAGTATGTTGATGGAGATCAGTGTGAGTCCAATCCATGTTTAAATGGCGGC

AGTTGCAAGGATGACATTAATTCCTATGAATGTTGGTGTCCCTTTGGATTTGAAG

GAAAGAACTGTGAATTAGATGTAACATGTAACATTAAGAATGGCAGATGCGAGC

AGTTTTGTAAAAATAGTGCTGATAACAAGGTGGTTTGCTCCTGTACTGAGGGATA

TCGACTTGCAGAAAACCAGAAGTCCTGTGAACCAGCAGTGCCATTTCCATGTGGA

AGAGTTTCTGTTTCACAAACTTCTAAGCTCACCCGTGCTGAGACTGTTTTTCCTGA

TGTGGACTATGTAAATTCTACTGAAGCTGAAACCATTTTGGATAACATCACTCAA

AGCACCCAATCATTTAATGACTTCACTCGAGTTGTTGGTGGAGAAGATGCCAAAC

CAGGTCAATTCCCTTGGCAGGTTGTTTTGAATGGTAAAGTTGATGCATTCTGTGG

AGGCTCTATCGTTAATGAAAAATGGATTGTAACTGCTGCCCACTGTGTTGAAACT

GGTGTTAAAATTACAGTTGTCGCAGGTGAACATAATATTGAGGAGACAGAACAT

ACAGAGCAAAAGCGAAATGTGATTCGAATTATTCCTCACCACAACTACAATGCA

GCTATTAATAAGTACAACCATGACATTGCCCTTCTGGAACTGGACGAACCCTTAG

TGCTAAACAGCTACGTTACACCTATTTGCATTGCTGACAAGGAATACACGAACAT

CTTCCTCAAATTTGGATCTGGCTATGTAAGTGGCTGGGGAAGAGTCTTCCACAAA

GGGAGATCAGCTTTAGTTCTTCAGTACCTTAGAGTTCCACTTGTTGACCGAGCCA

CATGTCTTCGATCTACAAAGTTCACCATCTATAACAACATGTTCTGTGCTGGCTTC

CATGAAGGAGGTAGAGATTCATGTCAAGGAGATAGTGGGGGACCCCATGTTACT

GAAGTGGAAGGGACCAGTTTCTTAACTGGAATTATTAGCTGGGGTGAAGAGTGT

GCAATGAAAGGCAAATATGGAATATATACCAAGGTATCCCGGTATGTCAACTGG

ATTAAGGAAAAAACAAAGCTCACTAGCTCCAGCAGCAAGGCCCCTCCCCCGAGC

CTGCCCTCCCCAAGCAGGCTGCCTGGGCCCTCCGACACACCAATCCTGCCACAGT

GATGAAGGTCTGGATCCGCGGCCGC.

In another embodiment, the amino acid sequence of factor IX-CTP (attached to the carboxy terminus) comprises the following amino acid sequence:

(SEQ ID NO: 19)
MQRVNMIMAESPGLITICLLGYLLSAECTVFLDHENANKILNRPKRYNS

GKLEEFVQGNLERECMEEKCSFEEAREVFENTERTTEFWKQYVDG

DQCESNPCLNGGSCKDDINSYECWCPFGFEGKNCELDVTCNIKNGR

CEQFCKNSADNKVVCSCTEGYRLAENQKSCEPAVPFPCGRVSVSQ

TSKLTRAETVFPDVDYVNSTEAETILDNITQSTQSFNDFTRVVGGEDA

KPGQFPWQVVLNGKVDAFCGGSIVNEKWIVTAAHCVETGVKITVVAG

EHNIEETEHTEQKRNVIRIIPHHNYNAAINKYNHDIALLELDEPLVLNSY

VTPICIADKEYTNIFLKFGSGYVSGWGRVFHKGRSALVLQYLRVPLV

DRATCLRSTKFTIYNNMFCAGFHEGGRDSCQGDSGGPHVTEVEGTS

FLTGIISWGEECAMKGKYGIYTKVSRYVNWIKEKTKLTSSSSKAPPPSL

PSPSRLPGPSDTPILPQ**.

In another embodiment, the nucleic acid sequence encoding factor IX-CTP-CTP (attached to the carboxy terminus) comprises the following nucleic acid sequence:

(SEQ ID NO: 20)
GCGATCGCCATGCAGCGCGTGAACATGATCATGGCAGAATCACCAGGCCTCATC

ACCATCTGCCTTTTAGGATATCTACTCAGTGCTGAATGTACAGTTTTTCTTGATCA

TGAAAACGCCAACAAAATTCTGAATCGGCCAAAGAGGTATAATTCAGGTAAATT

GGAAGAGTTTGTTCAAGGGAACCTTGAGAGAGAATGTATGGAAGAAAAGTGTAG

TTTTGAAGAAGCACGAGAAGTTTTTGAAAACACTGAAAGAACAACTGAATTTTG

GAAGCAGTATGTTGATGGAGATCAGTGTGAGTCCAATCCATGTTTAAATGGCGGC

AGTTGCAAGGATGACATTAATTCCTATGAATGTTGGTGTCCCTTTGGATTTGAAG

GAAAGAACTGTGAATTAGATGTAACATGTAACATTAAGAATGGCAGATGCGAGC

AGTTTTGTAAAAATAGTGCTGATAACAAGGTGGTTTGCTCCTGTACTGAGGGATA

TCGACTTGCAGAAAACCAGAAGTCCTGTGAACCAGCAGTGCCATTTCCATGTGGA

AGAGTTTCTGTTTCACAAACTTCTAAGCTCACCCGTGCTGAGACTGTTTTTCCTGA

TGTGGACTATGTAAATTCTACTGAAGCTGAAACCATTTTGGATAACATCACTCAA

AGCACCCAATCATTTAATGACTTCACTCGAGTTGTTGGTGGAGAAGATGCCAAAC

CAGGTCAATTCCCTTGGCAGGTTGTTTTGAATGGTAAAGTTGATGCATTCTGTGG

AGGCTCTATCGTTAATGAAAAATGGATTGTAACTGCTGCCCACTGTGTTGAAACT

GGTGTTAAAATTACAGTTGTCGCAGGTGAACATAATATTGAGGAGACAGAACAT

ACAGAGCAAAAGCGAAATGTGATTCGAATTATTCCTCACCACAACTACAATGCA

GCTATTAATAAGTACAACCATGACATTGCCCTTCTGGAACTGGACGAACCCTTAG

TGCTAAACAGCTACGTTACACCTATTTGCATTGCTACAAGGAATACACGAACATC

TTCCTCAAATTTGGATCTGGCTATGTAAGTGGCTGGGGAAGAGTCTTCCACAAAG

GGAGATCAGCTTTAGTTCTTCAGTACCTTAGAGTTCCACTTGTTGACCGAGCCAC

ATGTCTTCGATCTACAAAGTTCACCATCTATAACAACATGTTCTGTGCTGGCTTCC

ATGAAGGAGGTAGAGATTCATGTCAAGGAGATAGTGGGGGACCCCATGTTACTG

AAGTGGAAGGGACCAGTTTCTTAACTGGAATTATTAGCTGGGGTGAAGAGTGTG

CAATGAAAGGCAAATATGGAATATATACCAAGGTATCCCGGTATGTCAACTGGA

TTAAGGAAAAAACAAAGCTCACTAGCTCCAGCAGCAAGGCCCCTCCCCCGAGCC

TGCCCTCCCCAAGCAGGCTGCCTGGGCCCTCCGACACACCAATCCTGCCACAGAG

CAGCTCCTCTAAGGCCCCTCCTCCATCCCTGCCATCCCCCTCCCGGCTGCCTGGCC

CCTCTGACACCCCTATCCTGCCTCAGTGATGAAGGTCTGGATCCGCGGCCGC.

In another embodiment, the amino acid sequence of factor IX-CTP-CTP (attached to the carboxy terminus) comprises the following amino acid sequence:

(SEQ ID NO: 21)
MQRVNMIMAESPGLITICLLGYLLSAECTVFLDHENANKILNRPKRYNS

GKLEEFVQGNLERECMEEKCSFEEAREVFENTERTTEFWKQYVDGD

QCESNPCLNGGSCKDDINSYECWCPFGFEGKNCELDVTCNIKNGRC

EQFCKNSADNKVVCSCTEGYRLAENQKSCEPAVPFPCGRVSVSQTS

KLTRAETVFPDVDYVNSTEAETILDNITQSTQSFNDFTRVVGGEDAKPG

QFPWQVVLNGKVDAFCGGSIVNEKWIVTAAHCVETGVKITVVAGEHNIE

ETEHTEQKRNVIRIIPHHNYNAAINKYNHDIALLELDEPLVLNSYVTPIC

IADKEYTNIFLKFGSGYVSGWGRVFHKGRSALVLQYLRVPLVDRATCLR

STKFTIYNNMFCAGFHEGGRDSCQGDSGGPHVTEVEGTSFLTGIISWG

EECAMKGKYGIYTKVSRYVNWIKEKTKLTSSSSKAPPPSLPSPSRLPGP

SDTPILPQSSSSKAPPPSLPSPSRLPGPSDTPILPQ**.

In another embodiment, furin is added to a cell expressing the coagulation factor-CTP of the invention. In another embodiment, furin increases the production efficiency of a coagulation factor-CTP of the invention in a cell. In another embodiment, furin is co-transfected with the vector comprising the coding sequence of the coagulation factor-CTP of the invention. In another embodiment, furin is encoded by a separate vector. In another embodiment, furin and a coagulation factor-CTP are encoded by one vector. In another embodiment, the coding sequence of furin is inserted into pCI-DHFR. In another embodiment, the coding sequence of furin is engineered in pCI-dhfr/smaI+NotI, Furin/AsisI F.I.+NotI.

In another embodiment, the nucleic acid sequence encoding furin comprises the following nucleic acid sequence:

(SEQ ID NO: 22)
tctagagtcgacccCGCCATGGAGCTGAGGCCCTGGTTGCTATGGGTGGTAGCAGCAACA

GGAACCTTGGTCCTGCTAGCAGCTGATGCTCAGGGCCAGAAGGTCTTCACCAACA

CGTGGGCTGTGCGCATCCCTGGAGGCCCAGCGGTGGCCAACAGTGTGGCACGGA

AGCATGGGTTCCTCAACCTGGGCCAGATCTTCGGGGACTATTACCACTTCTGGCA

TCGAGGAGTGACGAAGCGGTCCCTGTCGCCTCACCGCCCGCGGCACAGCCGGCT

GCAGAGGGAGCCTCAAGTACAGTGGCTGGAACAGCAGGTGGCAAAGCGACGGA

CTAAACGGGACGTGTACCAGGAGCCCACAGACCCCAAGTTTCCTCAGCAGTGGT

ACCTGTCTGGTGTCACTCAGCGGGACCTGAATGTGAAGGCGGCCTGGGCGCAGG

GCTACACAGGGCACGGCATTGTGGTCTCCATTCTGGACGATGGCATCGAGAAGA

ACCACCCGGACTTGGCAGGCAATTATGATCCTGGGGCCAGTTTTGATGTCAATGA

CCAGGACCCTGACCCCCAGCCTCGGTACACACAGATGAATGACAACAGGCACGG

CACACGGTGTGCGGGGAAGTGGCTGCGGTGGCCAACAACGGTGTCTGTGGTGT

AGGTGTGGCCTACAACGCCCGCATTGGAGGGGTGCGCATGCTGGATGGCGAGGT

GACAGATGCAGTGGAGGCACGCTCGCTGGGCCTGAACCCCAACCACATCCACAT

CTACAGTGCCAGCTGGGGCCCCGAGGATGACGGCAAGACAGTGGATGGGCCAGC

CCGCCTCGCCGAGGAGGCCTTCTTCCGTGGGGTTAGCCAGGGCCGAGGGGGGCT

GGGCTCCATCTTTGTCTGGGCCTCGGGGAACGGGGCCGGGAACATGACAGCTG

CAACTGCGACGGCTACACCAACAGTATCTACACGCTGTCCATCAGCAGCGCCAC

GCAGTTTGGCAACGTGCCGTGGTACAGCGAGGCCTGCTCGTCCACACTGGCCACG

ACCTACAGCAGTGGCAACCAGAATGAGAAGCAGATCGTGACGACTGACTTGCGG

CAGAAGTGCACGGAGTCTCACACGGGCACCTCAGCCTCTGCCCCCTTAGCAGCCG

GCATCATTGCTCTCACCCTGGAGGCCAATAAGAACCTCACATGGCGGGACATGC

AACACCTGGTGGTACAGACCTCGAAGCCAGCCCACCTCAATGCCAACGACTGGG

CCACCAATGGTGTGGGCCGGAAAGTGAGCCACTCATATGGCTACGGGCTTTTGG

ACGCAGGCGCCATGGTGGCCCTGGCCCAGAATTGGACCACAGTGGCCCCCCAGC

GGAAGTGCATCATCGACATCCTCACCGAGCCCAAAGACATCGGGAAACGGCTCG

AGGTGCGGAAGACCGTGACCGCGTGCCTGGGCGAGCCCAACCACATCACTCGGC

```
-continued
TGGAGCACGCTCAGGCGCGGCTCACCCTGTCCTATAATCGCCGTGGCGACCTGGC

CATCCACCTGGTCAGCCCCATGGGCACCCGCTCCACCCTGCTGGCAGCCAGGCCA

CATGACTACTCCGCAGATGGGTTTAATGACTGGGCCTTCATGACAACTCATTCCT

GGGATGAGGATCCCTCTGGCGAGTGGGTCCTAGAGATTGAAAACACCAGCGAAG

CCAACAACTATGGGACGCTGACCAAGTTCACCCTCGTACTCTATGGCACCGCCCC

TGAGGGGCTGCCCGTACCTCCAGAAAGCAGTGGCTGCAAGACCCTCACGTCCAG

TCAGGCCTGTGTGGTGTGCGAGGAAGGCTTCTCCCTGCACCAGAAGAGCTGTGTC

CAGCACTGCCCTCCAGGCTTCGCCCCCCAAGTCCTCGATACGCACTATAGCACCG

AGAATGACGTGGAGACCATCCGGGCCAGCGTCTGCGCCCCCTGCCACGCCTCAT

GTGCCACATGCCAGGGGCCGGCCCTGACAGACTGCCTCAGCTGCCCCAGCCACG

CCTCCTTGGACCCTGTGGAGCAGACTTGCTCCCGGCAAAGCCAGAGCAGCCGAG

AGTCCCCGCCACAGCAGCAGCCACCTCGGCTGCCCCCGGAGGTGGAGGCGGGGC

AACGGCTGCGGGCAGGGCTGCTGCCCTCACACCTGCCTGAGGTGGTGGCCGGCC

TCAGCTGCGCCTTCATCGTGCTGGTCTTCGTCACTGTCTTCCTGGTCCTGCAGCTG

CGCTCTGGCTTTAGTTTTCGGGGGGTGAAGGTGTACACCATGGACCGTGGCCTCA

TCTCCTACAAGGGGCTGCCCCCTGAAGCCTGGCAGGAGGAGTGCCCGTCTGACTC

AGAAGAGGACGAGGGCCGGGGCGAGAGGACCGCCTTTATCAAAGACCAGAGCG

CCCTCTGAACGCGGCCGC.
```

In another embodiment, the amino acid sequence of furin comprises the following amino acid sequence:

```
                                               (SEQ ID NO: 23)
MELRPWLLWVVAATGTLVLLAADAQGQKVFTNTWAVRIPGGPAVANSVAR

KHGFLNLGQIFGDYYHFWHRGVTKRSLSPHRPRHSRLQREPQVQWLEQQV

AKRRTKRDVYQEPTDPKFPQQWYLSGVTQRDLNVKAAWAQGYTGHGIVV

SILDDGIEKNHPDLAGNYDPGASFDVNDQDPDPQPRYTQMNDNRHGTRC

AGEVAAVANNGVCGVGVAYNARIGGVRMLDGEVTDAVEARSLGLNPNHI

HIYSASWGPEDDGKTVDGPARLAEEAFFRGVSQGRGGLGSIFVWASG

NGGREHDSCNCDGYTNSIYTLSISSATQFGNVPWYSEACSSTLATTYSS

GNQNEKQIVTTDLRQKCTESHTGTSASAPLAAGIIALTLEANKNLTWRDM

QHLVVQTSKPAHLNANDWATNGVGRKVSHSYGYGLLDAGAMVALAQN

WTTVAPQRKCIIDILTEPKDIGKRLEVRKTVTACLGEPNHITRLEHAQAR

LTLSYNRRGDLAIHLVSPMGTRSTLLAARPHDYSADGFNDWAFMTTHSW

DEDPSGEWVLEIENTSEANNYGTLTKFTLVLYGTAPEGLPVPPESSGC

KTLTSSQACVVCEEGFSLHQKSCVQHCPPGFAPQVLDTHYSTENDVE

TIRASVCAPCHASCATCQGPALTDCLSCPSHASLDPVEQTCSRQSQSS

RESPPQQQPPRLPPEVEAGQRLRAGLLPSHLPEVVAGLSCAFIVLVFVT

VFLVLQLRSGFSFRGVKVYTMDRGLISYKGLPPEAWQEECPSDSEEDE

GRGERTAFIKDQSAL*.
```

In some embodiments, the term coagulation factor further includes homologues of known coagulation factors which have a coagulating activity. In some embodiments, homology according to the present invention also encompasses deletions, insertions, or substitution variants, including an amino acid substitution, thereof and biologically active polypeptide fragments thereof.

In another embodiment, the invention includes homologues of a coagulation factor having a coagulation activity. In another embodiment, the invention includes homologues of a coagulation factor as described herein having a coagulation activity. In another embodiment, homologues e.g., polypeptides which are at least 50%, at least 55%, at least 60%, at least 65%, at least 70%, at least 75%, at least 80%, at least 85%, at least 87%, at least 89%, at least 91%, at least 93%, at least 95% or more say 99% homologous to a coagulation factor as determined using BlastP software of the National Center of Biotechnology Information (NCBI) using default parameters.

In another embodiment, the invention includes homologues of furin. In another embodiment, homologues e.g., polypeptides which are at least 50%, at least 55%, at least 60%, at least 65%, at least 70%, at least 75%, at least 80%, at least 85%, at least 87%, at least 89%, at least 91%, at least 93%, at least 95% or more say 99% homologous to a furin as determined using BlastP software of the National Center of Biotechnology Information (NCBI) using default parameters.

In another embodiment, provided herein a polypeptide comprising a coagulation factor and one to ten gonadotrophin carboxy terminal (CTP) peptides attached to a carboxy terminus of the coagulation factor. In another embodiment, provided herein a polypeptide comprising a coagulation factor and two to eight gonadotrophin carboxy terminal (CTP) peptides attached to a carboxy terminus of the coagulation factor. In another embodiment, provided herein a polypeptide comprising a coagulation factor and one to three gonadotrophin carboxy terminal (CTP) peptides attached to a carboxy terminus of the coagulation factor. In another embodiment, provided herein a polypeptide comprising a coagulation factor and one to five gonadotrophin carboxy terminal (CTP) peptides attached to a carboxy terminus of the coagulation factor. In another embodiment, provided herein a polypeptide consisting a coagulation factor and one to five gonadotrophin carboxy terminal (CTP) peptides attached to a carboxy terminus of the coagulation factor. In another embodiment, provided herein a polypeptide comprising a coagulation factor and one to five CTPs attached to a carboxy terminus of the coagulation factor. In another embodiment, provided herein a polypeptide comprising a coagulation factor having no CTPs on its amino terminus. In another embodiment, provided herein a polypeptide comprising a coagulation factor having at least one CTP on its carboxy terminus. In another embodiment, provided herein a polypeptide comprising a coagulation factor having at least one CTP on its carboxy terminus and no CTPs on its amino terminus.

In other embodiments, engineered coagulation factor is a polypeptide comprising a coagulation factor having at least one CTP on its carboxy terminus. In other embodiments, engineered coagulation factor is a polypeptide comprising a coagulation factor having one CTP on its carboxy terminus. In other embodiments, engineered coagulation factor is a polypeptide consisting a coagulation factor having one CTP on its carboxy terminus. In other embodiments, engineered coagulation factor comprises two CTP peptides attached in tandem to the carboxy terminus. In another embodiment, an engineered coagulation factor as described herein is equivalent to the non CTP modified coagulation factor in terms of biological activity. In another embodiment, an engineered coagulation factor as described herein is at least equivalent to the non CTP modified coagulation factor, in terms of pharmacological measures such as pharmacokinetics and/or pharmacodynamics.

In other embodiments, engineered coagulation factor is intended to be used for the treatment of hemophilic B patients. In another embodiment, coagulation factor IX comprising 2 CTPs in tandem in its carboxy terminus (MOD-3012) is intended to be used for the treatment of hemophilic B patients. In another embodiment, coagulation factor IX comprising 1 CTP repeat in its carboxy terminus (MOD-3011) is intended to be used for the treatment of hemophilic B patients. In other embodiments, engineered coagulation factor can reduce the rate of infusions, reduce the required doses, or a combination thereof.

In another embodiment, coagulation factor IX comprising 2 CTPs in tandem in its carboxy terminus (MOD-3012) exhibits an improved PK profile while maintaining its coagulation activity vs. FIX-CTP harvest or rhFIX. In another embodiment, coagulation factor IX comprising 2 CTPs in tandem in its carboxy terminus (MOD-3012) exhibits 3 fold increase in half life and 4.5 fold higher AUC compared to rhFIX.

In another embodiment, the terms "CTP peptide," "carboxy terminal peptide" and "CTP sequence" are used interchangeably herein. In another embodiment, the carboxy terminal peptide is a full-length CTP. In another embodiment, the carboxy terminal peptide is a truncated CTP. Each possibility represents a separate embodiment of the present invention.

In other embodiments, the term engineered coagulation factor comprises the amino acid sequence of a matured coagulation factor. In other embodiments, the term engineered coagulation factor comprises the amino acid sequence of coagulation factor including its signal sequence or signal peptide.

In another embodiment, "signal sequence" and "signal peptide" are used interchangeably herein. In another embodiment, "sequence" when in reference to a polynucleotide molecule can refer to a coding portion. Each possibility represents a separate embodiment of the present invention.

In another embodiment, an engineered coagulation factor comprising at least one CTP as described herein has enhanced in-vivo biological activity compared the same coagulation factor without at least one CTP.

In some embodiments, at least one CTP sequence at the carboxy terminal end of the coagulation factor provides enhanced protection against degradation of a coagulation factor. In some embodiments, at least one CTP sequence at the carboxy terminal end of the coagulation factor provides enhanced protection against clearance. In some embodiments, at least one CTP sequence at the carboxy terminal end of the coagulation factor provides prolonged clearance time. In some embodiments, at least one CTP sequence at the carboxy terminal end of the coagulation factor enhances its $C_{max}$. In some embodiments, at least one CTP sequence at the carboxy terminal end of the coagulation factor provides enhanced protection against enhances its $T_{max}$. In some embodiments, at least one CTP sequence at the carboxy terminal end of the coagulation factor prolongs its T1/2.

In another embodiment, a conjugated coagulation factor of this invention is used in the same manner as an unmodified conjugated coagulation factor. In another embodiment, a conjugated coagulation factor of this invention have an increased circulating half-life and plasma residence time, decreased clearance, and increased clinical activity in vivo. In another embodiment, due to the improved properties of the conjugated coagulation factor as described herein, this conjugate is administered less frequently than the unmodified form of the same coagulation factor.

In another embodiment, decreased frequency of administration will result in improved patient compliance leading to improved treatment outcomes, as well as improved patient quality of life. In another embodiment, compared to conventional conjugates of coagulation factors it has been found that conjugates having the molecular weight and linker structure of the conjugates of this invention have an improved potency, improved stability, elevated AUC levels, and enhanced circulating half-life.

In another embodiment, provided herein a composition comprising the conjugated coagulation factor as described herein. In another embodiment, provided herein a pharmaceutical composition comprising the conjugated coagulation factor as described herein. In another embodiment, a therapeutically effective amount of a conjugated coagulation factor is determined according to factors as the exact type of condition being treated, the condition of the patient being treated, as well as the other ingredients in the composition. In another embodiment, a therapeutically effective amount of a conjugated coagulation factor is between 50-500 IU per kg body weight administered once a day to once a week. In another embodiment, a therapeutically effective amount of a conjugated coagulation factor is 150-250 IU per kg body weight, administered once a day. In another embodiment, a pharmaceutical composition comprising a conjugated coagulation factor is formulated at a strength effective for administration by various means to a human patient.

In another embodiment, a conjugated coagulation factor as described herein is useful in the treatment of subjects afflicted with Hemophilia. In another embodiment, a conjugated coagulation factor as described herein is useful in the prophylactic therapy of Hemophilia thus reducing the risk of bleeding and associated complications. In another embodiment, a conjugated coagulation factor as described herein is useful in the treatment of subjects afflicted with Hemophilia while reducing the risk of developing inhibitory antibodies to exogenously administered coagulation factors. In another embodiment, a conjugated coagulation factor as described herein is useful in the treatment of subjects afflicted with Hemophilia thus inducing homeostasis.

In another embodiment, a conjugated coagulation factor as described herein is useful in the treatment of subjects experiencing excessive bleeding or bruising or having a prolonged Prothrombin Time (PT) or Partial Thromboplastin Time (PTT). In another embodiment, a conjugated coagulation factor as described herein is useful in the treatment of subjects having an acquired condition that is causing bleeding, such as vitamin K deficiency or liver disease. In another embodiment, a conjugated coagulation factor as described herein is useful in the treatment of subjects having deficiencies in coagulation factors that are acquired (due to other diseases) or inherited, mild or severe, permanent or temporary. In another embodiment, a conjugated coagulation factor as described herein is useful in the treatment of subjects afflicted with hemophilia A. In another embodiment, a conjugated coagulation factor as described herein is useful in the treatment of subjects afflicted with hemophilia B. In another embodiment, a conjugated coagulation factor as described herein is useful in the treatment of subjects having acquired deficiencies due to chronic diseases, such as liver disease or cancer; to an acute condition such as disseminated intravascular coagulation (DIC), which uses up clotting factors at a rapid rate; or to a deficiency in vitamin K or treatment with a vitamin K antagonist like warfarin (the production of factors II, VII, IX, and X require vitamin K). In another embodiment, a conjugated coagulation factor as described herein is useful in the treatment of subjects afflicted with a disease in which causes clotting imbalances such as but not limited to: a liver disease, uremia, a cancer, a bone marrow disorder, an exposure to snake venom, a vitamin K deficiency, an anticoagulation therapy, an accidental ingestion of the anticoagulant warfarin, a multiple blood transfusions (stored units of blood lose some of their clotting factors).

In another embodiment, a subject as used herein is a human subject. In another embodiment, a subject is a pet. In another embodiment, a subject is a mammal. In another embodiment, a subject is a farm animal. In another embodiment, a subject is a monkey. In another embodiment, a subject is a horse. In another embodiment, a subject is a cow. In another embodiment, a subject is a mouse. In another embodiment, a subject is a rat.

In another embodiment, a [(CTP)$_{n>1}$-coagulation factor] as described herein comprises a full length coagulation factor or an active fragment thereof connected via a peptide bond on its carboxy terminus to at least one CTP unit with no CTPs on its amino terminus. In another embodiment, a [(CTP)$_{n>1}$-coagulation factor] as described herein comprises a coagulation factor or an active fragment thereof connected via a peptide bond to at least one CTP unit which is connected to an additional CTP unit via a peptide bond with no CTPs on its amino terminus. In another embodiment, one nucleic acid molecule encodes an engineered coagulation factor comprising at least one CTP attached to its C-terminus and no CTPs on its amino terminus.

In another embodiment, the CTP is attached to the coagulation factor via a linker. In another embodiment, the linker which connects the CTP sequence to the coagulation factor is a covalent bond. In another embodiment, the linker which connects the CTP sequence to the coagulation factor is a peptide bond. In another embodiment, the linker which connects the CTP sequence to the coagulation factor is a substituted peptide bond. In another embodiment, the CTP sequence comprises an amino acid sequence selected from the sequences set forth in SEQ ID NO: 1 and SEQ ID NO: 2.

In another embodiment, SEQ ID NO: 1 comprises the following amino acid (AA) sequence: DPRFQDSSSSKAPPPSLPSPSRLPGPSDTPIL (SEQ ID NO: 1). In another embodiment, SEQ ID NO: 2 comprises the following amino acid (AA) sequence: SSSSKAPPPSLPSPSRLPGPSDTPILPQ (SEQ ID NO: 2).

In another embodiment, the carboxy terminal peptide (CTP) peptide of the present invention comprises the amino acid sequence from amino acid 112 to position 145 of human chorionic gonadotrophin, as set forth in SEQ ID NO: 1. In another embodiment, the CTP sequence of the present invention comprises the amino acid sequence from amino acid 118 to position 145 of human chorionic gonadotropin, as set forth in SEQ ID NO: 2. In another embodiment, the CTP sequence also commences from any position between positions 112-118 and terminates at position 145 of human chorionic gonadotrophin. In some embodiments, the CTP sequence peptide is 28, 29, 30, 31, 32, 33 or 34 amino acids long and commences at position 112, 113, 114, 115, 116, 117 or 118 of the CTP amino acid sequence.

In another embodiment, the CTP peptide is a variant of chorionic gonadotrophin CTP which differs from the native CTP by 1-5 conservative amino acid substitutions as described in U.S. Pat. No. 5,712,122 which is incorporated herein be reference. In another embodiment, the CTP peptide is a variant of chorionic gonadotrophin CTP which differs from the native CTP by 1 conservative amino acid substitution. In another embodiment, the CTP peptide is a variant of chorionic gonadotrophin CTP which differs from the native CTP by 2 conservative amino acid substitutions. In another embodiment, the CTP peptide is a variant of chorionic gonadotrophin CTP which differs from the native CTP by 3 conservative amino acid substitutions. In another embodiment, the CTP peptide is a variant of chorionic gonadotrophin CTP which differs from the native CTP by 4 conservative amino acid substitutions. In another embodiment, the CTP peptide is a variant of chorionic gonadotrophin CTP which differs from the native CTP by 5 conservative amino acid substitutions. In another embodiment, the CTP peptide amino acid sequence of the present invention is at least 70% homologous to the native CTP amino acid sequence or a peptide thereof. In another embodiment, the CTP peptide amino acid sequence of the present invention is at least 80% homologous to the native CTP amino acid sequence or a peptide thereof. In another embodiment, the CTP peptide amino acid sequence of the present invention is at least 90% homologous to the native CTP amino acid sequence or a peptide thereof. In another embodiment, the CTP peptide amino acid sequence of the present invention is at least 95% homologous to the native CTP amino acid sequence or a peptide thereof.

In another embodiment, the CTP peptide DNA sequence of the present invention is at least 70% homologous to the native human CTP DNA sequence or a peptide thereof. In another embodiment, the CTP peptide DNA sequence of the present invention is at least 80% homologous to the native human CTP DNA sequence or a peptide thereof. In another embodiment, the CTP peptide DNA sequence of the present invention is at least 90% homologous to the native CTP DNA sequence or a peptide thereof. In another embodiment, the CTP peptide DNA sequence of the present invention is at least 95% homologous to the native CTP DNA sequence or a peptide thereof.

In one embodiment, at least one of the chorionic gonadotrophin CTP amino acid sequences is truncated. In another embodiment, both of the chorionic gonadotrophin CTP amino acid sequences are truncated. In another embodiment, 2 of the chorionic gonadotrophin CTP amino acid sequences are truncated. In another embodiment, 2 or more of the chorionic gonadotrophin CTP amino acid sequences are truncated. In another embodiment, all of the chorionic gonadotrophin CTP amino acid sequences are truncated. In one embodiment, the truncated CTP comprises the first 10 amino acids of SEQ ID NO: 3. In another embodiment, SEQ ID NO: 3 comprises the following amino acid (AA) sequence: SSSSKAPPPSLP.

In one embodiment, the truncated CTP comprises the first 10 amino acids of SEQ ID NO: 4. In another embodiment, SEQ ID NO: 4 comprises the following amino acid (AA) sequence: SSSSKAPPPSLPSPSRLPGPSDTPILPQ.

In one embodiment, the truncated CTP comprises the first 11 amino acids of SEQ ID NO: 4. In one embodiment, the truncated CTP comprises the first 12 amino acids of SEQ ID NO: 4. In one embodiment, the truncated CTP comprises the first 8 amino acids of SEQ ID NO: 4 or SEQ ID NO: 3. In one embodiment, the truncated CTP comprises the first 13 amino acids of SEQ ID NO: 4. In one embodiment, the truncated CTP comprises the first 14 amino acids of SEQ ID NO: 4. In one embodiment, the truncated CTP comprises the first 6 amino acids of SEQ ID NO: 4 or SEQ ID NO: 3. In one embodiment, the truncated CTP comprises the first 5 amino acids of SEQ ID NO: 4 or SEQ ID NO: 3.

In one embodiment, at least one of the chorionic gonadotrophin CTP amino acid sequences is glycosylated. In another embodiment, both of the chorionic gonadotrophin CTP amino acid sequences are glycosylated. In another embodiment, 2 of the chorionic gonadotrophin CTP amino acid sequences are glycosylated. In another embodiment, 2 or more of the chorionic gonadotrophin CTP amino acid sequences are glycosylated. In another embodiment, all of the chorionic gonadotrophin CTP amino acid sequences are glycosylated. In one embodiment, the CTP sequence of the present invention comprises at least one glycosylation site. In one embodiment, the CTP sequence of the present invention comprises 2 glycosylation sites. In one embodiment, the CTP sequence of the present invention comprises 3 glycosylation sites. In one embodiment, the CTP sequence of the present invention comprises 4 glycosylation sites.

In some embodiments, the CTP sequences modification is advantageous in permitting the usage of lower dosages. In some embodiments, the CTP sequences modification is advantageous in permitting fewer dosages. In some embodiments, the CTP sequences modification is advantageous in permitting a safe long acting effect.

In some embodiments, "polypeptide", "engineered coagulation factor", or "protein" as used herein encompasses native polypeptides (either degradation products, synthetically synthesized polypeptides or recombinant polypeptides) and peptidomimetics (typically, synthetically synthesized polypeptides), as well as peptoids and semipeptoids which are polypeptide analogs, which have, in some embodiments, modifications rendering the polypeptides comprising a coagulation factor even more stable while in a body or more capable of penetrating into cells.

In some embodiments, modifications include, but are limited to C terminus modification, polypeptide bond modification, including, but not limited to, CH2-NH, CH2-S, CH2-S=O, O=C—NH, CH2-O, CH2-CH2, S=C—NH, CH=CH or CF=CH, backbone modifications, and residue modification. Methods for preparing peptidomimetic compounds are well known in the art and are specified, for example, in Quantitative Drug Design, C.A. Ramsden Gd., Chapter 17.2, F. Choplin Pergamon Press (1992), which is incorporated by reference as if fully set forth herein. Further details in this respect are provided hereinunder.

In some embodiments, polypeptide bonds (—CO—NH—) within the polypeptide are substituted. In some embodiments, the polypeptide bonds are substituted by N-methylated bonds (—N(CH3)-CO—). In some embodiments, the polypeptide bonds are substituted by ester bonds (—C(R)H—C—O—O—C(R)—N—). In some embodiments, the polypeptide bonds are substituted by ketomethylen bonds (—CO—CH2-). In some embodiments, the polypeptide bonds are substituted by α-aza bonds (—NH—N(R)—CO—), wherein R is any alkyl, e.g., methyl, carba bonds (—CH2-NH—). In some embodiments, the polypeptide bonds are substituted by hydroxyethylene bonds (—CH(OH)—CH2-). In some embodiments, the polypeptide bonds are substituted by thioamide bonds (—CS—NH—). In some embodiments, the polypeptide bonds are substituted by olefinic double bonds (—CH=CH—). In some embodiments, the polypeptide bonds are substituted by retro amide bonds (—NH—CO—). In some embodiments, the polypeptide bonds are substituted by polypeptide derivatives (—N(R)—CH2-CO—), wherein R is the "normal" side chain, naturally presented on the carbon atom. In some embodiments, these modifications occur at any of the bonds along the polypeptide chain and even at several (2-3 bonds) at the same time.

In some embodiments, natural aromatic amino acids of the polypeptide such as Trp, Tyr and Phe, are substituted for synthetic non-natural acid such as Phenylglycine, TIC, naphthylelanine (Nol), ring-methylated derivatives of Phe, halogenated derivatives of Phe or o-methyl-Tyr. In some embodiments, the polypeptides of the present invention include one or more modified amino acid or one or more non-amino acid monomers (e.g. fatty acid, complex carbohydrates etc).

In one embodiment, "amino acid" or "amino acid sequence" is understood to include the 20 naturally occurring amino acid; those amino acid often modified post-translationally in vivo, including, for example, hydroxyproline, phosphoserine and phosphothreonine; and other unusual amino acid including, but not limited to, 2-aminoadipic acid, hydroxylysine, isodesmosine, nor-valine, nor-leucine and ornithine. In one embodiment, "amino acid" includes both D- and L-amino acid.

In some embodiments, the polypeptides of the present invention are utilized in therapeutics which requires the polypeptides comprising a coagulation factor to be in a soluble form. In some embodiments, the polypeptides of the present invention include one or more non-natural or natural polar amino acid, including but not limited to serine and threonine which are capable of increasing polypeptide solubility due to their hydroxyl-containing side chain.

In some embodiments, the engineered coagulation factor of the present invention is utilized in a linear form, although it will be appreciated by one skilled in the art that in cases where cyclicization does not severely interfere with engineered coagulation factors characteristics, cyclic forms of the engineered coagulation factors can also be utilized.

In some embodiments, the engineered coagulation factors of present invention are biochemically synthesized such as by using standard solid phase techniques. In some embodiments, these biochemical methods include exclusive solid phase synthesis, partial solid phase synthesis, fragment condensation, or classical solution synthesis.

In some embodiments, recombinant protein techniques are used to generate the engineered coagulation factors of the present invention. In some embodiments, recombinant protein techniques are used for the generation of relatively long polypeptides (e.g., longer than 18-25 amino acids). In some embodiments, recombinant protein techniques are used for the generation of large amounts of the engineered coagulation factors of the present invention. In some embodiments, recombinant techniques are described by Bitter et al., (1987) Methods in Enzymol. 153:516-544, Studier et al. (1990) Methods in Enzymol. 185:60-89, Brisson et al. (1984) Nature 310:511-514, Takamatsu et al. (1987) EMBO J. 6:307-311, Coruzzi et al. (1984) EMBO J. 3:1671-1680 and Brogli et al., (1984) Science 224:838-843, Gurley et al. (1986) Mol. Cell. Biol. 6:559-565 and Weissbach & Weissbach, 1988, Methods for Plant Molecular Biology, Academic Press, NY, Section VIII, pp 421-463.

In another embodiment, the invention provides a polynucleotide molecule comprising a coding portion encoding a polypeptide comprising a coagulation factor and one to ten gonadotrophin carboxy terminal peptides attached to a carboxy terminus of the coagulation factor. In another embodiment, the invention provides a polynucleotide molecule comprising a coding portion encoding a polypeptide consisting a coagulation factor and one to ten gonadotrophin carboxy terminal peptides attached to a carboxy terminus of the coagulation factor. In another embodiment, the invention provides a polynucleotide molecule comprising a coding portion encoding a polypeptide consisting a coagulation factor and one to seven gonadotrophin carboxy terminal peptides attached to a carboxy terminus of the coagulation factor. In another embodiment, the invention provides a polynucleotide molecule comprising a coding portion encoding a polypeptide consisting a coagulation factor and two to eight gonadotrophin carboxy terminal peptides attached to a carboxy terminus of the coagulation factor. In another embodiment, the invention provides a polynucleotide molecule comprising a coding portion encoding a polypeptide consisting a coagulation factor and one to five gonadotrophin carboxy terminal peptides attached to a carboxy terminus of the coagulation factor.

In another embodiment, the invention provides an expression vector comprising a polynucleotide molecule as described herein. In another embodiment, the invention provides a cell comprising the expression vector as described herein. In another embodiment, the invention provides a composition comprising the expression vector as described herein. In another embodiment, the invention provides a composition comprising the cell as described herein. In another embodiment, the cell is a eukaryotic cell. In another embodiment, the cell is a prokaryotic cell.

In another embodiment, engineered coagulation factors of the present invention are synthesized using a polynucleotide molecule encoding a polypeptide of the present invention. In some embodiments, the polynucleotide molecule encoding engineered coagulation factors of the present invention is ligated into an expression vector, comprising a transcriptional control of a cis-regulatory sequence (e.g., promoter sequence). In some embodiments, the cis-regulatory sequence is suitable for directing constitutive expression of the engineered coagulation factors of the present invention. In some embodiments, the cis-regulatory sequence is suitable for directing tissue specific expression of the engineered coagulation factors of the present invention. In some embodiments, the cis-regulatory sequence is suitable for directing inducible expression of the engineered coagulation factors of the present invention.

In some embodiment, tissue-specific promoters suitable for use with the present invention include sequences which are functional in specific cell population, example include, but are not limited to promoters such as albumin that is liver specific [Pinkert et al., (1987) Genes Dev. 1:268-277], lymphoid specific promoters [Calame et al., (1988) Adv. Immunol. 43:235-275]; in particular promoters of T-cell receptors [Winoto et al., (1989) EMBO J. 8:729-733] and immunoglobulins; [Banerji et al. (1983) Cell 33729-740], neuron-specific promoters such as the neurofilament promoter [Byrne et al. (1989) Proc. Natl. Acad. Sci. USA 86:5473-5477], pancreas-specific promoters [Edlunch et al. (1985) Science 230: 912-916] or mammary gland-specific promoters such as the milk whey promoter (U.S. Pat. No. 4,873,316 and European Application Publication No. 264,166). Inducible promoters suitable for use with the present invention include for example the tetracycline-inducible promoter (Srour, M. A., et al., 2003. Thromb. Haemost. 90: 398-405).

In one embodiment, the phrase "a polynucleotide molecule" refers to a single or double stranded nucleic acid sequence which be isolated and provided in the form of an RNA sequence, a complementary polynucleotide sequence (cDNA), a genomic polynucleotide sequence and/or a composite polynucleotide sequences (e.g., a combination of the above).

In one embodiment, "complementary polynucleotide sequence" refers to a sequence, which results from reverse transcription of messenger RNA using a reverse transcriptase or any other RNA dependent DNA polymerase. In one embodiment, the sequence can be subsequently amplified in-vivo or in-vitro using a DNA polymerase.

In one embodiment, "genomic polynucleotide sequence" refers to a sequence derived (isolated) from a chromosome and thus it represents a contiguous portion of a chromosome.

In one embodiment, "composite polynucleotide sequence" refers to a sequence, which is at least partially complementary and at least partially genomic. In one embodiment, a composite sequence can include some exonal sequences required to encode the polypeptide of the present invention, as well as some intronic sequences interposing there between In one embodiment, the intronic sequences can be of any source, including of other genes, and typically will include conserved splicing signal sequences. In one embodiment, intronic sequences include cis acting expression regulatory elements.

In one embodiment, following expression and secretion, the signal peptides are cleaved from the precursor engineered coagulation factors resulting in the mature engineered coagulation factors.

In some embodiments, polynucleotides of the present invention are prepared using PCR techniques, or any other method or procedure known to one skilled in the art. In some embodiments, the procedure involves the ligation of two different DNA sequences (See, for example, "Current Protocols in Molecular Biology", eds. Ausubel et al., John Wiley & Sons, 1992).

In one embodiment, polynucleotides of the present invention which encode the engineered coagulation factors are inserted into expression vectors (i.e., a nucleic acid construct) to enable expression of the recombinant polypeptide. In one embodiment, the expression vector of the present invention includes additional sequences which render this vector suitable for replication and integration in prokaryotes. In one embodiment, the expression vector of the present invention includes additional sequences which render this vector suitable for replication and integration in eukaryotes. In one embodiment, the expression vector of the present invention includes a shuttle vector which renders this vector suitable for replication and integration in both prokaryotes and eukaryotes. In some embodiments, cloning vectors comprise transcription and translation initiation sequences (e.g., promoters, enhances) and transcription and translation terminators (e.g., polyadenylation signals).

In one embodiment, a variety of prokaryotic or eukaryotic cells can be used as host-expression systems to express the coagulation factors of the present invention. In some embodiments, these include, but are not limited to, microorganisms, such as bacteria transformed with a recombinant bacteriophage DNA, plasmid DNA or cosmid DNA expression vector containing the polypeptide coding sequence; yeast transformed with recombinant yeast expression vectors containing the polypeptide coding sequence; plant cell systems infected with recombinant virus expression vectors (e.g., cauliflower mosaic virus, CaMV; tobacco mosaic virus, TMV) or transformed with recombinant plasmid expression vectors, such as Ti plasmid, containing the polypeptide coding sequence.

In some embodiments, non-bacterial expression systems are used (e.g. mammalian expression systems such as CHO cells) to express the coagulation factors of the present invention. In one embodiment, the expression vector used to express polynucleotides of the present invention in mammalian cells is pCI-DHFR vector comprising a CMV promoter and a neomycin resistance gene. Construction of the pCI-dhfr vector is described, according to one embodiment, in Example 1.

In some embodiments, in bacterial systems of the present invention, a number of expression vectors can be advantageously selected depending upon the use intended for the polypeptide expressed. In one embodiment, large quantities of polypeptide are desired. In one embodiment, vectors that direct the expression of high levels of the protein product, possibly as a fusion with a hydrophobic signal sequence, which directs the expressed product into the periplasm of the bacteria or the culture medium where the protein product is readily purified are desired. In one embodiment, certain fusion protein engineered with a specific cleavage site to aid in recovery of the polypeptide. In one embodiment, vectors adaptable to such manipulation include, but are not limited to, the pET series of E. coli expression vectors [Studier et al., Methods in Enzymol. 185:60-89 (1990)].

In one embodiment, yeast expression systems are used. In one embodiment, a number of vectors containing constitutive or inducible promoters can be used in yeast as disclosed in U.S. Pat. No. 5,932,447. In another embodiment, vectors which promote integration of foreign DNA sequences into the yeast chromosome are used.

In one embodiment, the expression vector of the present invention can further include additional polynucleotide sequences that allow, for example, the translation of several proteins from a single mRNA such as an internal ribosome entry site (IRES) and sequences for genomic integration of the promoter-chimeric polypeptide.

In some embodiments, mammalian expression vectors include, but are not limited to, pcDNA3, pcDNA3.1 (+/−), pGL3, pZeoSV2 (+/−), pSecTag2, pDisplay, pEF/myc/cyto, pCMV/myc/cyto, pCR3.1, pSinRep5, DH26S, DHBB, pNMT1, pNMT41, pNMT81, which are available from Invitrogen, pCI which is available from Promega, pMbac, pPbac, pBK-RSV and pBK-CMV which are available from Strategene, pTRES which is available from Clontech, and their derivatives.

In some embodiments, expression vectors containing regulatory elements from eukaryotic viruses such as retroviruses are used by the present invention. SV40 vectors include pSVT7 and pMT2. In some embodiments, vectors derived from bovine papilloma virus include pBV-1MTHA, and vectors derived from Epstein Bar virus include pHEBO, and p2O5. Other exemplary vectors include pMSG, pAV009/A$^+$, pMTO10/A$^+$, pMAMneo-5, baculovirus pDSVE, and any other vector allowing expression of proteins under the direction of the SV-40 early promoter, SV-40 later promoter, metallothionein promoter, murine mammary tumor virus promoter, Rous sarcoma virus promoter, polyhedrin promoter, or other promoters shown effective for expression in eukaryotic cells.

In some embodiments, recombinant viral vectors are useful for in-vivo expression of the coagulation factors of the present invention since they offer advantages such as lateral infection and targeting specificity. In one embodiment, lateral infection is inherent in the life cycle of, for example, retrovirus and is the process by which a single infected cell produces many progeny virions that bud off and infect neighboring cells. In one embodiment, the result is that a large area becomes rapidly infected, most of which was not initially infected by the original viral particles. In one embodiment, viral vectors are produced that are unable to spread laterally. In one embodiment, this characteristic can be useful if the desired purpose is to introduce a specified gene into only a localized number of targeted cells.

In one embodiment, various methods can be used to introduce the expression vector of the present invention into cells. Such methods are generally described in Sambrook et al., Molecular Cloning: A Laboratory Manual, Cold Springs Harbor Laboratory, New York (1989, 1992), in Ausubel et al., Current Protocols in Molecular Biology, John Wiley and Sons, Baltimore, Md. (1989), Chang et al., Somatic Gene Therapy, CRC Press, Ann Arbor, Mich. (1995), Vega et al., Gene Targeting, CRC Press, Ann Arbor Mich. (1995), Vectors: A Survey of Molecular Cloning Vectors and Their Uses, Butterworths, Boston Mass. (1988) and Gilboa et at. [Biotechniques 4 (6): 504-512, 1986] and include, for example, stable or transient transfection, lipofection, electroporation and infection with recombinant viral vectors. In addition, see U.S. Pat. Nos. 5,464,764 and 5,487,992 for positive-negative selection methods.

In some embodiments, introduction of nucleic acid by viral infection offers several advantages over other methods such as lipofection and electroporation, since higher transfection efficiency can be obtained due to the infectious nature of viruses.

In one embodiment, it will be appreciated that the engineered coagulation factors of the present invention can also be expressed from a nucleic acid construct administered to the individual employing any suitable mode of administration, described hereinabove (i.e., in-vivo gene therapy). In one embodiment, the nucleic acid construct is introduced into a suitable cell via an appropriate gene delivery vehicle/method (transfection, transduction, homologous recombination, etc.) and an expression system as needed and then the modified cells are expanded in culture and returned to the individual (i.e., ex-vivo gene therapy).

In one embodiment, plant expression vectors are used. In one embodiment, the expression of a polypeptide coding sequence is driven by a number of promoters. In some embodiments, viral promoters such as the 35S RNA and 19S RNA promoters of CaMV [Brisson et al., Nature 310:511-514 (1984)], or the coat protein promoter to TMV [Takamatsu et al., EMBO J. 6:307-311 (1987)] are used. In another embodiment, plant promoters are used such as, for example, the small subunit of RUBISCO [Coruzzi et al., EMBO J. 3:1671-1680 (1984); and Brogli et al., Science 224:838-843 (1984)] or heat shock promoters, e.g., soybean hsp17.5-E or hsp17.3-B [Gurley et al., Mol. Cell. Biol. 6:559-565 (1986)]. In one embodiment, constructs are introduced into plant cells using Ti plasmid, Ri plasmid, plant viral vectors, direct DNA transformation, microinjection, electroporation and other techniques well known to the skilled artisan. See, for example, Weissbach & Weissbach [Methods for Plant Molecular Biology, Academic Press, NY, Section VIII, pp 421-463 (1988)]. Other expression systems such as insects and mammalian host cell systems, which are well known in the art, can also be used by the present invention.

It will be appreciated that other than containing the necessary elements for the transcription and translation of the inserted coding sequence (encoding the polypeptide), the expression construct of the present invention can also include sequences engineered to optimize stability, production, purification, yield or activity of the expressed polypeptide.

Various methods, in some embodiments, can be used to introduce the expression vector of the present invention into the host cell system. In some embodiments, such methods are generally described in Sambrook et al., Molecular Cloning: A Laboratory Manual, Cold Springs Harbor Laboratory, New York (1989, 1992), in Ausubel et al., Current Protocols in Molecular Biology, John Wiley and Sons, Baltimore, Md. (1989), Chang et al., Somatic Gene Therapy, CRC Press, Ann Arbor, Mich. (1995), Vega et al., Gene Targeting, CRC Press, Ann Arbor Mich. (1995), Vectors: A Survey of Molecular Cloning Vectors and Their Uses, Butterworths, Boston Mass. (1988) and Gilboa et at. [Biotechniques 4 (6): 504-512, 1986] and include, for example, stable or transient transfection, lipofection, electroporation and infection with recombinant viral vectors. In addition, see U.S. Pat. Nos. 5,464,764 and 5,487,992 for positive-negative selection methods.

In some embodiments, transformed cells are cultured under effective conditions, which allow for the expression of high amounts of recombinant engineered coagulation factors. In some embodiments, effective culture conditions include, but are not limited to, effective media, bioreactor, temperature, pH and oxygen conditions that permit protein production. In one embodiment, an effective medium refers to any medium in which a cell is cultured to produce the recombinant polypeptide of the present invention. In some embodiments, a medium typically includes an aqueous solution having assimilable carbon, nitrogen and phosphate sources, and appropriate salts, minerals, metals and other nutrients, such as vitamins. In some embodiments, cells of the present invention can be cultured in conventional fermentation bioreactors, shake flasks, test tubes, microtiter dishes and petri plates. In some embodiments, culturing is carried out at a temperature, pH and oxygen content appropriate for a recombinant cell. In some embodiments, culturing conditions are within the expertise of one of ordinary skill in the art.

In some embodiments, depending on the vector and host system used for production, resultant engineered coagulation factors of the present invention either remain within the recombinant cell, secreted into the fermentation medium, secreted into a space between two cellular membranes, such as the periplasmic space in *E. coli*; or retained on the outer surface of a cell or viral membrane.

In one embodiment, following a predetermined time in culture, recovery of the recombinant engineered coagulation factor is effected.

In one embodiment, the phrase "recovering the recombinant engineered coagulation factor" used herein refers to collecting the whole fermentation medium containing the polypeptide and need not imply additional steps of separation or purification.

In one embodiment, engineered coagulation factors of the present invention are purified using a variety of standard protein purification techniques, such as, but not limited to, affinity chromatography, ion exchange chromatography, filtration, electrophoresis, hydrophobic interaction chromatography, gel filtration chromatography, reverse phase chromatography, concanavalin A chromatography, chromatofocusing and differential solubilization.

In one embodiment, to facilitate recovery, the expressed coding sequence can be engineered to encode the engineered coagulation factor of the present invention and fused cleavable moiety. In one embodiment, a fusion protein can be designed so that the polypeptide can be readily isolated by affinity chromatography; e.g., by immobilization on a column specific for the cleavable moiety. In one embodiment, a cleavage site is engineered between the engineered coagulation factor and the cleavable moiety and the polypeptide can be released from the chromatographic column by treatment with an appropriate enzyme or agent that specifically cleaves the fusion protein at this site [e.g., see Booth et al., Immunol. Lett. 19:65-70 (1988); and Gardella et al., J. Biol. Chem. 265:15854-15859 (1990)].

In one embodiment, the engineered coagulation factor of the present invention is retrieved in "substantially pure" form.

In one embodiment, the phrase "substantially pure" refers to a purity that allows for the effective use of the protein in the applications described herein.

In one embodiment, the engineered coagulation factor of the present invention can also be synthesized using in-vitro expression systems. In one embodiment, in-vitro synthesis methods are well known in the art and the components of the system are commercially available.

In some embodiments, the recombinant engineered coagulation factors are synthesized and purified; their therapeutic efficacy can be assayed either in-vivo or in vitro. In one embodiment, the binding activities of the recombinant engineered coagulation factors of the present invention can be ascertained using various assays as known to one of skill in the art.

In another embodiment, the engineered coagulation factor of the present invention can be provided to the individual per se. In one embodiment, the engineered coagulation factor of the present invention can be provided to the individual as part of a pharmaceutical composition where it is mixed with a pharmaceutically acceptable carrier.

In another embodiment, a "pharmaceutical composition" refers to a preparation of one or more of the active ingredients described herein with other chemical components such as physiologically suitable carriers and excipients. The purpose of a pharmaceutical composition is to facilitate administration of a compound to an organism.

In another embodiment, "active ingredient" refers to the polypeptide sequence of interest, which is accountable for the biological effect.

In another embodiment, any of the compositions of this invention will comprise at least one CTP sequence bound only to the carboxy terminus a engineered coagulation factor of interest, in any form. In one embodiment, the present invention provides combined preparations. In one embodiment, "a combined preparation" defines especially a "kit of parts" in the sense that the combination partners as defined above can be dosed independently or by use of different fixed combinations with distinguished amounts of the combination partners i.e., simultaneously, concurrently, separately or sequentially. In some embodiments, the parts of the kit of parts can then, e.g., be administered simultaneously or chronologically staggered, that is at different time points and with equal or different time intervals for any part of the kit of parts. The ratio of the total amounts of the combination partners, in some embodiments, can be administered in the combined preparation. In one embodiment, the combined preparation can be varied, e.g., in order to cope with the needs of a patient subpopulation to be treated or the needs of the single patient which different needs can be due to a particular disease, severity of a disease, age, sex, or body weight as can be readily made by a person skilled in the art.

In another embodiment, the phrases "physiologically acceptable carrier" and "pharmaceutically acceptable carrier" which be interchangeably used refer to a carrier or a diluent that does not cause significant irritation to an organism and does not abrogate the biological activity and properties of the administered compound. An adjuvant is included under these phrases. In one embodiment, one of the ingredients included in the pharmaceutically acceptable carrier can be for example polyethylene glycol (PEG), a biocompatible polymer with a wide range of solubility in both organic and aqueous media (Mutter et al. (1979).

In another embodiment, "excipient" refers to an inert substance added to a pharmaceutical composition to further facilitate administration of an active ingredient. In one embodiment, excipients include calcium carbonate, calcium phosphate, various sugars and types of starch, cellulose derivatives, gelatin, vegetable oils and polyethylene glycols.

Techniques for formulation and administration of drugs are found in "Remington's Pharmaceutical Sciences," Mack Publishing Co., Easton, Pa., latest edition, which is incorporated herein by reference.

In another embodiment, suitable routes of administration, for example, include oral, rectal, transmucosal, transnasal, intestinal or parenteral delivery, including intramuscular, subcutaneous and intramedullary injections as well as intrathecal, direct intraventricular, intravenous, intraperitoneal, intranasal, or intraocular injections.

In another embodiment, the preparation is administered in a local rather than systemic manner, for example, via injection of the preparation directly into a specific region of a patient's body.

Various embodiments of dosage ranges are contemplated by this invention. The dosage of the engineered coagulation factor of the present invention, in one embodiment, is in the range of 0.005-100 mg/day. In another embodiment, the dosage is in the range of 0.005-5 mg/day. In another embodiment, the dosage is in the range of 0.01-50 mg/day. In another embodiment, the dosage is in the range of 0.1-20 mg/day. In another embodiment, the dosage is in the range of 0.1-10 mg/day. In another embodiment, the dosage is in the range of 0.01-5 mg/day. In another embodiment, the dosage is in the range of 0.001-0.01 mg/day. In another embodiment, the dosage is in the range of 0.001-0.1 mg/day. In another embodiment, the dosage is in the range of 0.1-5 mg/day. In another embodiment, the dosage is in the range of 0.5-50 mg/day. In another embodiment, the dosage is in the range of 0.2-15 mg/day. In another embodiment, the dosage is in the range of 0.8-65 mg/day. In another embodiment, the dosage is in the range of 1-50 mg/day. In another embodiment, the dosage is in the range of 5-10 mg/day. In another embodiment, the dosage is in the range of 8-15 mg/day. In another embodiment, the dosage is in a range of 10-20 mg/day. In another embodiment, the dosage is in the range of 20-40 mg/day. In another embodiment, the dosage is in a range of 60-120 mg/day. In another embodiment, the dosage is in the range of 12-40 mg/day. In another embodiment, the dosage is in the range of 40-60 mg/day. In another embodiment, the dosage is in a range of 50-100 mg/day. In another embodiment, the dosage is in a range of 1-60 mg/day. In another embodiment, the dosage is in the range of 15-25 mg/day. In another embodiment, the dosage is in the range of 5-10 mg/day. In another embodiment, the dosage is in the range of 55-65 mg/day.

In another embodiment, a polypeptide comprising a coagulation factor and at least one CTP unit is formulated in an intranasal dosage form. In another embodiment, a polypeptide comprising a coagulation factor and at least one CTP unit is formulated in an injectable dosage form. In another embodiment, a polypeptide comprising a coagulation factor and at least one CTP unit is administered to a subject in a dose ranging from 0.0001 mg to 0.6 mg. In another embodiment, a polypeptide comprising a coagulation factor and at least one CTP unit is administered to a subject in a dose ranging from 0.001 mg to 0.005 mg. In another embodiment, a polypeptide comprising a coagulation factor and at least one CTP unit is administered to a subject in a dose ranging from 0.005 mg to 0.01 mg. In another embodiment, a polypeptide comprising a coagulation factor and at least one CTP unit is administered to a subject in a dose ranging from 0.01 mg to 0.3 mg. In another embodiment, a polypeptide comprising a coagulation factor and at least one CTP unit is administered to a subject in a dose in a dose ranging from 0.2 mg to 0.6 mg. In another embodiment, a coagulation factor is free of CTPs on its amino terminus.

In another embodiment, a polypeptide comprising a coagulation factor and at least one CTP unit is administered to a subject in a dose ranging from 1-100 micrograms. In another embodiment, a polypeptide comprising a coagulation factor and at least one CTP unit is administered to a subject in a dose ranging from 10-80 micrograms. In another embodiment, a polypeptide comprising a coagulation factor and at least one CTP unit is administered to a subject in a dose ranging from 20-60 micrograms. In another embodiment, a polypeptide comprising a coagulation factor and at least one CTP unit is administered to a subject in a dose ranging from 10-50 micrograms. In another embodiment, a polypeptide comprising a coagulation factor and at least one CTP unit is administered to a subject in a dose ranging from 40-80 micrograms. In another embodiment, a polypeptide comprising a coagulation factor and at least one CTP unit is administered to a subject in a dose ranging from 10-30 micrograms. In another embodiment, a polypeptide comprising a coagulation factor and at least one CTP unit is administered to a subject in a dose ranging from 30-60 micrograms.

In another embodiment, a polypeptide comprising a coagulation factor and at least one CTP unit is administered to a subject in a dose ranging from 0.2 mg to 2 mg. In another embodiment, a polypeptide comprising a coagulation factor and at least one CTP unit is administered to a subject in a dose ranging from 2 mg to 6 mg. In another embodiment, a polypeptide comprising a coagulation factor and at least one CTP unit is administered to a subject in a dose ranging from 4 mg to 10 mg. In another embodiment, a polypeptide comprising a coagulation factor and at least one CTP unit is administered to a subject in a dose ranging from 5 mg and 15 mg.

In another embodiment, a polypeptide comprising a coagulation factor and at least one CTP unit is injected into the muscle (intramuscular injection). In another embodiment, a polypeptide comprising a coagulation factor and at least one CTP unit is injected below the skin (subcutaneous injection). In another embodiment, a polypeptide comprising an IFN protein and CTP units is injected into the muscle. In another embodiment, a polypeptide comprising an IFN protein and CTP units is injected below the skin.

In another embodiment, the methods of the invention include increasing the compliance in the use of coagulation factor therapy, comprising providing to a subject in need thereof, a polypeptide comprising a coagulation factor, one chorionic gonadotrophin carboxy terminal peptide (CTP)

attached to an amino terminus of the coagulation factor, and two chorionic gonadotrophin carboxy terminal peptides attached to a carboxy terminus of the coagulation factor, thereby increasing compliance in the use of coagulation factor therapy.

In another embodiment, the methods of the invention include increasing the compliance of patients afflicted with chronic illnesses that are in need of a coagulation factor therapy. In another embodiment, the methods of the invention enable reduction in the dosing frequency of a coagulation factor by modifying the coagulation factor with CTPs as described hereinabove. In another embodiment, the term compliance comprises adherence. In another embodiment, the methods of the invention include increasing the compliance of patients in need of a coagulation factor therapy by reducing the frequency of administration of the coagulation factor. In another embodiment, reduction in the frequency of administration of the coagulation factor is achieved due to the CTP modifications which render the CTP-modified coagulation factor more stable. In another embodiment, reduction in the frequency of administration of the coagulation factor is achieved as a result of increasing T1/2 of the coagulation factor. In another embodiment, reduction in the frequency of administration of the coagulation factor is achieved as a result of increasing the clearance time of the coagulation factor. In another embodiment, reduction in the frequency of administration of the coagulation factor is achieved as a result of increasing the AUC measure of the coagulation factor.

In another embodiment, provided a method of reducing a dosing frequency of a coagulation factor, comprising the step of attaching one to ten CTPs to a carboxy terminus of a coagulation factor, thereby reducing a dosing frequency of a coagulation factor. In another embodiment, provided a method of reducing a dosing frequency of a coagulation factor, comprising the step of attaching one to five CTPs to a carboxy terminus of a coagulation factor, thereby reducing a dosing frequency of a coagulation factor.

In another embodiment, provided a method of increasing compliance in the use of coagulation factor therapy, comprising providing to a subject in need thereof, a polypeptide comprising a coagulation factor and one to ten chorionic gonadotrophin carboxy terminal peptides attached to a carboxy terminus of a coagulation factor, thereby increasing compliance in the use of coagulation factor therapy. In another embodiment, provided a method of increasing compliance in the use of coagulation factor therapy, comprising providing to a subject in need thereof, a polypeptide comprising a coagulation factor and one to five chorionic gonadotrophin carboxy terminal peptides attached to a carboxy terminus of a coagulation factor, thereby increasing compliance in the use of coagulation factor therapy.

In another embodiment, a polypeptide comprising a coagulation factor and at least one CTP unit is administered to a subject once a day. In another embodiment, a polypeptide comprising a coagulation factor and at least one CTP unit is administered to a subject once every two days. In another embodiment, a polypeptide comprising a coagulation factor and at least one CTP unit is administered to a subject once every three days. In another embodiment, a polypeptide comprising a coagulation factor and at least one CTP unit is administered to a subject once every four days. In another embodiment, a polypeptide comprising a coagulation factor and at least one CTP unit is administered to a subject once every five days. In another embodiment, a polypeptide comprising a coagulation factor and at least one CTP unit is administered to a subject once every six days. In another embodiment, a polypeptide comprising a coagulation factor and at least one CTP unit is administered to a subject once every week. In another embodiment, a polypeptide comprising a coagulation factor and at least one CTP unit is administered to a subject once every 7-14 days. In another embodiment, a polypeptide comprising a coagulation factor and at least one CTP unit is administered to a subject once every 10-20 days. In another embodiment, a polypeptide comprising a coagulation factor and at least one CTP unit is administered to a subject once every 5-15 days. In another embodiment, a polypeptide comprising a coagulation factor and at least one CTP unit is administered to a subject once every 15-30 days.

In another embodiment, the dosage is in a range of 50-500 mg/day. In another embodiment, the dosage is in a range of 50-150 mg/day. In another embodiment, the dosage is in a range of 100-200 mg/day. In another embodiment, the dosage is in a range of 150-250 mg/day. In another embodiment, the dosage is in a range of 200-300 mg/day. In another embodiment, the dosage is in a range of 250-400 mg/day. In another embodiment, the dosage is in a range of 300-500 mg/day. In another embodiment, the dosage is in a range of 350-500 mg/day.

In one embodiment, the dosage is 20 mg/day. In one embodiment, the dosage is 30 mg/day. In one embodiment, the dosage is 40 mg/day. In one embodiment, the dosage is 50 mg/day. In one embodiment, the dosage is 0.01 mg/day. In another embodiment, the dosage is 0.1 mg/day. In another embodiment, the dosage is 1 mg/day. In another embodiment, the dosage is 0.530 mg/day. In another embodiment, the dosage is 0.05 mg/day. In another embodiment, the dosage is 50 mg/day. In another embodiment, the dosage is 10 mg/day. In another embodiment, the dosage is 20-70 mg/day. In another embodiment, the dosage is 5 mg/day.

In another embodiment, the dosage is 1-90 mg/day. In another embodiment, the dosage is 1-90 mg/2 days. In another embodiment, the dosage is 1-90 mg/3 days. In another embodiment, the dosage is 1-90 mg/4 days. In another embodiment, the dosage is 1-90 mg/5 days. In another embodiment, the dosage is 1-90 mg/6 days. In another embodiment, the dosage is 1-90 mg/week. In another embodiment, the dosage is 1-90 mg/9 days. In another embodiment, the dosage is 1-90 mg/11 days. In another embodiment, the dosage is 1-90 mg/14 days.

In another embodiment, the coagulation factor dosage is 10-50 mg/day. In another embodiment, the dosage is 10-50 mg/2 days. In another embodiment, the dosage is 10-50 mg/3 days. In another embodiment, the dosage is 10-50 mg/4 days. In another embodiment, the dosage is 10-50 micrograms mg/5 days. In another embodiment, the dosage is 10-50 mg/6 days. In another embodiment, the dosage is 10-50 mg/week. In another embodiment, the dosage is 10-50 mg/9 days. In another embodiment, the dosage is 10-50 mg/11 days. In another embodiment, the dosage is 10-50 mg/14 days.

Oral administration, in one embodiment, comprises a unit dosage form comprising tablets, capsules, lozenges, chewable tablets, suspensions, emulsions and the like. Such unit dosage forms comprise a safe and effective amount of the desired coagulation factor of the invention, each of which is in one embodiment, from about 0.7 or 3.5 mg to about 280 mg/70 kg, or in another embodiment, about 0.5 or 10 mg to about 210 mg/70 kg. The pharmaceutically-acceptable carriers suitable for the preparation of unit dosage forms for peroral administration are well-known in the art. In some embodiments, tablets typically comprise conventional pharmaceutically-compatible adjuvants as inert diluents, such as calcium carbonate, sodium carbonate, mannitol, lactose and cellulose; binders such as starch, gelatin and sucrose; disintegrants such as starch, alginic acid and croscarmelose; lubricants such as magnesium stearate, stearic acid and talc. In one embodiment, glidants such as silicon dioxide can be used to improve flow characteristics of the powder-mixture. In one embodiment, coloring agents, such as the FD&C dyes, can be added for appearance. Sweeteners and flavoring agents, such as aspartame, saccharin, menthol, peppermint, and fruit flavors, are useful adjuvants for chewable tablets. Capsules typically comprise one or more solid diluents disclosed above. In some embodiments, the selection of carrier components depends on secondary considerations like taste, cost, and shelf stability, which are not critical for the purposes of this invention, and can be readily made by a person skilled in the art.

In one embodiment, the oral dosage form comprises predefined release profile. In one embodiment, the oral dosage form of the present invention comprises an extended release tablets, capsules, lozenges or chewable tablets. In one embodiment, the oral dosage form of the present invention comprises a slow release tablets, capsules, lozenges or chewable tablets. In one embodiment, the oral dosage form of the present invention comprises an immediate release tablets, capsules, lozenges or chewable tablets. In one embodiment, the oral dosage form is formulated according to the desired release profile of the pharmaceutical active ingredient as known to one skilled in the art.

Peroral compositions, in some embodiments, comprise liquid solutions, emulsions, suspensions, and the like. In some embodiments, pharmaceutically-acceptable carriers suitable for preparation of such compositions are well known in the art. In some embodiments, liquid oral compositions comprise from about 0.001% to about 0.933% of the desired compound or compounds, or in another embodiment, from about 0.01% to about 10%.

In some embodiments, compositions for use in the methods of this invention comprise solutions or emulsions, which in some embodiments are aqueous solutions or emulsions comprising a safe and effective amount of the compounds of the present invention and optionally, other compounds, intended for topical intranasal administration. In some embodiments, h compositions comprise from about 0.001% to about 10.0% w/v of a subject compound, more preferably from about 00.1% to about 2.0, which is used for systemic delivery of the compounds by the intranasal route.

In another embodiment, the pharmaceutical compositions are administered by intravenous, intra-arterial, or intramuscular injection of a liquid preparation. In some embodiments, liquid formulations include solutions, suspensions, dispersions, emulsions, oils and the like. In one embodiment, the pharmaceutical compositions are administered intravenously, and are thus formulated in a form suitable for intravenous administration. In another embodiment, the pharmaceutical compositions are administered intra-arterially, and are thus formulated in a form suitable for intra-arterial administration. In another embodiment, the pharmaceutical compositions are administered intramuscularly, and are thus formulated in a form suitable for intramuscular administration.

Further, in another embodiment, the pharmaceutical compositions are administered topically to body surfaces, and are thus formulated in a form suitable for topical administration. Suitable topical formulations include gels, ointments, creams, lotions, drops and the like. For topical administration, the compounds of the present invention are combined with an additional appropriate therapeutic agent or agents, prepared and applied as solutions, suspensions, or emulsions in a physiologically acceptable diluent with or without a pharmaceutical carrier.

In one embodiment, pharmaceutical compositions of the present invention are manufactured by processes well known in the art, e.g., by means of conventional mixing, dissolving, granulating, dragee-making, levigating, emulsifying, encapsulating, entrapping or lyophilizing processes.

In one embodiment, pharmaceutical compositions for use in accordance with the present invention is formulated in conventional manner using one or more physiologically acceptable carriers comprising excipients and auxiliaries, which facilitate processing of the active ingredients into preparations which, can be used pharmaceutically. In one embodiment, formulation is dependent upon the route of administration chosen.

In one embodiment, injectables, of the invention are formulated in aqueous solutions. In one embodiment, injectables, of the invention are formulated in physiologically compatible buffers such as Hank's solution, Ringer's solution, or physiological salt buffer. In some embodiments, for transmucosal administration, penetrants appropriate to the barrier to be permeated are used in the formulation. Such penetrants are generally known in the art.

In one embodiment, the preparations described herein are formulated for parenteral administration, e.g., by bolus injection or continuous infusion. In some embodiments, formulations for injection are presented in unit dosage form, e.g., in ampoules or in multidose containers with optionally, an added preservative. In some embodiments, compositions are suspensions, solutions or emulsions in oily or aqueous vehicles, and contain formulatory agents such as suspending, stabilizing and/or dispersing agents.

The compositions also comprise, in some embodiments, preservatives, such as benzalkonium chloride and thimerosal and the like; chelating agents, such as edetate sodium and others; buffers such as phosphate, citrate and acetate; tonicity agents such as sodium chloride, potassium chloride, glycerin, mannitol and others; antioxidants such as ascorbic acid, acetylcystine, sodium metabisulfote and others; aromatic agents; viscosity adjustors, such as polymers, including cellulose and derivatives thereof; and polyvinyl alcohol and acid and bases to adjust the pH of these aqueous compositions as needed. The compositions also comprise, in some embodiments, local anesthetics or other actives. The compositions can be used as sprays, mists, drops, and the like.

In some embodiments, pharmaceutical compositions for parenteral administration include aqueous solutions of the active preparation in water-soluble form. Additionally, suspensions of the active ingredients, in some embodiments, are prepared as appropriate oily or water based injection suspensions. Suitable lipophilic solvents or vehicles include, in some embodiments, fatty oils such as sesame oil, or synthetic fatty acid esters such as ethyl oleate, triglycerides or liposomes. Aqueous injection suspensions contain, in some embodiments, substances, which increase the viscosity of the suspension, such as sodium carboxymethyl cellulose, sorbitol or dextran. In another embodiment, the suspension also contain suitable stabilizers or agents which increase the solubility of the active ingredients to allow for the preparation of highly concentrated solutions.

In another embodiment, the active compound can be delivered in a vesicle, in particular a liposome (see Langer, *Science* 249:1527-1533 (1990); Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327; see generally ibid).

In another embodiment, the pharmaceutical composition delivered in a controlled release system is formulated for intravenous infusion, implantable osmotic pump, transdermal patch, liposomes, or other modes of administration. In one embodiment, a pump is used (see Langer, supra; Sefton, CRC Crit. Ref. *Biomed. Eng.* 14:201 (1987); Buchwald et al., Surgery 88:507 (1980); Saudek et al., *N. Engl. J. Med.* 321: 574 (1989). In another embodiment, polymeric materials can be used. In yet another embodiment, a controlled release system can be placed in proximity to the therapeutic target, i.e., the brain, thus requiring only a fraction of the systemic dose (see, e.g., Goodson, in *Medical Applications of Controlled Release*, supra, vol. 2, pp. 115-138 (1984). Other controlled release systems are discussed in the review by Langer (Science 249:1527-1533 (1990).

In some embodiments, the active ingredient is in powder form for constitution with a suitable vehicle, e.g., sterile, pyrogen-free water based solution, before use. Compositions are formulated, in some embodiments, for atomization and inhalation administration. In another embodiment, compositions are contained in a container with attached atomizing means.

In one embodiment, the preparation of the present invention is formulated in rectal compositions such as suppositories or retention enemas, using, e.g., conventional suppository bases such as cocoa butter or other glycerides.

In some embodiments, pharmaceutical compositions suitable for use in context of the present invention include compositions wherein the active ingredients are contained in an amount effective to achieve the intended purpose. In some embodiments, a therapeutically effective amount means an amount of active ingredients effective to prevent, alleviate or ameliorate symptoms of disease or prolong the survival of the subject being treated.

In one embodiment, determination of a therapeutically effective amount is well within the capability of those skilled in the art.

Some examples of substances which can serve as pharmaceutically-acceptable carriers or components thereof are sugars, such as lactose, glucose and sucrose; starches, such as corn starch and potato starch; cellulose and its derivatives, such as sodium carboxymethyl cellulose, ethyl cellulose, and methyl cellulose; powdered tragacanth; malt; gelatin; talc; solid lubricants, such as stearic acid and magnesium stearate; calcium sulfate; vegetable oils, such as peanut oil, cottonseed oil, sesame oil, olive oil, corn oil and oil of *theobroma*; polyols such as propylene glycol, glycerine, sorbitol, mannitol, and polyethylene glycol; alginic acid; emulsifiers, such as the Tween™ brand emulsifiers; wetting agents, such sodium lauryl sulfate; coloring agents; flavoring agents; tableting agents, stabilizers; antioxidants; preservatives; pyrogen-free water; isotonic saline; and phosphate buffer solutions. The choice of a pharmaceutically-acceptable carrier to be used in conjunction with the compound is basically determined by the way the compound is to be administered. If the subject compound is to be injected, in one embodiment, the pharmaceutically-acceptable carrier is sterile, physiological saline, with a blood-compatible suspending agent, the pH of which has been adjusted to about 7.4.

In addition, the compositions further comprise binders (e.g. acacia, cornstarch, gelatin, carbomer, ethyl cellulose, guar gum, hydroxypropyl cellulose, hydroxypropyl methyl cellulose, povidone), disintegrating agents (e.g. cornstarch, potato starch, alginic acid, silicon dioxide, croscarmelose sodium, crospovidone, guar gum, sodium starch glycolate), buffers (e.g., Tris-HCl., acetate, phosphate) of various pH and ionic strength, additives such as albumin or gelatin to prevent absorption to surfaces, detergents (e.g., Tween 20, Tween 80, Pluronic F68, bile acid salts), protease inhibitors, surfactants (e.g. sodium lauryl sulfate), permeation enhancers, solubilizing agents (e.g., glycerol, polyethylene glycerol), anti-oxidants (e.g., ascorbic acid, sodium metabisulfite, butylated hydroxyanisole), stabilizers (e.g. hydroxypropyl cellulose, hyroxypropylmethyl cellulose), viscosity increasing agents (e.g. carbomer, colloidal silicon dioxide, ethyl cellulose, guar gum), sweeteners (e.g. aspartame, citric acid), preservatives (e.g., Thimerosal, benzyl alcohol, parabens), lubricants (e.g. stearic acid, magnesium stearate, polyethylene glycol, sodium lauryl sulfate), flow-aids (e.g. colloidal silicon dioxide), plasticizers (e.g. diethyl phthalate, triethyl citrate), emulsifiers (e.g. carbomer, hydroxypropyl cellulose, sodium lauryl sulfate), polymer coatings (e.g., poloxamers or poloxamines), coating and film forming agents (e.g. ethyl cellulose, acrylates, polymethacrylates) and/or adjuvants.

Typical components of carriers for syrups, elixirs, emulsions and suspensions include ethanol, glycerol, propylene glycol, polyethylene glycol, liquid sucrose, sorbitol and water. For a suspension, typical suspending agents include methyl cellulose, sodium carboxymethyl cellulose, cellulose (e.g. Avicel™, RC-591), tragacanth and sodium alginate; typical wetting agents include lecithin and polyethylene oxide sorbitan (e.g. polysorbate 80). Typical preservatives include methyl paraben and sodium benzoate. In another embodiment, peroral liquid compositions also contain one or more components such as sweeteners, flavoring agents and colorants disclosed above.

The compositions also include incorporation of the active material into or onto particulate preparations of polymeric compounds such as polylactic acid, polglycolic acid, hydrogels, etc, or onto liposomes, microemulsions, micelles, unilamellar or multilamellar vesicles, erythrocyte ghosts, or spheroplasts.) Such compositions will influence the physical state, solubility, stability, rate of in-vivo release, and rate of in-vivo clearance.

Also comprehended by the invention are particulate compositions coated with polymers (e.g. poloxamers or poloxamines) and the compound coupled to antibodies directed against tissue-specific receptors, ligands or antigens or coupled to ligands of tissue-specific receptors.

In some embodiments, compounds modified by the covalent attachment of water-soluble polymers such as polyethylene glycol, copolymers of polyethylene glycol and polypropylene glycol, carboxymethyl cellulose, dextran, polyvinyl alcohol, polyvinylpyrrolidone or polyproline. In another embodiment, the modified compounds exhibit substantially longer half-lives in blood following intravenous injection than do the corresponding unmodified compounds. In one embodiment, modifications also increase the compound's solubility in aqueous solution, eliminate aggregation, enhance the physical and chemical stability of the compound, and greatly reduce the immunogenicity and reactivity of the compound. In another embodiment, the desired in-vivo biological activity is achieved by the administration of such polymer-compound abducts less frequently or in lower doses than with the unmodified compound.

In some embodiments, preparation of effective amount or dose can be estimated initially from in-vitro assays. In one embodiment, a dose can be formulated in animal models and such information can be used to more accurately determine useful doses in humans.

In one embodiment, toxicity and therapeutic efficacy of the active ingredients described herein can be determined by standard pharmaceutical procedures in vitro, in cell cultures or experimental animals. In one embodiment, the data obtained from these in-vitro and cell culture assays and animal studies can be used in formulating a range of dosage for use in human. In one embodiment, the dosages vary depending upon the dosage form employed and the route of administration utilized. In one embodiment, the exact formulation, route of administration and dosage can be chosen by the individual physician in view of the patient's condition. [See e.g., Fingl, et al., (1975) "The Pharmacological Basis of Therapeutics", Ch. 1 p. 1].

In one embodiment, depending on the severity and responsiveness of the condition to be treated, dosing can be of a single or a plurality of administrations, with course of treatment lasting from several days to several weeks or until cure is effected or diminution of the disease state is achieved.

In one embodiment, the amount of a composition to be administered will, of course, be dependent on the subject being treated, the severity of the affliction, the manner of administration, the judgment of the prescribing physician, etc.

In one embodiment, compositions including the preparation of the present invention formulated in a compatible pharmaceutical carrier are also be prepared, placed in an appropriate container, and labeled for treatment of an indicated condition.

In another embodiment, a coagulation factor as described herein is administered via systemic administration. In another embodiment, a coagulation factor as described herein is administered by intravenous, intramuscular or subcutaneous injection. In another embodiment, a coagulation factor as described herein is lyophilized (i.e., freeze-dried) preparation in combination with complex organic excipients and stabilizers such as nonionic surface active agents (i.e., surfactants), various sugars, organic polyols and/or human serum albumin. In another embodiment, a pharmaceutical composition comprises a lyophilized coagulation factor as described in sterile water for injection. In another embodiment, a pharmaceutical composition comprises a lyophilized coagulation factor as described in sterile PBS for injection. In another embodiment, a pharmaceutical composition comprises a lyophilized coagulation factor as described in sterile 0.9% NaCl for injection.

In another embodiment, the pharmaceutical composition comprises a coagulation factor as described herein and complex carriers such as human serum albumin, polyols, sugars, and anionic surface active stabilizing agents. See, for example, WO 89/10756 (Hara et al.—containing polyol and p-hydroxybenzoate). In another embodiment, the pharmaceutical composition comprises a coagulation factor as described herein and lactobionic acid and an acetate/glycine buffer. In another embodiment, the pharmaceutical composition comprises a coagulation factor as described herein and amino acids, such as arginine or glutamate that increase the solubility of interferon compositions in water. In another embodiment, the pharmaceutical composition comprises a lyophilized coagulation factor as described herein and glycine or human serum albumin (HSA), a buffer (e.g. acetate) and an isotonic agent (e.g NaCl). In another embodiment, the pharmaceutical composition comprises a lyophilized coagulation factor as described herein and phosphate buffer, glycine and HSA.

In another embodiment, the pharmaceutical composition comprising a coagulation factor as described herein is stabilized when placed in buffered solutions having a pH between about 4 and 7.2. In another embodiment, the pharmaceutical composition comprising a coagulation factor as described herein is stabilized with an amino acid as a stabilizing agent and in some cases a salt (if the amino acid does not contain a charged side chain).

In another embodiment, the pharmaceutical composition comprising a coagulation factor as described herein is a liquid composition comprising a stabilizing agent at between about 0.3% and 5% by weight which is an amino acid.

In another embodiment, the pharmaceutical composition comprising a coagulation factor as described herein provides dosing accuracy and product safety. In another embodiment, the pharmaceutical composition comprising a coagulation factor as described herein provides a biologically active, stable liquid formulation for use in injectable applications. In another embodiment, the pharmaceutical composition comprises a non-lyophilized coagulation factor as described herein.

In another embodiment, the pharmaceutical composition comprising a coagulation factor as described herein provides a liquid formulation permitting storage for a long period of time in a liquid state facilitating storage and shipping prior to administration.

In another embodiment, the pharmaceutical composition comprising a coagulation factor as described herein comprises solid lipids as matrix material. In another embodiment, the injectable pharmaceutical composition comprising a coagulation factor as described herein comprises solid lipids as matrix material. In another embodiment, the production of lipid microparticles by spray congealing was described by Speiser (Speiser and al., Pharm. Res. 8 (1991) 47-54) followed by lipid nanopellets for peroral administration (Speiser EP 0167825 (1990)). In another embodiment, lipids, which are used, are well tolerated by the body (e.g. glycerides composed of fatty acids which are present in the emulsions for parenteral nutrition).

In another embodiment, the pharmaceutical composition comprising a coagulation factor as described herein is in the form of liposomes (J. E. Diederichs and al., Pharm./nd. 56 (1994) 267-275).

In another embodiment, the pharmaceutical composition comprising a coagulation factor as described herein comprises polymeric microparticles. In another embodiment, the injectable pharmaceutical composition comprising a coagulation factor as described herein comprises polymeric microparticles. In another embodiment, the pharmaceutical composition comprising a coagulation factor as described herein comprises nanoparticles. In another embodiment, the pharmaceutical composition comprising a coagulation factor as described herein comprises liposomes. In another embodiment, the pharmaceutical composition comprising a coagulation factor as described herein comprises lipid emulsion. In another embodiment, the pharmaceutical composition comprising a coagulation factor as described herein comprises microspheres. In another embodiment, the pharmaceutical composition comprising a coagulation factor as described herein comprises lipid nanoparticles. In another embodiment, the pharmaceutical composition comprising a coagulation factor as described herein comprises lipid nanoparticles comprising amphiphilic lipids. In another embodiment, the pharmaceutical composition comprising a coagulation factor as described herein comprises lipid nanoparticles comprising a drug, a lipid matrix and a surfactant. In another embodiment, the lipid matrix has a monoglyceride content which is at least 50% w/w.

In one embodiment, compositions of the present invention are presented in a pack or dispenser device, such as an FDA approved kit, which contain one or more unit dosage forms containing the active ingredient. In one embodiment, the pack, for example, comprise metal or plastic foil, such as a blister pack. In one embodiment, the pack or dispenser device is accompanied by instructions for administration. In one embodiment, the pack or dispenser is accommodated by a notice associated with the container in a form prescribed by a governmental agency regulating the manufacture, use or sale of pharmaceuticals, which notice is reflective of approval by the agency of the form of the compositions or human or veterinary administration. Such notice, in one embodiment, is labeling approved by the U.S. Food and Drug Administration for prescription drugs or of an approved product insert.

In one embodiment, it will be appreciated that the coagulation factors of the present invention can be provided to the individual with additional active agents to achieve an improved therapeutic effect as compared to treatment with each agent by itself. In another embodiment, measures (e.g., dosing and selection of the complementary agent) are taken to adverse side effects which are associated with combination therapies.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N.Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference. Other general references are provided throughout this document.

Example 1

Generation and Utilization of Coagulation Factor IX

Factor IX (FIX) is a 415 Amino acid (55 KDa) glycoprotein; it belongs to a group of vitamin K dependent glycolproteins associated with the coagulation system. FIX has a similar domain organization as factor FVII, factor X, protein C and prothrombin that are synthesized as precursors with N-terminal propeptide followed by a mature amino acid sequence.

FIX is secreted as a single chain molecule that undergoes complex post transcriptional modifications many which are critical to its biochemical and pharmacokinetic properties. Among all the post transcriptional modifications, 12 glutamic acid residues near the amino terminus of FIX that are gamma carboxylated by the vitamin K dependent gamma carboxylase are the most crucial ones. Carboxylation is required for the interaction of FIX with the phospholipids surfaces and for optimal FIX activity. The amino terminus propeptide serves as a recognition site for the gamma carboxylase and thus following the gamma carboxylation it is cleaved off by the Golgi apparatus serine protease known as Paired basic Amino acid Cleave Enzyme (PACE/Furin). Four additional post transcriptional modifications occur at the Golgi apparatus, sulfation of tyrosine 155, phosphorylation of serine 158, O-glycosylation on Ser 63 and on 61 and finally N-glycosylation on Asn 157 and 16.

FIX circulates in the plasma (average concentration of 5 μg/ml) as a single chain inactive zymogen. Upon proteolytic cleavage at two peptide bonds: Arg 145 and Arg 180 by either one or two physiological activators FVIIa-TF complex or FIXa, the activation peptide is removed converting FIX to a fully active enzyme consisting a light and heavy chain held together by a single disulfide bond. The N-terminal light chain contains the non catalytic gamma carboxglutamic acid (Gla) and two Epidrmal growth factor like domains while the C-terminal heavy chain contains the trypsin like catalytic domain of the molecule. FIXa alone is characterized by poor catalytic activity. However when complexed with FVIII, its proteolytic activity increase by 4-5 orders of magnitudes towards its natural substrate FX.

Hemophilia B is an X linked bleeding disorder caused by a mutation in the Factor IX (FIX) gene, resulting in a deficiency of the procoagulant activity of FIX. Hemophilia B patients have spontaneous soft tissue hemorrhages and recurrent hemarthroses that often lead to a crippling Arthoathy. Current treatment for these patients includes an intravenous administration of recombinant FIX. However issues of cost and relatively rapid clearance of FIX from the circulation makes developing a long acting FIX a challenging task.

The CTP technology was utilized for the development of a long acting FIX. Specifically, extending half life of recombinant rFIX molecule was performed by fusion of at least one human CTP to FIX. The recombinant FIX-CTP was expressed in mammalian cells and characterized in-vitro and in vivo. It was demonstrated that the in-vitro activity of rFIX-CTP was comparable to rFIX. Pharmacokinetics and efficacy studies in rats and demonstrated an improved properties of the rFIX-CTP. The results of this study demonstrate that it is feasible to develop a half life extended rFIX molecule having a similar haemostatic properties to the wild type enzyme Cloning and Expression of Recombinant FIX Molecule:

Dg44 cells were plated in 100 mm tissue culture dishes and grown to 50-60% confluence. A total of 2 μg (microgram) of FIX cDNA was used for the transfection of one 100 mm plate using the FuGene reagent (Roche) in protein free medium (Invitrogene CD Dg44). The media was removed 48 hours after transfection and replaced with a protein free medium (Invitrogene CD Dg44) without nucleosides and in the presence of 800 μg/ml of G418 (Neomycin). After 14 days the transfected cell population was transferred into T25 tissue culture flasks and selection continued for additional 10-14 days until the cells began to grow as stable clones. High expressing clones were selected. Approximately $2 \times 10^7$ cells were used to inoculate 300 ml of growth medium in a 1700 $cm^2$ roller bottle (Corning, Corning N.Y.) supplemented with 5 ng/ml of Vitamin K3 (menadione sodium bisulfate; Sigma). The production medium (harvest) was collected after a rapid decrease in cells viability to about 70%. The production medium was first clarified and then concentrated approximately 20 fold and dialyzed with PBS using flow filtration cassette (10 KDa MWCO; Millipore Corp.)

Figure 3A:
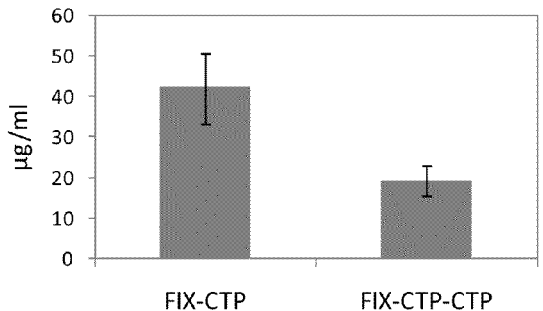
FIG. 3A is a bar graph showing harvests of limited diluted transfected and selected cells with FIX-CTP and FIX-CTP-CTP variants in the presence of 5 µg/ml of Vitamin K3. The level of FIX was quantified using Human FIX ELISA kit (Affinity Biologicals; cat. No. FIX-AG RUO), the calculated protein concentration (µg/ml) is the average of two independent runs.

Determination of FIX Antigen Level:

FIX-CTP harvests antigen levels were determined using AssayMax Human FIX ELISA kit (AssayPro-EF1009-1), the calculated protein concentration is the average of three different dilutions in two independent runs (FIG. 3A).

TABLE 1

Calculated protein concentration

|  | FIX-CTP | FIX-CTP-CTP |
| --- | --- | --- |
| FIX Ag level (μg/ml) | 41.9 | 19.2 |
| SD | 8.76 | 3.67 |
| % CV | 20.92 | 19.15 |

Figure 3B:
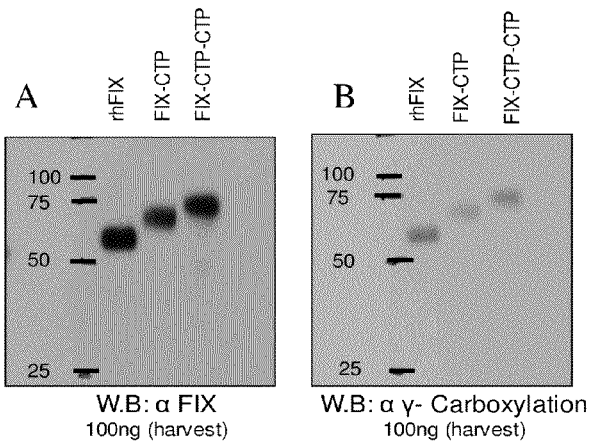
FIG. 3B depicts SDS-PAGE gel micrographs of FIX Ab recognition Micrograph A depicts recognition of anti-FIX antibody in Western-blot; Micrograph B depicts recognition of anti-γ carboxylation antibody in Western-blot. Lane 1 in A-B was loaded with a sample containing recombinant FIX Lane 2 in A-B was loaded with a sample containing FIX-CTP harvets. Lane 3 in A-B was loaded with a sample containing FIX-(CTP)$_2$ harvest.

FIX SDS-PAGE—Immune Blot:

FIX-CTP harvests or purified rhFIX (American Diagnostics), 100 ng of protein, were loaded on 12% Tris-Glycine gel using Precision plus dual color protein marker (Bio-Rad). The SDS-PAGE analysis was performed by western immuneblot using anti human FIX polyclonal Ab and anti human gamma carboxylation monoclonal antibody (American Diagnostics). As previously reported rhFIX migrated at 55 KDa, while FIX fused to two CTPs migrated at 75 KDa. Both variants of FIX-CTP proteins were shown to be gamma carboxylated (FIG. 3B).

Figure 4:
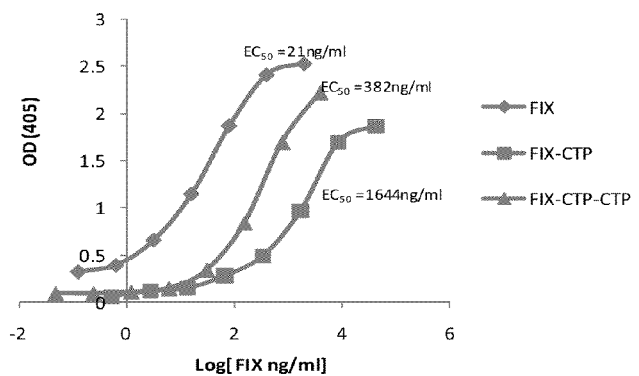
FIG. 4 is a graph showing FIX-CTP and FIX-(CTP)$_2$ harvests comparative chromogenic activity (measured by a the EC$_{50}$. concentration) compared to rhFIX (American Diagnostics).

Determination of FIX chromogenic activity: A comparative assessment of the in vitro potency of FIX-CTP harvests versus rhFIX-protein (American Diagnostics) was performed using a commercially available chromogenic activity test kit, BIOPHEN (Hyphen BioMed 221802). In the present of thrombin, phospholipids, calcium, excess amounts of FXIa activates sampled FIX into FIXa. FIXa forms an enzymatic complex with thrombin, activated FVIII:C (supplied in an excess amounts) phospholipids and calcium and activates factor X, present in the assay system, into FXa. The activity directly correlates to the amount of FIX, which is the limiting factor. The generated FXa is then measured by its specific activity on FXa chromogenic substrate (pNA). The amount of pNA generated is directly proportional to FIXa activity. rhFIX and FIX-CTP harvests were serially diluted and the potency was assessed by comparing a dose response curve of the FIX harvests to a reference preparation consisting rhFIX or human plasma. The average EC50 of FIX was 21 ng/ml while FIX-(CTP)$_2$ harvest calculated EC50 was 382 ng/ml, FIX-CTP harvest calculated EC50 was 1644 ng/ml. Approximately 15 fold decrease in the enzymatic activity of FIX-(CTP)$_2$ harvest was observed (FIG. 4).

FIX Clotting activity (aPTT): The activated partial thromboplastin time (aPTT) is a measure of the integrity of the intrinsic and common pathways of the coagulation cascade. The aPTT is the time, in seconds, for plasma to clot following the addition of an intrinsic pathway activator, phospholipid and calcium. The aPTT reagent is called a partial thromboplastin because tissue factor is not included with the phospholipid as it is with the protime (PT) reagent. The activator initiates the system, then, the remaining steps of the intrinsic pathway take place in the presence of phospholipid. Reference aPTT range varies from laboratory to laboratory, but is usually in the range of 27-34 seconds.

Figure 5:
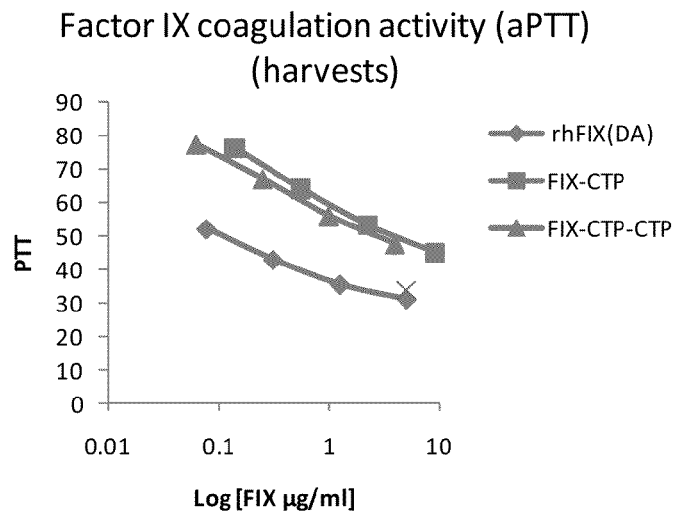
FIG. 5 is a graph showing FIX-CTP and FIX-(CTP) harvests coagulation activity compared to rhFIX (American Diagnostics) coagulation activity.

The principal of the assay was to quantitate the ability of FIX-CTP harvests to restore the clotting activity of FIX depleted human plasma by the addition of rhFIX. 300 μl of FIX deficient human plasma was mixed with 100 μl of rhFIX or FIX-CTP harvests and serially diluted. Following 60 seconds incubation at 37 C thromboplastin, CaCl2, and phospholipids were added to the mixture, clotting time in seconds was determined (performed by American Medical Laboratories). The potency was assessed by comparing a dose response curve of the FIX harvests to a reference preparation consisting rhFIX or human plasma, one unit of FIX activity is the needed FIX concentration that equals the activity of one ml human normal plasma; The presented aPTT results indicate that FIX-(CTP)$_2$ exhibit a 5.7 fold reduction in its specific coagulation activity compared to rhFIX. Moreover, the aPTT results together with the chromogenic activity in vitro assay suggest that FIX-(CTP)$_2$ harvest has an improved enzymatic activity vs. FIX-CTP harvest (FIG. 5). An improved activity of FIX-CTP proteins will be obtained following optimization of the expression system (i.e. co-transfection with Furin and optimization of Vit K3 medium concentration).

TABLE 2

FIX clotting activity

| rhFIX(AD) (μg/ml) | PTT (Sec) | FIX-CTP (μg/ml) | PTT (Sec) | FIX-CTP-CTP (μg/ml) | PTT (Sec) |
| --- | --- | --- | --- | --- | --- |
| 5 | 31.3 | 9 | 45.2 | 4 | 47.5 |
| 1.25 | 35.7 | 2.25 | 53.3 | 1 | 55.9 |
| 0.3125 | 43 | 0.5625 | 64.1 | 0.25 | 67 |
| 0.078125 | 52.1 | 0.140625 | 76.3 | 0.0625 | 77.4 |

Pharmacokinetic study: rhFIX (American Diagnostic), and FIX-CTP harvests were administered in a single intravenous injection to Sprague Dawley rats (six rats per substance) with a dose of 75 ug/kg body weight.

TABLE 3

PK study plan of operation

| Treated. Groups | Test Article | No. of animals/ group | Dose Route | Gender | Dose Level (µg/kg) | Dose Level (µg per animal) | Injected Vol. (µl) | Con. (□g/ml) | *Time-Points (hours post-dose) |
|---|---|---|---|---|---|---|---|---|---|
| 1 | rFIX | 6 | IV | M | 75 | 15 | 500 | 30 | 0 (Pre-dose) 0.083, 0.5, 1.5, 4, 8, 24, 48, 72. |
| 2 | rFIX-CTP | 6 | IV | M | 75 | 15 | 500 | 30 | 0 (Pre-dose) 0.083, 0.5, 1.5, 4, 8, 24, 48, 72. |
| 3 | rFIX-CTP-CTP | 6 | IV | M | 75 | 15 | 1000 | 15 | 0 (Pre-dose) 0.083, 0.5, 1.5, 4, 8, 24, 48, 72. |

Figure 6:
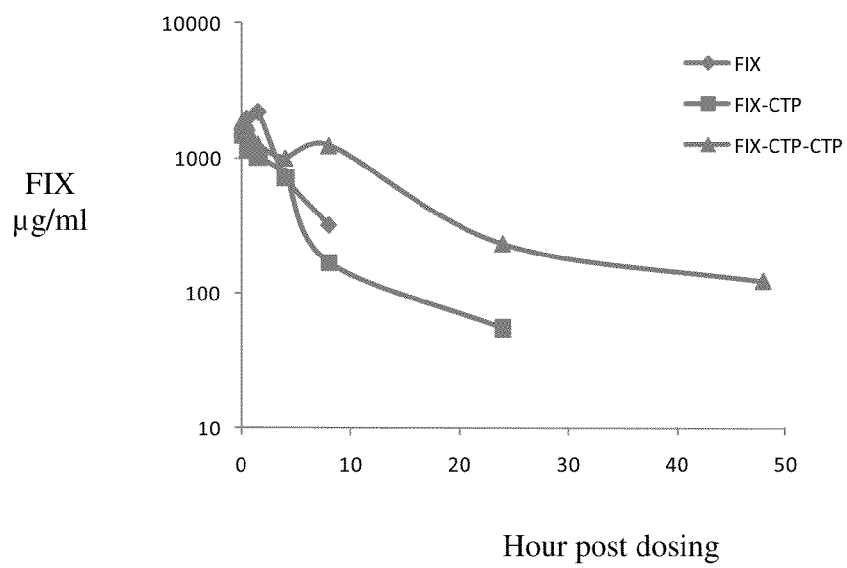
FIG. 6 is a graph showing PK profile of rhFIX, harvest of FIX-CTP-CTP, and harvest of FIX-CTP.

Blood samples were drawn retro-orbitaly from 3 Rats alternately at 0.083, 0.5 1.5, 4, 8, 24, 48, 72 hours post dosing. Plasma was prepared immediately after sampling and stored at −20 C until analysis. FIX concentration was quantitated by FIX Elisa specific assay (AssayPro), Pharmacokinetic profile was calculated for each protein and is the mean of 3 animals at each time point (FIG. 6), terminal half lives was calculated using PK solutions 2.0 software. Table 4 summarizes the observed FIX concentrations at the different sampling time points. PK profile and summary of the terminal half-lives are summarized in table 5.

TABLE 4

Summary of PK profile

| Time (Hr) | FIX-AD (ng/ml) | FIX-CTP (ng/ml) | FIX-CTP-CTP (ng/ml) |
|---|---|---|---|
| 0.083 | 1506.7 | 1477.5 | 1914.8 |
| 0.5 | 1949.8 | 1150.1 | 1830.1 |
| 1.5 | 2189.4 | 1009.0 | 1264.3 |
| 4 | 733.90 | 709.33 | 1000.00 |
| 8 | 319.80 | 167.20 | 1234.67 |
| 24 | BLQ | 54.625 | 230 |
| 48 | BLQ | BLQ | 120.9 |

FIX-CTP harvests exhibit an improved $T1/2_\beta$ values compared to rhFIX (2 and 5-fold increase respectively). Since in FIX dosing collection animals serum concentrations at 24 hr were below limit of quantitation (BLQ), additional PK parameters were not calculated.

TABLE 5

Summary of PK parameters

| Product | Terminal half life- (hr) | Ratio (MOD-301X/rhFIX) |
|---|---|---|
| rhFIX (American Diagnostics) | 2.62 | — |
| MOD-3011 (FIX-CTP) | 5.55 | 2.11 |
| MOD-3011 (FIX-CTP-CTP) | 12.9 | 4.92 |

In this study a novel approach was described for prolonging FIX half life while retaining the therapeutic potency. Adding a CTP peptide to an active protein has a harmful potential in interfering with the protein's activity, therefore, the generation of an active recombinant FIX-CTP by adding a CTP sequence at the C-terminus of the FIX is unexpected.

Characterization of an Immunoaffinity Purified FIX-CTP-CTP (MOD-3012)

MOD3012 Purification

MOD3012 is a FIX modified with 2 CTP units in tandem in its carboxy-terminal. MOD3012 was purified using matrix bound monoclonal antibody against γ carboxyglutamyl (Gla) residues present in the N-terminal region of FIX (American Diagnostics Cat#3570MX). The Monoclonal Ab was bound to Sepharose CL-4B. MOD3012 harvest in a concentration of 88 µg/ml was dialyzed against 20 mM Tris, 150 Mm NaCl and 10 mM EDTA at PH=7.4. The loading rate was 0.5 ml/min, elution was performed using 20 Mm Tris-HCl, 350 mM NaCl and 50 mM CaCl and the unbound fraction was recycled five times. Finally, the elution fraction was dialyzed with PBS, pulled and concentrated.

Determination of FIX Antigen Level

Figure 7:
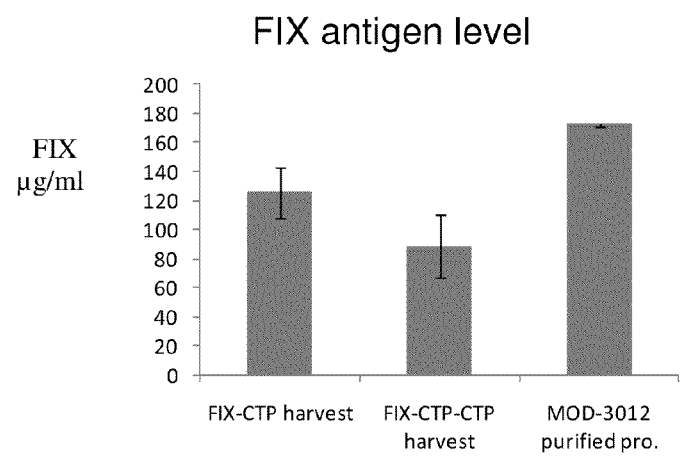
FIG. 7 is a bar graph showing harvests of FIX-CTP and FIX-CTP-CTP_MOD-3011 and MOD-3012, respectively harvests and MOD3012 purified protein FIX antigen level as determined using Human FIX ELISA kit (Affinity Biologicals; cat. No. FIX-AG RUO), the calculated protein concentration (μg/ml) is the average of two independent runs.

FIX-CTP and FIX-(CTP)$_2$; MOD-3011 and MOD-3012, respectively, harvests and MOD3012 purified protein levels were determined using the Human FIX ELISA kit (Affinity Biologicals; cat# FIX-AG RUO), the calculated protein concentration (µg/ml) is the average of two independent runs (FIG. 7).

TABLE 1

Calculated protein concentration

| | FIX-CTP | FIX-CTP-CTP | MOD3012 (purified) |
|---|---|---|---|
| FIX Ag level (µg/ml) | 125.78 | 88.53 | 172.9 |
| SD | 17.28 | 21.31 | 2.63 |
| % CV | 13.74 | 24.08 | 1.52 |

Additionally, MOD-3012 was quantitated by Bradford assay. The calculated concentration was 202 µg/ml, which is similar to the concentration obtained by human FIX ELISA.

SDS-PAGE Blots

Figure 8:
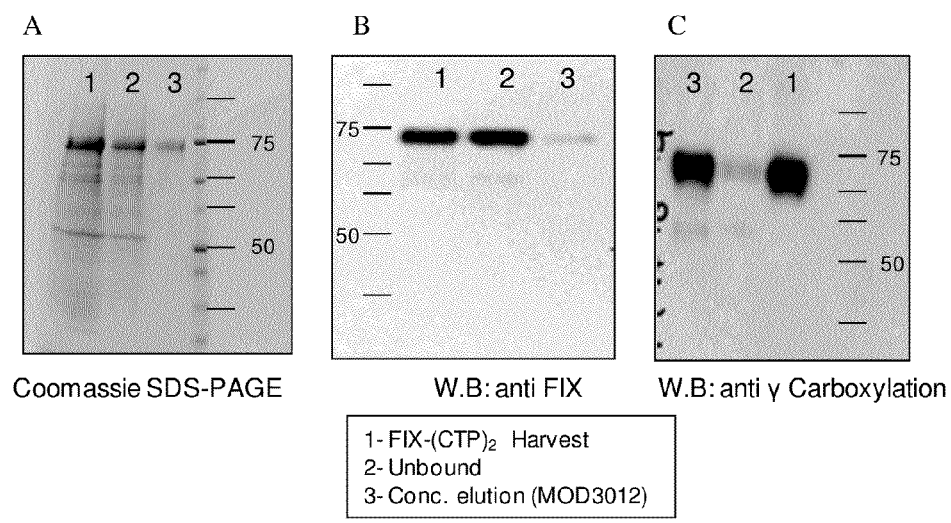
FIG. 8 depicts SDS-PAGE gel micrographs of FIX Ab recognition. Micrograph A depicts a coomassie blue staining; Micrograph B depicts recognition of anti-FIX antibody in Western-blot; Micrograph C depicts recognition of anti-γ carboxylation antibody in Western-blot. Lane 1 in A-C was loaded with a sample containing FIX-(CTP)$_2$ (MOD-3012). Lane 2 in A-C was loaded with a sample containing unbound FIX-(CTP)$_2$. Lane 3 in A-C was loaded with a sample containing a concentrated elution of FIX-(CTP)$_2$ (MOD-3012).

MOD3012 harvest, unbound fraction and purified protein, were loaded on 12% Tris-Glycine gel using Precision plus dual color protein marker (Bio-Rad). The SDS-PAGE Coomassie analysis was performed by staining the gel with Commasie blue reagent (800 ng of protein), western immunoblot was performed with (100 ng of protein) anti human FIX polyclonal antibody (Ab) and anti human gamma carboxylation monoclonal Ab (American Diagnostics Cat #499, 3570). The immunoaffinity purification procedure significantly enriched MOD3012 portion while reduced impurity (FIG. 8).

N-Terminal Sequencing:

MOD-3012 purified protein was separated by 12% Tris-Glycine SDS-PAGE and subsequently electro-blotted to PVDF membrane. The band of interest was cut out and put on a purified Biobrene treated glass fiber filter. The N-terminal sequence analysis was carried out by Edmann degradation using a pulsed liquid protein sequencer equipped with a 140 C HPLC micro-gradient system. N-terminal sequencing revealed the MOD3012 is a mixture of un-complete and complete pro peptide cleaved proteins. Inadequately pro peptide cleavage was shown to reduce FIX coagulation activity. By co-transfection with Furin an improved pro peptide cleavage process can be obtained.

Determination of FIX Chromogenic Activity

Figure 9:
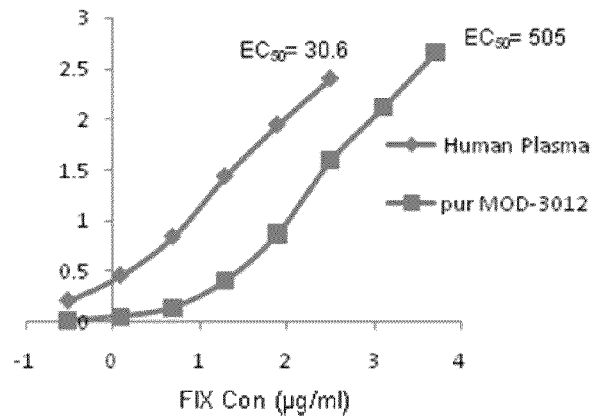
FIG. 9 is a graph showing MOD3012 Comparative chromogenic activity (sample concentration/O.D.) compared to human normal pool plasma and rhFIX (American Diagnostics).

A comparative assessment of the in-vitro potency of MOD-3012 purified protein versus rhFIX (American Diagnostics) and pool of human normal plasma was performed using a commercially available chromogenic activity test kit, BIOPHEN (Hyphen BioMed 221802). In the presence of thrombin, phospholipids and calcium; excess amounts of FXIa activated FIX into FIXa. FIXa formed an enzymatic complex with thrombin, (supplied in an excess amounts) phospholipids and calcium and activates factor X, present in the assay system, into FXa. The activity directly correlated with the amount of FIX, which is the limiting factor. The generated FXa was measured by its specific activity on FXa chromogenic substrate (pNA). The amount of pNA generated was directly proportional to FIXa activity. rhFIX, human plasma and MOD-3012 were serially diluted and potency was assessed by comparing a dose response curve (FIG. 9). The average $EC_{50}$ of rhFIX was 68.74 ng/ml while MOD-3012 calculated $EC_{50}$ was 505 ng/ml. Approximately 7 fold decrease in the enzymatic activity of MOD-3012 was observed vs. recombinant FIX and 16.5 fold decrease versus normal human pulled plasma. This reduced activity could be explained by inadequate cleavage of N-terminal pro-peptide, which was identified by N-terminal analysis.

FIX Clotting Activity (aPTT)

The activated partial thromboplastin time (aPTT) is a measure of the integrity of the intrinsic and common pathways of the coagulation cascade. The aPTT is the time (measured in seconds) it takes plasma to clot following the addition of an intrinsic pathway activator, phospholipid and calcium.

The assay quantitated the ability of MOD-3012 protein to restore the clotting activity of FIX depleted human plasma by the addition of rhFIX. 300 μl of FIX deficient human plasma was mixed with 100 μl of rhFIX, MOD-3012 (FIX-CTP-CTP (the CTP are in tandem in the C-terminal)), or normal pool human plasma which was further diluted. Following 60 seconds incubation at 37° C. Tissue Factor (TF), $CaCl_2$, and phospholipids were added to the mixture. Clotting time in seconds was determined Potency was assessed by comparing a dose response curve of the MOD3012 to a reference preparation consisting rhFIX or human plasma. One unit of FIX was defined as the amount of FIX which equals to the activity of 1 ml human normal plasma.

Figure 10:
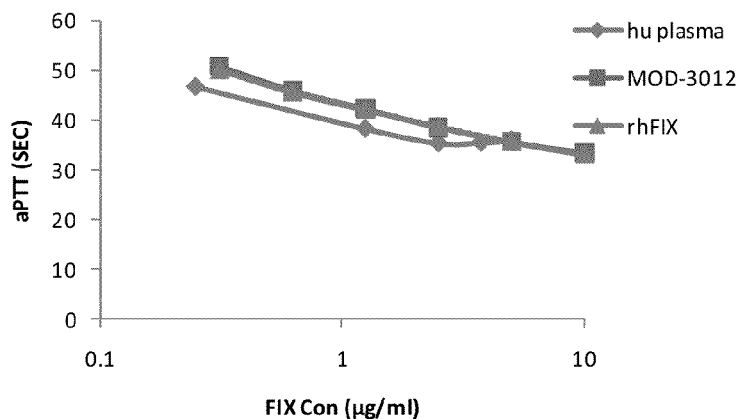
FIG. 10 is a graph showing MOD3012 Comparative coagulation activity compared to human normal pool plasma and rhFIX.

The presented aPTT results (FIG. 10) indicate that MOD3012 coagulation activity is only 1.4 less then normal pool human plasma and similar to the rhFIX. The aPTT results together with the chromogenic activity in-vitro assay suggest that MOD-3012 purification didn't damage its activity.

Pharmacokinetic Activity of MOD3012

Purified MOD3012, rhFIX (American Diagnostic) and harvests containing MOD3012 and MOD3011 (FIX-CTP) were administered in a single intravenous injection to Sprague Dawley rats (eight rats per substance) in a dose of 100 μg/kg body weight.

TABLE 2

| | | PK study outline | | | | | |
|---|---|---|---|---|---|---|---|
| Treated. Groups | Test Article | No. of animals/ group/ time point | Dose Level (μg/kg) | Dose Level (μg per animal) | Injected Vol. (μl) | Con. (μg/ml) | Time- Points (hours post-dose) |
| A | rFIX | 8 | 100 | 20 | 500 | 40 | 0 (Pre-dose) 0.083, 0.5, 1, 2, 4, 7, 10, 24, 48, 72. |
| B | rFIX-CTP (harvest) | 8 | 100 | 20 | 500 | 40 | 0 (Pre-dose) 0.083, 0.5, 1, 2, 4, 7, 10, 24, 48, 72. |
| C | rFIX-CTP-CTP (harvest) | 6 | 100 | 20 | 500 | 40 | 0 (Pre-dose) 0.083, 0.5, 1, 2, 4, 7, 10, 24, 48, 72. |
| D | rFIX-CTP-CTP (purified) | 4 | 100 | 20 | 500 | 40 | 0.083, 0.5 1, 2, 4, 7, 10, 24, 4, 8, 72. |

Figure 11:
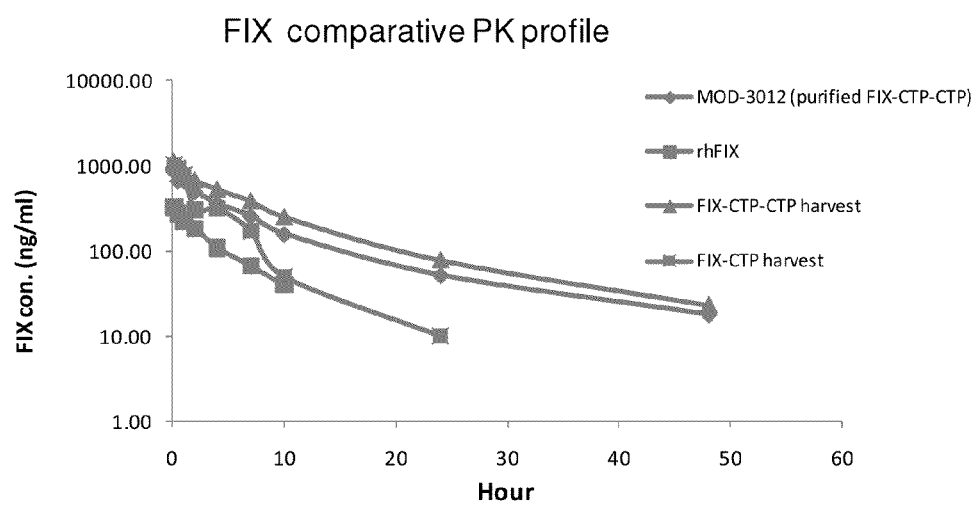
FIG. 11 is a graph showing PK profile of purified MOD3012, rhFIX, harvest of FIX-CTP-CTP, and harvest of FIX-CTP.

Blood samples were drawn retro-orbitally from 4 rats alternately at 0.083, 0.5, 2, 4, 7 10, 24, 48, and 72 hours post dosing. Citrated plasma (0.32%) was prepared immediately after sampling and stored at −20° C. until analysis. FIX concentration was quantitated using human FIX Elisa kit (Affinity Biologicals). Pharmacokinetic profile was calculated for each protein as the mean of 4 animals at each time point (FIG. 11). Terminal half live was calculated using PK solutions 2.0 software. Table 3 summarizes the observed FIX concentrations at different sampling time points. Summary of the PK parameters are also presented in table 4.

TABLE 3

PK profile summary

| Time (hr) | FIX-CTP harvest ng/ml | FIX-(CTP)$_2$ harvest ng/ml | rhFIX ng/ml | Purified MOD-3012 ng/ml |
|---|---|---|---|---|
| 0.085 | 1038.97 | 1123.62 | 325.05 | 886.48 |
| 0.5 | 939.12 | 956.80 | 274.58 | 670.92 |
| 1 | 791.97 | 843.85 | 222.90 | 674.17 |
| 2 | 304.98 | 673.31 | 186.00 | 503.91 |
| 4 | 315.37 | 525.50 | 109.69 | 357.36 |
| 7 | 171.45 | 384.36 | 67.62 | 257.02 |
| 10 | 50.34 | 250.73 | 40.20 | 158.66 |
| 24 | 10.07 | 78.50 | BLQ | 52.13 |
| 48 | BLQ | 23.40 | BLQ | 18.07 |

TABLE 4

Summary of PK parameters

| | T½ (hr) | AUC hr/ml | ng-MRT (hr) | Vd ml/Kg | CL Ml/hr/Kg |
|---|---|---|---|---|---|
| FIX-CTP harvest | 4.17 | 3622 | 4.5 | 155.1 | 27.6 |
| FIX-(CTP)$_2$ harvest | 10.44 | 9105.7 | 12 | 165.4 | 10.9 |
| rhFIX | 3.72 | 1416.8 | 5.1 | 373.8 | 70.183 |
| Purified MOD-3012 | 11.14 | 6314.2 | 12.3 | 254.5 | 15.83 |

MOD-3012 harvest demonstrated an improved PK profile compared to MOD3011 harvest. Furthermore, Purified MOD-3012 exhibit 3-fold increase in T1/2$_\beta$ value and 4.5 fold increase in AUC compared to rhFIX.

The reduced amount of secreted FIX fused to tandem two CTP molecules versus fusion of a single CTP seems to be due to the addition of an extra CTP and not to reduced detection by ELISA. This assumption is based on the fact that Bradford purified MOD-3012 calculated concentration was similar to the obtained ELISA calculated concentration.

MOD3012 clotting activity was similar to pull human plasma; however, its in-vitro chromogenic activity was significantly lower when compared to rhFIX or pooled human plasma. The chromogenic activity assay was reported as a very sensitive assay compared to the coagulation assay. The reason for reduced activity of MOD3012 may vary. Decrease affinity to FXIa by the addition of CTP or reduced post transcriptional modifications (e.g. 12-10 GLA residues and pro-peptide cleavage). N-terminal analysis revealed that the proteolytic cleavage of the MOD-3012 pro-peptide was not fully completed prior to secretion. Since this posttranscriptional modification is crucial for the normal enzymatic activity of the protein, co-transfection with Furine-PACE plasmid is favorable and may improves MOD3012 activity.

Finally, MOD-3012 comparative PK study in rats demonstrated that fusion of two tandem CTPs to the C-terminal of FIX, generated a FIX with extended half life. Comparing the PK properties of MOD-3012 to FIX-FC or FIX-FP (competitive recombinant proteins; table 5 below) indicates that MOD3012 has an improved T1/2 compared to FIX-FP but reduced T1/2 compared to FIX-FC.

TABLE 5

PK properties of long lasting FIXs

| Product | Company | T½ (Ratio) | AUC | CL |
|---|---|---|---|---|
| FIX-FP | CSL-Behring | 2 | Not Indicated | Not Indicated |
| MOD-3012 | Prolor | 3 | 4.5 | 4.7 |

Ratio=long lasting/rhFIX or BeneFIX

FIX Depleted Mouse Model

In order to assess the in-vivo activity model, FIX knockout mice were obtained and a breeding colony was established. 10 μg of either commercial recombinant hFIX (Benefix) or rFIX-(CTP)$_2$ (MOD-3012) are injected into the tail vein of an anaesthetized FIX knockout mouse (22-28 g). The amount of injected protein equals to the required concentration of FIX in normal plasma (5 μg/ml). Blood samples are taken from the dipped tail into heparinized capillary tubes at specific time points. Plasma samples are assessed for FIX levels by ELISA and efficacy is measured by aPTT coagulation assay.

Increasing FIX Propeptide cleavage efficacy: CTP peptide cDNA was fused to the 3' end of human FIX cDNA. The corresponding rFIX and Furin expressing constructs were co-transfected into Dg44 cells; a human rFIX cDNA was also co-transfected with the Furin plasmid as a control. Secretion of high level of FIX leads to secretion of a mixture of pro-factor and a mature factor FIX, due to limited amount of the Furin protease in the cell. Co-transfection of a Furin expressing vector with a pro-factor expressing vector increases the recovery and result in the secretion of fully processed FIX in to the medium.

Following FIX-(CTP)$_2$ and Furin co-transfection stable clones are generated and harvest is collected for pro peptide cleavage evaluation. 100 ng of protein, are loaded on 12% Tris-Glycine gel using Precision plus dual color protein marker (Bio-Rad). The SDS-PAGE analysis is performed by western immunoblot using anti human FIX polyclonal Ab (American Diagnostics) and anti pro peptide polyclonal antibody. As previously reported rhFIX migrated at 55 KDa, while FIX fused to two CTPs migrated at 75 KDa. Both variants of FIX-proteins are shown to undergo a proper, full pro-peptide cleavage.

To determine whether proper pro-peptide cleavage improve FIX-(CTP)$_2$ enzymatic activity, a comparative assessment of chromogenic and coagulation activity of FIX-(CTP)$_2$ harvest co transfecated with Furin is performed. A significant improvement in FIX-(CTP)$_2$ specific activity is observed which is similar to rhFIX was observed.

In conclusion, the results described herein suggest that MOD-3012 can be used efficiently for treating Hemophilia B patients. FIX fused to CTP constructs benefit from improved in-vivo pharmacologic performance that overcomes the drawback in certain in-vitro measures. This proposed treatment is advantageous over previous treatments as the rate of infusions and the amount of required doses are reduced.

It is important to notice that when an Albumin fused molecule strategy was used to improve the FIX half life the recombinant FIX became inactive. Using the present novel approach, lead to the design and purification of a novel recombinant FIX fused protein that presents an improved long lasting activity. Since mere size modifications didn't improve the pharmacokinetic of injected FIX. The finding that CTP fused to FIX facilitates pharmacokinetic parameters was unexpected. The presence of highly glycosylated peptide-sialic acid residues stabilized the protein and protected it from interactions with vascular receptors without abrogating key determinants of FIX function.

FIX-CTP has a similar therapeutic efficacy to rFIX in hemophilia B patients and required less frequent dosing. It also may appear that a single injection of FIX-CTP is sufficient to control bleeding episodes and reduce the number of injections that are needed during surgical intervention in hemophilic B patients.

Example 2

Generation and Utilization of Coagulation Factor FVII

Recombinant coagulation factor VIIa (NovoSeven) (FVIIa) was commercially available and was approved in 1996 for treatment of bleeding episodes in hemophilia patients with inhibitors. However, rFVIIa had a major disadvantage-rFVIIa was rapidly cleared with a terminal half life of 2.5 hours. As a result, patients generally required multiple, frequent infusions (2-3 doses given in 2-3 hours interval) to achieve adequate homeostasis following a mild to moderate bleed.

Here the generation of a recombinant FVIIa-CTP molecule with an extended half life based on fusion of FVII to a human CTP, as described. The recombinant FVIIa-CTP was expressed in mammalian cells and characterized In-vitro and In vivo. It was demonstrated that rFVII-CTP activity was comparable to rFVII, Pharmacokinetic and efficacy studies in rats demonstrated improved properties of the rFVII-CTP. The results of this study demonstrated that it is feasible to develop a half life extended rFVIIa molecule with very similar haemostatic properties to the wild type enzyme.

Cloning and expression of recombinant FVII molecule: Several Factor VII clones were constructed in our eukaryotic expression vector (pCI-dhfrr) (FIG. 1). Human MGC verified FL cDNA clone (IRCM) containing the sequence of *Homo sapiens* coagulation factor VII was ordered from "Open Biosystems" (OB-MHS4426). The following primers were synthesized by Sigma-Genosys in the following sequence: Primer 67: 5'CTCGAGGACATGGTCTCCCAGGCCC3' (contains the 5' end of Factor VII DNA and the restriction site of XhoI) (SEQ ID NO: 5); Primer 68$^R$: 5' TCTAGAATAGG-TATTTTTCCACATG3' (contains the restriction site of XbaI) (SEQ ID NO: 6); Primer 69: 5' TCTAGAAAAAAGAAAT-GCCAGC3' (contains the restriction site of XbaI) (SEQ ID NO: 7); and Primer 70$^R$: 5'GCGGCCGCATCCTCAGG-GAAATGGGGCTCGCA3' (contains the 3' end of Factor VII DNA and the restriction site of NotI) (SEQ ID NO: 8).

Cloning was performed in two sets of PCR reaction. The first reaction was conducted with primer 67 and primer 68$^R$ and cDNA plasmid with Factor VII sequence (OB-MHS4426) was used as a template; as a result of the PCR amplification, a ~534 by product was formed, isolated and ligated into TA cloning vector (Invitrogen, catalog K2000-01). XhoI-XbaI fragment containing the amino terminus of factor VII sequence was isolated. The second reaction was conducted with primer 69 and primer 70$^R$ and again cDNA plasmid with Factor VII sequence (OB-MHS4426) was used as a template; as a result of the PCR amplification, a ~813 by product was formed and ligated into TA cloning vector (Invitrogen, catalog K2000-01). XbaI-NotI fragment containing the Carboxy terminus of Factor VII sequence was isolated. The two fragments were inserted into our eukaryotic expression vector pCI-dhfr (triple ligation) to yield 501-0-p136-1 clone.

Plasmid 501-p136-1 (Factor VII in pCI-dhfr vector) was digested with restriction enzymes XhoI and KpnI. A fragment of ~1186 by was isolated. A partial Factor VII clone (1180 bp-1322 bp) followed by CTP sequence, termination sequence and NotI sequence that was synthesized by GeneArt (0721543) was digested with restriction enzymes KpnI and NotI. A fragment of ~253 by was isolated. The two fragments were inserted into our eukaryotic expression vector pCI-dhfr (triple ligation) to yield 501-1-p137-2 clone. pCI-dhfr-701-2-p24-2 was digested with restriction enzymes XhoI and ApaI and the large fragment (vector) was isolated.

pCI-dhfr-501-2-p137-2 (Factor VII-ctp x1) was digested with restriction enzymes XhoI and ApaI and ~1200 by insert was isolated. The vector and insert were ligated to yield 501-2-p139-2. Dg44 cells were plated in 100 mm tissue culture dishes and grown to confluence of 50-60%. A total of 2 ug of DNA was used for transfection of one 100 mm plate using the FuGene reagent (Roche) in protein free medium (Invitrogen CD Dg44). The media was removed 48 hours post transfection and replaced with a protein free medium (Invitrogen CD Dg44) without nucleosides. After 14 days the transfected cells population were transferred into T25 tissue culture flasks and the selection was continued for 10-14 days until the cells began to grow well as a stable clone. High expressing clones were selected and approximately $2 \times 10^7$ cells were used to inoculate 300 ml of growth medium in a 1700 cm$^2$ roller bottle (Corning, Corning N.Y.) supplemented with 5 ng/ml of Vitamin K3 (menadione sodium bisulfate; Sigma). The production medium (harvest) was collected after a rapid decrease in the cells viability to around 70%. The production medium was first clarified using and then concentrated approximately 20 fold and dialyzed to PBS using flow filtration cassette (10KDaMWCO; Millipore Corp, Billerica, Mass.)

Determination of FVII Antigen Level

Figure 2A:
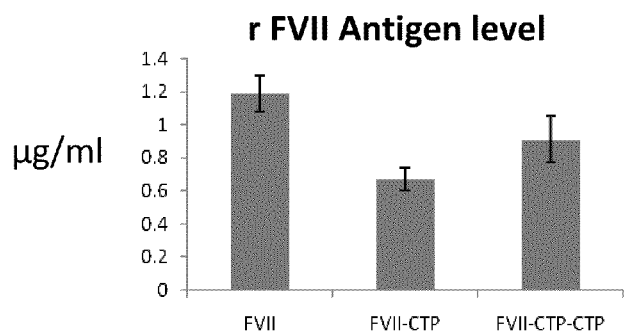
FIG. 2A is a bar graph showing harvests limited diluted clone transfected and selected cells with FVII-CTP variants in the presence of 5 µg/ml of Vitamin K3. The level of FVII was quantified using FVII Elisa (AssayPro).

The cDNA coding the CTP peptide was fused to the 3' end of the cDNA coding human FVII. The corresponding rFVII construct was transfected into Dg44 cells. As a control, a human rFVII cDNA was utilized. The production medium (harvest) was collected, concentrated and the secreted recombinant FVII was further evaluated. rFVII, rFVII-CTP and rFVII-CTP-CTP antigen levels were determined by Assay-Max Human FVII ELISA kit (AssayPro) (FIG. 2A). There was no significant difference in the secretion level of rFVII-CTP and rFVII-(CTP)$_2$ compared to native rFVII.

SDS-PAGE Blots

SDS-PAGE analysis was done by loading 50 ng of either harvest, purified or activated rFVII protein. Samples were loaded on 12% Tris-Glycine gel using Precision plus dual color protein marker (Bio-Rad). The SDS-PAGE analysis was done by performing a western immunoblot using an anti human FVII monoclonal Ab (R&D systems) or anti-CTP polyclonal antibody generated in Rabbit.

Figure 2B:
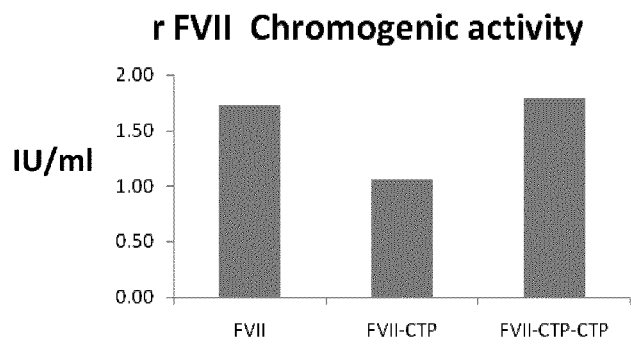
FIG. 2B is a bar graph showing harvests of limited diluted transfected and selected cells with FVII-CTP variants in the presence of 5 µg of Vitamin K3.activity. FVII activity was quantified using FVII chromogenic activity assay (Assay-Pro).
Figure 2C:
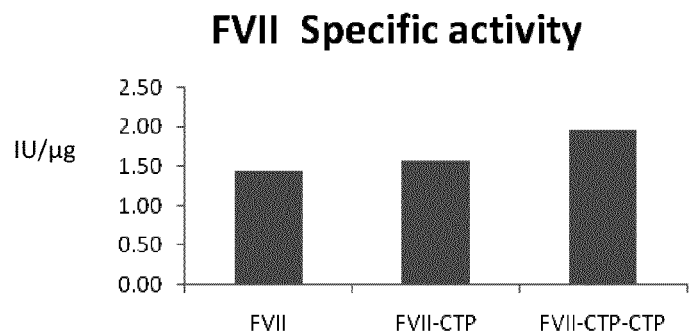
FIG. 2C is a bar graph showing harvests of limited diluted transfected and selected cells with FVII-CTP variants in the presence of 5 µg of Vitamin K3. The specific activity of FVII was calculated for each version by dividing the activity value by the harvest FVII concentration.

The level of rFVII antigen correlated to the detected protein level in a SDS-PAGE immunoblotted with anti FVII Ab. rFVII-CTP migrated as a single band while the corresponding molecular weight of the FVII control was approximately 52 KDa, both proteins reacted with antibodies specific for FVII on immunoblots. The rFVII-CTP also reacted with antibodies specific for CTP. rFVII was secreted in its zymogene form with no trace of activated protein FVII Chromogenic Activity:

rFVII, rFVII-CTP and rFVII-(CTP)$_2$ harvests activity was determined using a commercially available chromogenic test kit (AssaySense Human FVII chromogenic Activity assay kit (AssayPro). For functional characterization of the rFVII-CTP and its ability to be further activated (FVIIa), concentrated rFVII-CTP (harvests) were placed in a commercially available chromogenic test kit that measure the ability of TF/FVIIa to activate factor X to factor Xa that in the presence of FXa specific substrate releases a quantitated signal (AssayPro). The addition of the CTP peptide at the C-terminal of the rFVII protein didn't impair its serine protease activity (FIG. 2B, C).

FVII Clotting Activity:

Prothrombin time (PT) measures the extrinsic pathway of coagulation. The PT is the time (measured in seconds) it takes plasma to clot following the addition of an extrinsic pathway activator, phospholipid and calcium. It is used to determine the clotting tendency of blood, specifically in the measure of warfarin dosage, liver damage, and vitamin K status. The reference range for prothrombin time is usually around 12-15 seconds. Specifically, the assay quantitated the ability of FVII-CTP and FVII-(CTP)$_2$ harvest to restore the clotting activity of FVII depleted human plasma by the addition of rhFVII. 300 µl of FVII deficient human plasma was mixed with 100 µl of FVII, FVII-CTP and FVII-(CTP)$_2$ harvets at specific concentrations, or normal pool human plasma and were further diluted. Following 60 seconds incubation at 37° C., Tissue Factor (TF), CaCl$_2$, and phospholipids were added to the mixture. Clotting time in seconds was determined Potency was assessed by comparing a dose response curve of FVII-CTP and FVII-(CTP)$_2$ harvests to a reference preparation consisting rhFVII or human pool plasma. One unit of active FVII was defined as the amount of FVII which equals to the activity of one ml human normal plasma. The PT Clotting activity of rFVII and rFVII-CTP was measured on a coagulometer (Instrumentation Laboratory).

Figure 2D:
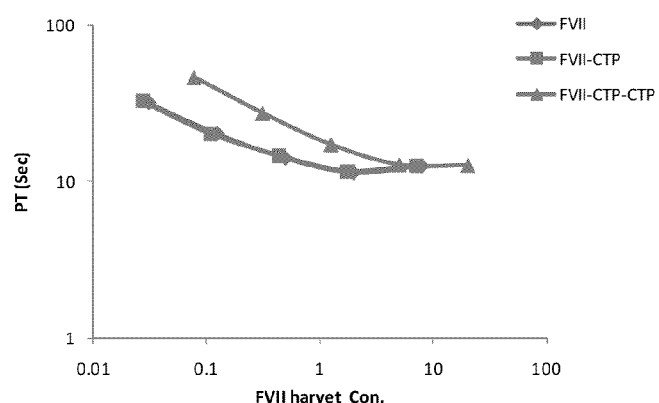
FIG. 2D is a graph showing harvests of limited diluted transfected and selected cells with FVII, FVII-CTP and FVII-(CTP)$_2$ coagulation activity compared to normal poll human plasma coagulation activity.
Figure 2E:
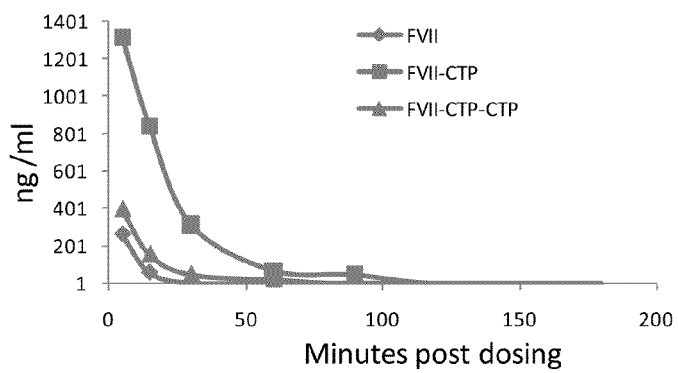
FIG. 2E is a graph showing PK profile of FVII, FVII-CTP-CTP, and FVII-CTP harvests.

As previously shown the addition of the CTP peptide at the C-terminal of the rFVII protein didn't damage its serine protease activity and lead to initiation and activation of a native factor X and factor IX in human plasma. Following Additional CTP at the C terminal three fold reduction the serine protease activity was observed (FIG. 2D)

Pharmacokinetics Study:

rFVII, rFVII-CTP, and rFVII-(CTP)$_2$ harvests were administered intravenously to Sprague Dawley rats (six rats per substance) with a dose of 100 µg/kg body weight. For all the in-vivo experiments the amount of the respective protein was determined on the basis of FVII Elisa kit. For each FVII test substance the injected amount was calculated by taking into account the differences in the molecular weight of rFVII verses rFVII-CTP which leads to different molar concentration.

Blood samples were drawn retro-orbitally using an altering sampling scheme to minimize interference of the sampling procedure levels to be quantified: from 3 Rats at, 30 min and 90, 2, 6, and 48 hrs, and from the remaining three rats at 15, 60 min and 1.5, 4, 24 hrs alternately. Plasma was prepared immediately after sampling and stored at −20° C. until analysis. FVII concentration was quantified by FVII Elisa specific assay. Half life and area under the curve (AUC) were calculated using linear trapezoidal rule. Comparison of these clearance parameters revealed that the in-vivo half life and rFVII-(CTP)$_2$ AUC are significantly higher than those of rFVII (Table 8).

TABLE 6

PK study parameters

| Group | Route | Dose µg/kg | $T_{1/2}$ min | $AUC_{0-t}$ ng/min/mL | CL/F mL/min/kg | MRT min |
|---|---|---|---|---|---|---|
| FVII | IV | 60 | 4.07 | 3314.7 | 6.195 | 6.2 |
| FVII-CTP | IV | 60 | β = 51.06 | 31353.9 | 0.287 | 73.7 |
| FVII-CTP-CTP | IV | 60 | β = 13.66 | 7626.8 | 1.18 | 15.4 |

Characterization of Recombinant FVIIa-CTP:

During activation, FVII is cleaved at R152 resulting in a heavy and a light chain domains that are held together by a single disulfide bridge. rFVIIa-(CTP)$_2$ is purified and activated by ion exchange columns purification process. In order to fully evaluate rFVIIa-(CTP)$_2$, the protein is loaded on SDS-PAGE under reducing conditions to commercial FVIIa (Novoseven®). The heavy and the light chain domains are separated and migrate as separated bands of molecular weights 55 and 25 KDa. Both proteins react with antibodies specific for FVII but the heavy chain of the rFVIIa-CTP specifically reacts with anti-CTP specific antibodies indicating that this band represents the FVII heavy chain fused to CTP. The light chain reacts specifically with anti gamma caroxylase Ab. FVIIa protein concentration is determined by FVIIa specific Elisa kit.

FVIIa N-Terminal Sequencing:

rFVII-CTP-CTP in activated or zymogene purified proteins is separated by SDS-PAGE (on 12% Tris-Glycine) and subsequently electroblotted to PVDF membrane. The bands of interest are cut out and put on a purified Biobrene treated glass fiber filter. The N-terminal sequence analysis is carried out by Edmann degradation using a pulsed liquid protein sequencer equipped with a 140 C HPLC microgradient system. The identity of the recombinant protein and proper pro peptide cleavage is further verified by N-terminal sequencing.

FVIIa Clotting Activity:

In order to evaluate FVII-(CTP)$_2$ coagulation activity, activated partial thromboplastin time assay (aPTT) is performed. FVIII deficient plasma sample is substituted with rFVIIa (NovoSeven) or rFVIIa-(CTP)$_2$, 300 µl of FVII deficient human plasma is mixed with 100 µl of FVIIa or rFVIIa-(CTP)$_2$ at specific concentrations, or normal pull human plasma which is further diluted. Following 60 seconds incubation at 37° C. Tissue Factor (TF), CaCl$_2$, and phospholipids are added to the mixture. Clotting time in seconds is determined Potency is assessed by comparing a dose response curve of rFVIIa-(CTP)$_2$ to a reference preparation consisting rhFVIIa or human pool normal plasma. One unit of FVIIa is defined as the amount of FVIIa which equals to the activity of 1 ml human normal plasma. The aPTT Clotting activity of rFVII and rFVIIa-(CTP)$_2$ is measured on a coagulometer (Instrumentation Laboratory). The aPTT Clotting activity of rFVIIa and rFVIIa-(CTP)$_2$ is similar.

Pharmacokinetics Studies in Rats:

In order to Characterize the influence of the CTP addition to the rFVIIa on its longevity potential a comparative pharmacokinetic study in rats is performed. NovoSeven (rFVIIa) and rFVIIa-(CTP)$_2$ in TBS are injected IV to 6 SD rats. The time course levels of FVIIa are detected using FVIIa Elisa kit. Half life and AUC are calculated for each protein. Comparison of these clearance parameters reveals that the in-vivo measures of half life, recovery, and AUC of the rFVIIa-(CTP)$_2$ are superior to those of NovoSeven.

FVIIa-CTP In-Vivo Efficacy Model:

In order to evaluate the in-vivo activity of the rFVIIa-(CTP)$_2$, 6 SD rats are treated with phenprocoumn in order to inhibit vitamin K depended gamma carboxylation of the coagulation factors Gla domain. Due to the short half life of FVIII, the native FVIII is depleted faster than the other vitamin K dependent coagulation factors. It is shown that after 16 hours the FVIII activity is almost completely depleted. At this time point externally adding FVIIa corrected-reduced clotting time in rats. In order to compare NovoSeven and rFVIIa-(CTP)$_2$, equal dose of both proteins are injected into rats 16 hours post phenprocoumn treatment. Clotting time of rat blood is corrected to normal value by both recombinant proteins. Thus, both proteins display a comparable effect in this model.

In a separate experiment NovoSeven and rFVIIa-(CTP)$_2$ are injected immediately after phenprocoumn treatment but coagulation parameters are determined after 16 hours. NovoSeven does not correct the clotting time under these conditions due to a short half life. In contrast the clotting time of animals treated with rFVIIa-(CTP)$_2$ is corrected to values close to the values of the healthy controls. This indicates that rFVIIa-(CTP)$_2$ is still present and retains biology activity after a longer period. This data further confirms the great advantage in using CTP modified rFVIIa. FIX depleted mouse model (wasn't conducted yet):

FVIII Hemophilic Mice Model:

In order to assess the in-vivo activity model, FVII knockout mice are obtained and a breeding colony is established. 10 µg of either commercial recombinant hFVIIa (Novoseven) or rFVIIa-(CTP)$_2$ are injected into the tail vein of an anaesthetized FVIII knockout mouse (22-28 g). The amount of injected protein equals to the required concentration of FVIII in normal plasma (5 µg/ml). Blood samples are taken from the dipped tail into heparinized capillary tubes at specific time points. Plasma samples are assessed for FVIIa levels by ELISA and efficacy is measured by a PTT coagulation assay.

In this study a fusion construct of FVII with CTP is generated. This recombinant protein is the basis for a treatment that provides a prolonged half life and retention of adequate favorable therapeutic potency.

These results suggest that rFVIIa-(CTP)$_2$ has a similar therapeutic efficacy to rFVIIa in hemophilia patients. Moreover, this technology requires less frequent dosing. It appears that a single injection of rFVIIa-(CTP)$_2$ is sufficient to control bleeding episodes and reduce the number of injections that are needed during surgical intervention. This recombinant protein may be used as a long term prophylactic treatment.

What is claimed is:

1. A polypeptide consisting of a wild type coagulation factor and one to three chorionic gonadotropin carboxy terminal peptides (CTPs) attached to the carboxy terminus of said coagulation factor, wherein said polypeptide comprises coagulating activity and wherein said coagulation factor is Factor IX.

2. The polypeptide of claim 1, wherein said polypeptide consists of said coagulation factor and one or two chorionic gonadotrophin CTPs attached to the carboxy terminus of said coagulation factor.

3. The polypeptide of claim 1, wherein the sequence of at least one CTP is selected from the group consisting of: SEQ ID NO: 1 and SEQ ID NO: 2.

4. The polypeptide of claim 1, wherein at least one CTP is glycosylated.

5. The polypeptide of claim 1, wherein at least one CTP is truncated.

6. The polypeptide of claim 1, wherein at least one CTP is attached to said coagulation factor via a peptide bond.

7. A pharmaceutical composition comprising the polypeptide of claim 1 and a pharmaceutically acceptable carrier.

8. A method of extending the biological half life of a coagulation factor, comprising the step of attaching one to three chorionic gonadotrophin carboxy terminal peptides (CTPs) to the carboxy terminus of said coagulation factor, wherein said coagulation factor comprising one to three CTPs comprises coagulating activity, wherein said coagulation factor is Factor IX, and wherein said coagulation factor is a wild type coagulation factor, thereby improving the biological half life of said coagulation factor.

9. The method of claim 8, wherein the sequence of at least one CTP is selected from the group consisting of: SEQ ID NO: 1 and SEQ ID NO: 2.

10. The method of claim 8, wherein at least one CTP is glycosylated.

11. The method of claim 8, wherein at least one CTP is truncated.

12. The method of claim 8, wherein at least one CTP is attached to said coagulation factor via a peptide bond.

13. A method of improving the area under the curve (AUC) of a coagulation factor, comprising the step of attaching one to three chorionic gonadotrophin carboxy terminal peptides (CTPs) to the carboxy terminus of said coagulation factor, wherein said coagulation factor comprising one to three CTPs comprises coagulating activity, wherein said coagulation factor is Factor IX, and wherein said coagulation factor is a wild type coagulation factor, thereby improving the AUC of said coagulation factor.

14. A method of reducing the dosing frequency of a coagulation factor, comprising the step of attaching one to three chorionic gonadotrophin carboxy terminal peptides (CTPs) to the carboxy terminus of said coagulation factor, wherein said coagulation factor comprising one to three CTPs comprises coagulating activity, wherein said coagulation factor is Factor IX, and wherein said coagulation factor is a wild type coagulation factor, thereby reducing the dosing frequency of said coagulation factor.

15. A polypeptide consisting of a wild type coagulation factor and one to five chorionic gonadotropin carboxy terminal peptides (CTPs) attached to the carboxy terminus of said coagulation factor, wherein said polypeptide comprises coagulating activity and wherein said coagulation factor is Factor VII or Factor VIIa.

16. The polypeptide of claim 15, wherein said polypeptide consists of said coagulation factor and one or two chorionic gonadotrophin CTPs attached to the carboxy terminus of said coagulation factor.

17. The polypeptide of claim 15, wherein the sequence of at least one CTP is selected from the group consisting of: SEQ ID NO: 1 and SEQ ID NO: 2.

18. The polypeptide of claim 15, wherein at least one CTP is glycosylated.

19. The polypeptide of claim 15, wherein at least one CTP is truncated.

20. The polypeptide of claim 15, wherein at least one CTP is attached to said coagulation factor via a peptide bond.

21. A pharmaceutical composition comprising the polypeptide of claim 15 and a pharmaceutically acceptable carrier.

22. A method of extending the biological half life of a coagulation factor, comprising the step of attaching one to five chorionic gonadotrophin carboxy terminal peptides (CTPs) to the carboxy terminus of said coagulation factor, wherein said coagulation factor comprising one to five CTPs comprises coagulating activity, wherein said coagulation factor is Factor VII or Factor VIIa, and wherein said coagulation factor is a wild type coagulation factor, thereby improving the biological half life of said coagulation factor.

23. The method of claim 22, wherein the sequence of at least one CTP is selected from the group consisting of: SEQ ID NO: 1 and SEQ ID NO: 2.

24. The method of claim 22, wherein at least one CTP is glycosylated.

25. The method of claim 22, wherein at least one CTP is truncated.

26. The method of claim 22, wherein at least one CTP is attached to said coagulation factor via a peptide bond.

27. A method of improving the area under the curve (AUC) of a coagulation factor, comprising the step of attaching one to five chorionic gonadotrophin carboxy terminal peptides (CTPs) to the carboxy terminus of said coagulation factor, wherein said coagulation factor comprising one to five CTPs comprises coagulating activity, wherein said coagulation factor is Factor VII or Factor VIIa, and wherein said coagulation factor is a wild type coagulation factor, thereby improving the AUC of said coagulation factor.

28. A method of reducing the dosing frequency of a coagulation factor, comprising the step of attaching one to five chorionic gonadotrophin carboxy terminal peptides (CTPs) to the carboxy terminus of said coagulation factor, wherein said coagulation factor comprising one to five CTPs comprises coagulating activity, wherein said coagulation factor is Factor VII or Factor VIIa, and wherein said coagulation factor is a wild type coagulation factor, thereby reducing the dosing frequency of said coagulation factor.

* * * * *